US008492102B2

(12) United States Patent
Kashani-Sabet et al.

(10) Patent No.: US 8,492,102 B2
(45) Date of Patent: Jul. 23, 2013

(54) MOLECULAR DIAGNOSIS AND CLASSIFICATION OF MALIGNANT MELANOMA

(75) Inventors: Mohammed Kashani-Sabet, San Francisco, CA (US); Christopher Haqq, Newbury Park, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/920,957

(22) PCT Filed: Mar. 5, 2009

(86) PCT No.: PCT/US2009/036227
§ 371 (c)(1),
(2), (4) Date: Jan. 4, 2011

(87) PCT Pub. No.: WO2009/111661
PCT Pub. Date: Sep. 11, 2009

(65) Prior Publication Data
US 2011/0123997 A1 May 26, 2011

Related U.S. Application Data

(60) Provisional application No. 61/034,109, filed on Mar. 5, 2008.

(51) Int. Cl.
*G01N 33/53* (2006.01)
(52) U.S. Cl.
USPC .......................................................... 435/7.1
(58) Field of Classification Search
None
See application file for complete search history.

(56) References Cited

U.S. PATENT DOCUMENTS

| 7,247,426 | B2 | 7/2007 | Yakhini et al. |
| 2002/0155440 | A1 | 10/2002 | Ljubimova et al. |
| 2008/0113360 | A1* | 5/2008 | Riker et al. .................. 435/6 |

FOREIGN PATENT DOCUMENTS

| WO | WO 2008/030986 | 3/2008 |
| WO | WO 2009/111661 | 9/2009 |

OTHER PUBLICATIONS

Rangel et al (Journal of Clinical Oncology, 2006, 24(28): 4565-4569).*
Bauer et al (J Clin Path, 2006, 59: 699-705).*
Tockman et al (Cancer Res., 1992, 52:2711s-2718s).*
Haqq et al. "The gene expression signatures of melanoma progression," PNAS, 2005, vol. 102, No. 17, pp. 6092-6097.
Hoek et al. "Expression Profiling Reveals Novel Pathways in the Transformation of Melanocytes to Melanomas," Cancer Research, 2004, vol. 64, pp. 5270-5282.
Rangel et al. "Prognostic Significance of Nuclear Receptor Coactivator-3 Overexpression in Primary Cutaneous Melanoma," Journal of Clinical Oncology, 2006, vol. 24, No. 28, pp. 4565-4569.
Pham et al. "Wnt ligand expression in malignant melanoma: pilot study indicating correlation with histopathological features," J Clin Pathol: Mol Pathol, 2003, vol. 56, pp. 280-285.
Alonso et al. "Progression in Cutaneous Malignant Melanoma Is Associated with Distinct Expression Profiles," American Journal of Pathology, 2004, vol. 164, No. 1, pp. 193-203.
Rangel et al. "Novel Role for RGS1 in Melanoma Progression," Am J Surg Pathol, 2008, vol. 32, No. 8, pp. 1207-1212.
Li et al. "The profilin:actin complex localizes to sites of dynamic actin polymerization at the leading edge of migrating cells and pathogen-induced actin tails," European Journal of Cell Biology, 2008, vol. 87, pp. 893-904.
Riker et al. "The gene expression profiles of primary and metastatic melanoma yields a transition point of tumor progression and metastasis," BMC Medical Genomics, 2008, 1:13, 16 pages.
Alonso et al., "Progression in Cutaneous Malignant Melanoma is Associated with Distinct Expression Profiles", *American Jouranl of Pathology*, vol. 164, No. 1, pp. 193-203 (2004).
Carlson et al., "Molecular diagnostics in melanoma", *Journal of the American Academy of Dermatolgy*, vol. 52, No. 5, pp. 743-775 (2005).
Curtin et al., "Distinct Sets of Genetic Alterations in Melanoma", *The New England Journal of Medicine*, vol. 353, No. 20, pp. 2135-2147 (2005).
Hoek et al., "Expression Profiling Reveals Novel Pathways in the Transformation of Melanocytes to Melanomas", Cancer Research, vol. 64, pp. 5270-5282 (2004).
Kashani-Sabet et al., "A multi-marker assay to distinguish malignant melanomas from benign nevi", *PNAS*, vol. 106, No. 15, pp. 6268-6272 (2009).
Li et al., "The profilin:actin complex localizes to sites of dynamic actin polymerization at the leading edge of migrating cells and pathogen-induced actin tails", *European Journal of Cell Biology*, vol. 87, pp. 893-904 (2008).
Moratz et al., "Regulator of G Protein Signaling 1 (RGS1) Markedly Impairs G Signaling Responses of B Lymphocytes", *The American Association of Immunologists*, vol. 164, No. 4, pp. 1829-1838 (2000).
Rangel, J. et al., "Prognostic significance of nuclear receptor coactivator-3 overexpression in primary cutaneous melanoma", *Journal of Clinical Oncology*, vol. 24, No. 8, pp. 4565-4569 (2006).
Riker et al., "The gene expression profiles of primary and metastic melanoma yields a transition point of tumor progression and metastasis", *BMC Medical Genomics*, 1:13, 16 pgs. (2008).
Sheffield et al., "Comparison of Five antibodies as Markers in the Diagnosis of Melanoma in Cytologic Preparations", *Am J. Clin. Pathol.*, vol. 118, pp. 930-936 (2002).
Zhou et al., "Osteopontin expression correlates with melanoma invasion", *J. Invest. Dermatolo*, vol. 124, pp. 1044-1052 (2005).
Philip et al., "Osteopontin Stimulates Tumor Growth and Activation of Promatrix Metalloproteinase-2 through Nuclear Factor-kappa B-mediated Induction of Membrane Type 1 Matrix Metalloproteninase in Murine Melanoma Cells", Journal of Biological Chemistry, vol. 276, No. 48 , pp. 44926-44935 (2001).

* cited by examiner

*Primary Examiner* — Sean Aeder
(74) *Attorney, Agent, or Firm* — Morgan, Lewis & Bockius LLP; Annette S. Parent

(57) ABSTRACT

The present invention provides methods for diagnosing and providing a prognosis of melanoma using molecular markers that are overexpressed in melanoma cells. The invention provides kits for diagnosis and prognosis. Also provided are methods to identify compounds that are useful for the treatment or prevention of melanoma and melanoma progression.

9 Claims, 30 Drawing Sheets

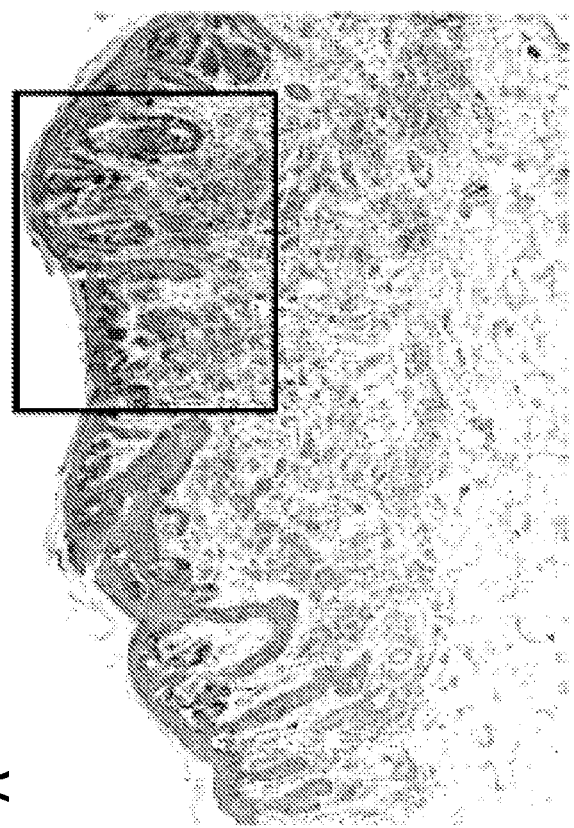
Fig. 8

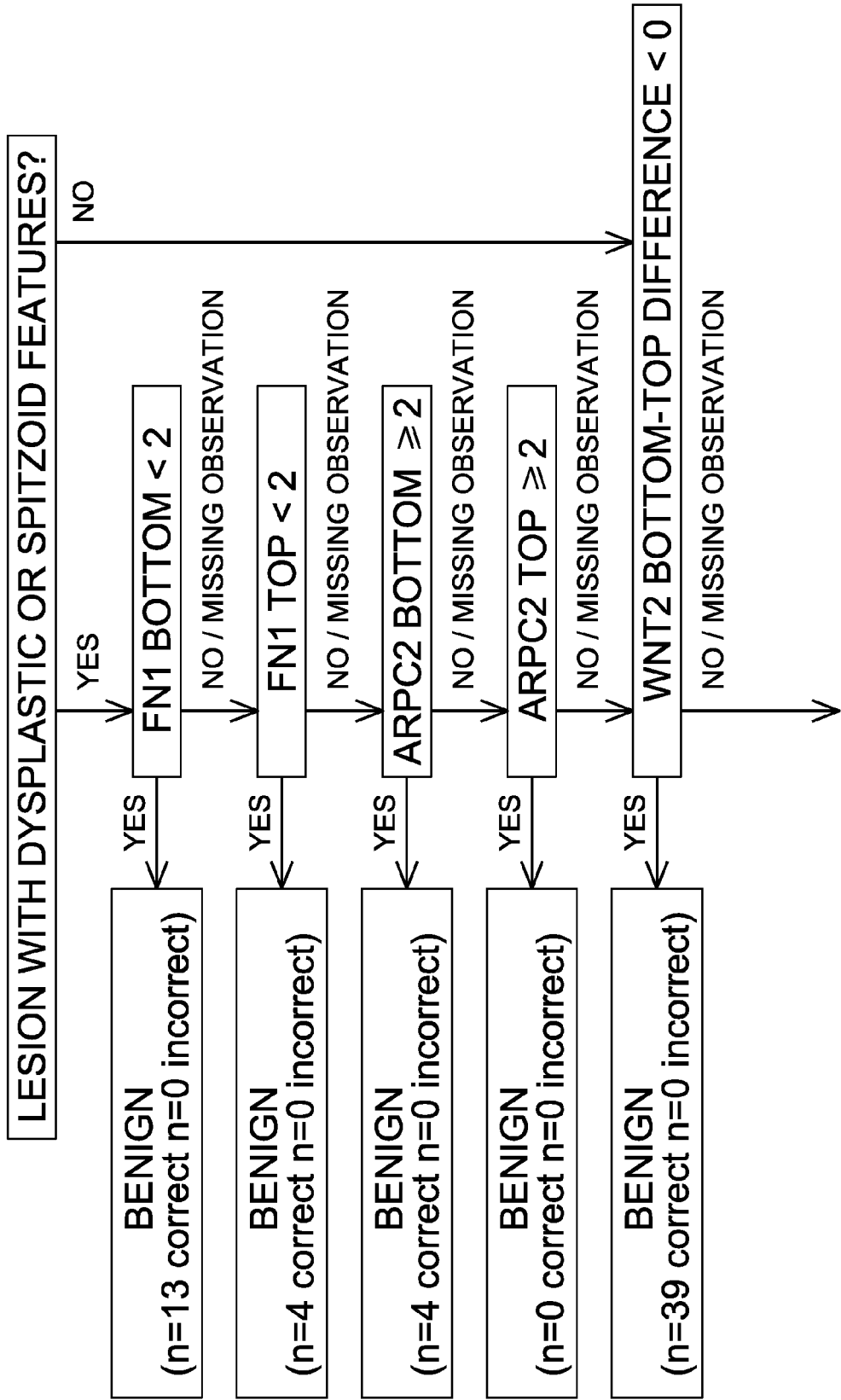
Fig. 16 Sheet 1

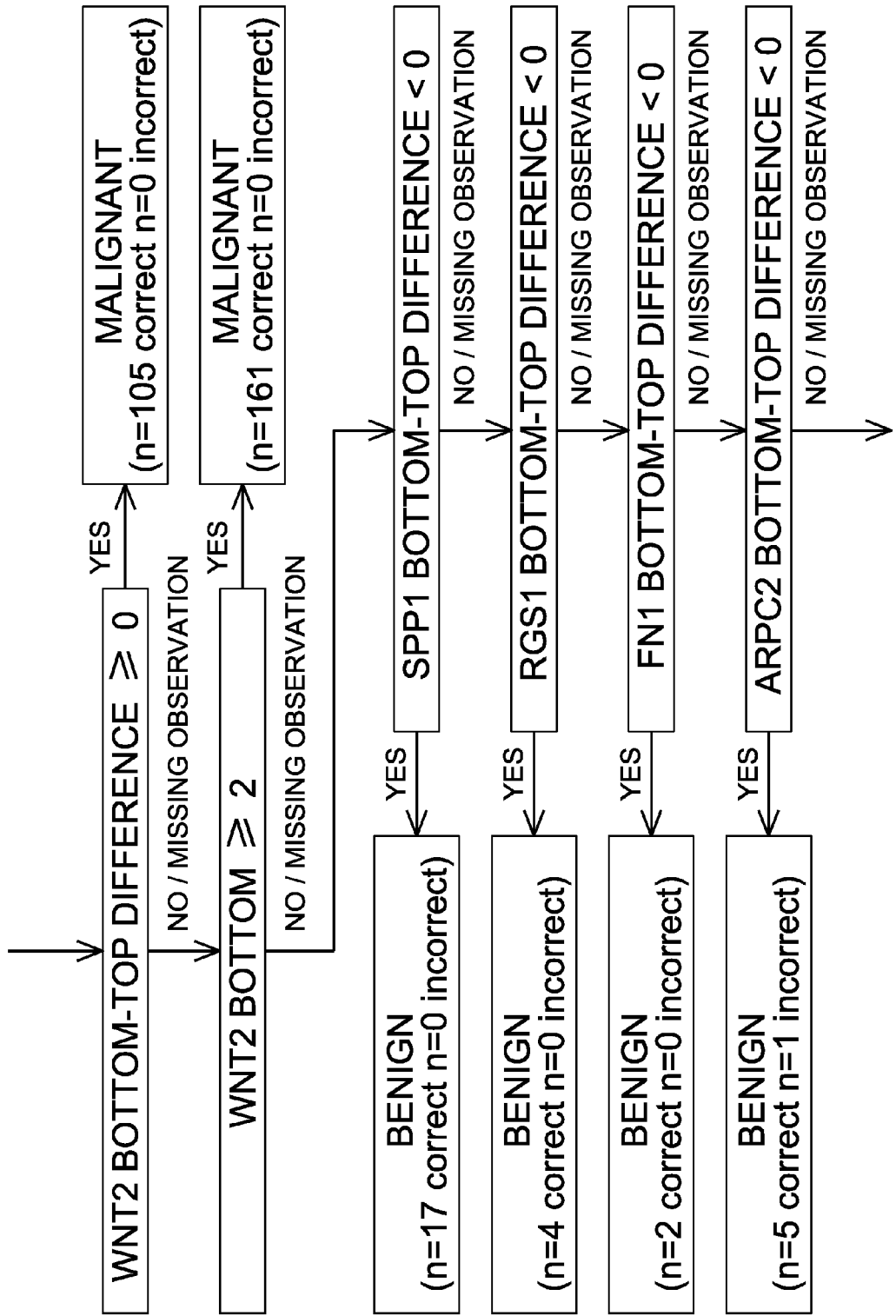
Fig. 16 Sheet 2

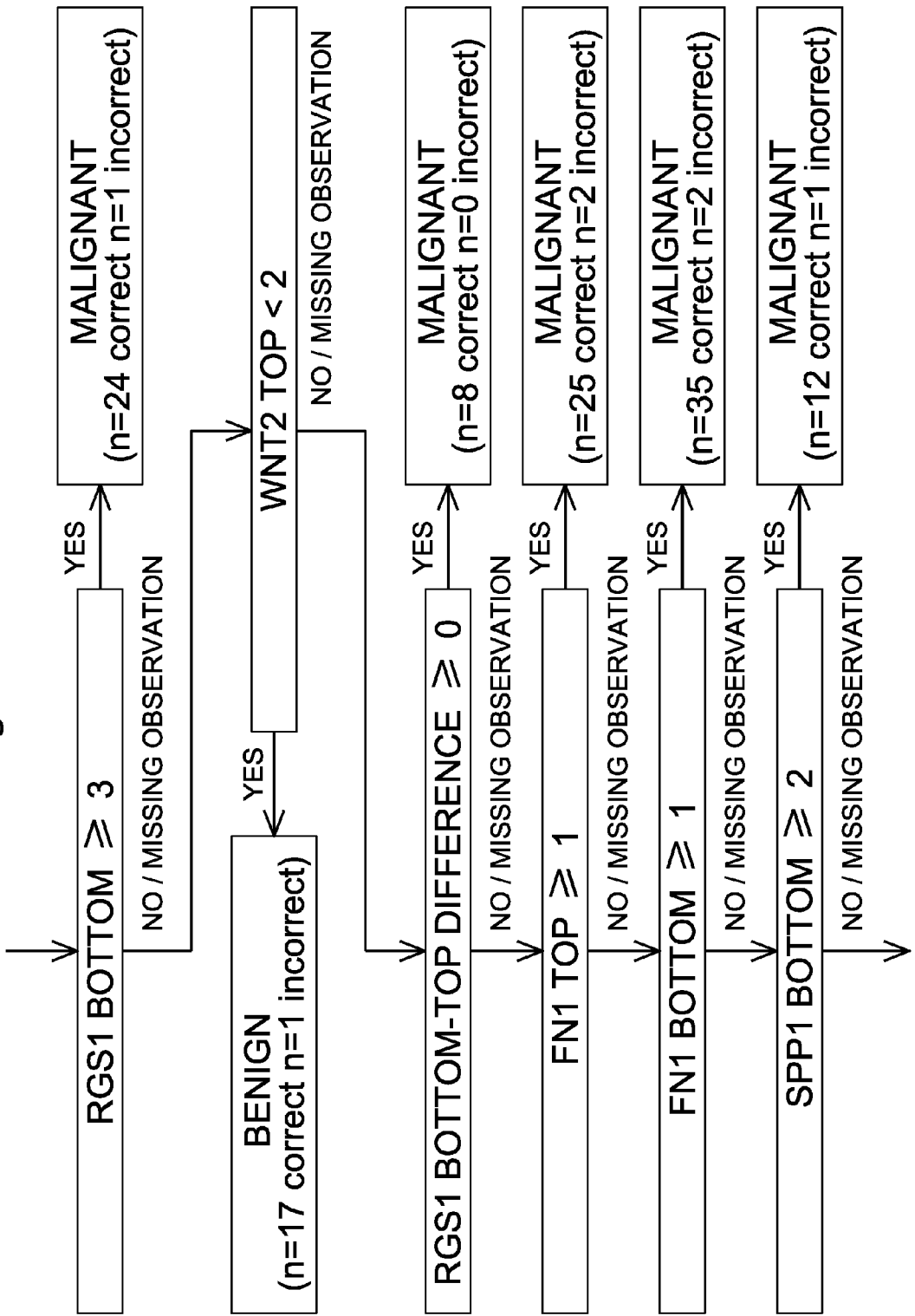
Fig. 16 Sheet 3

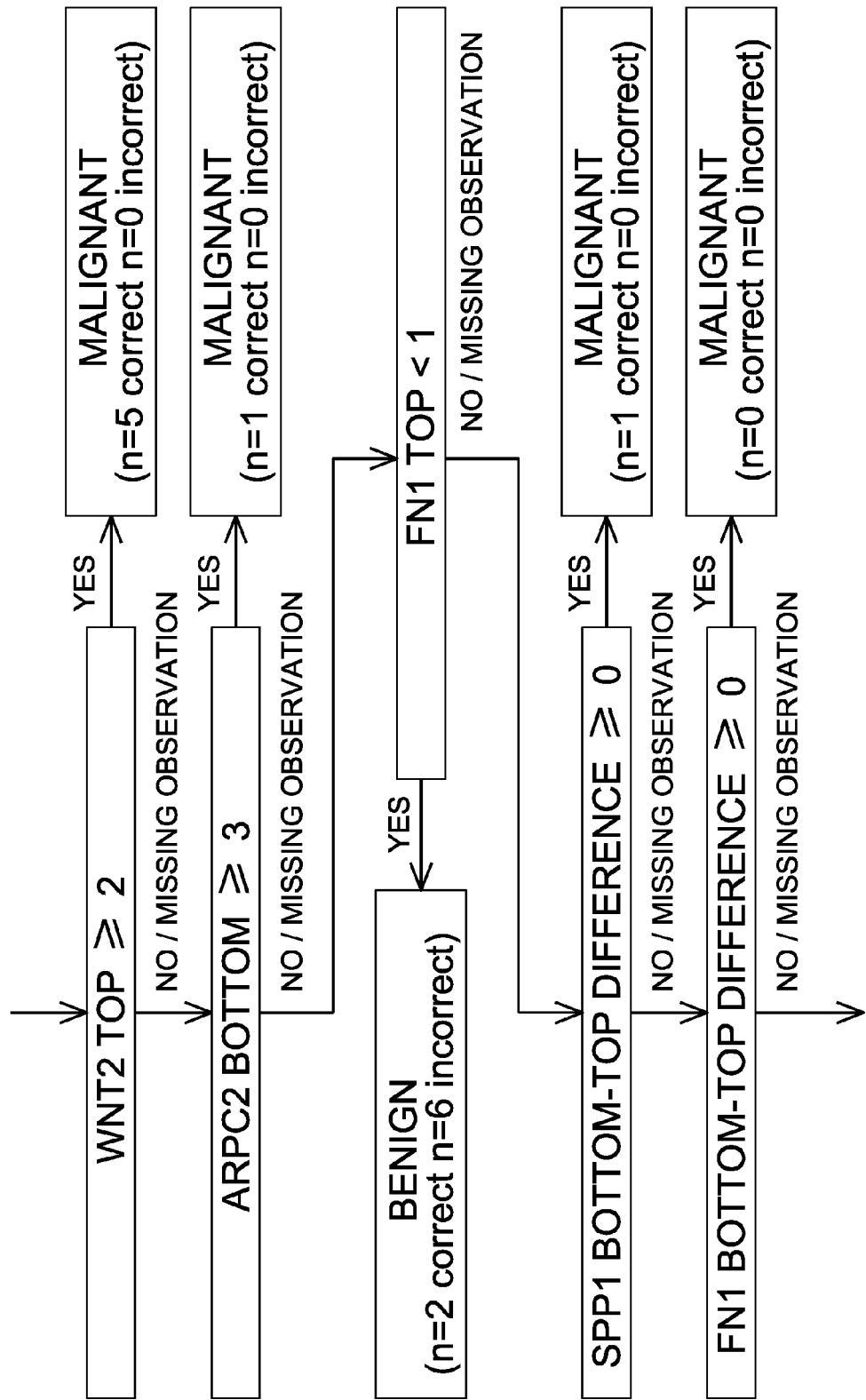
Fig. 16 Sheet 4

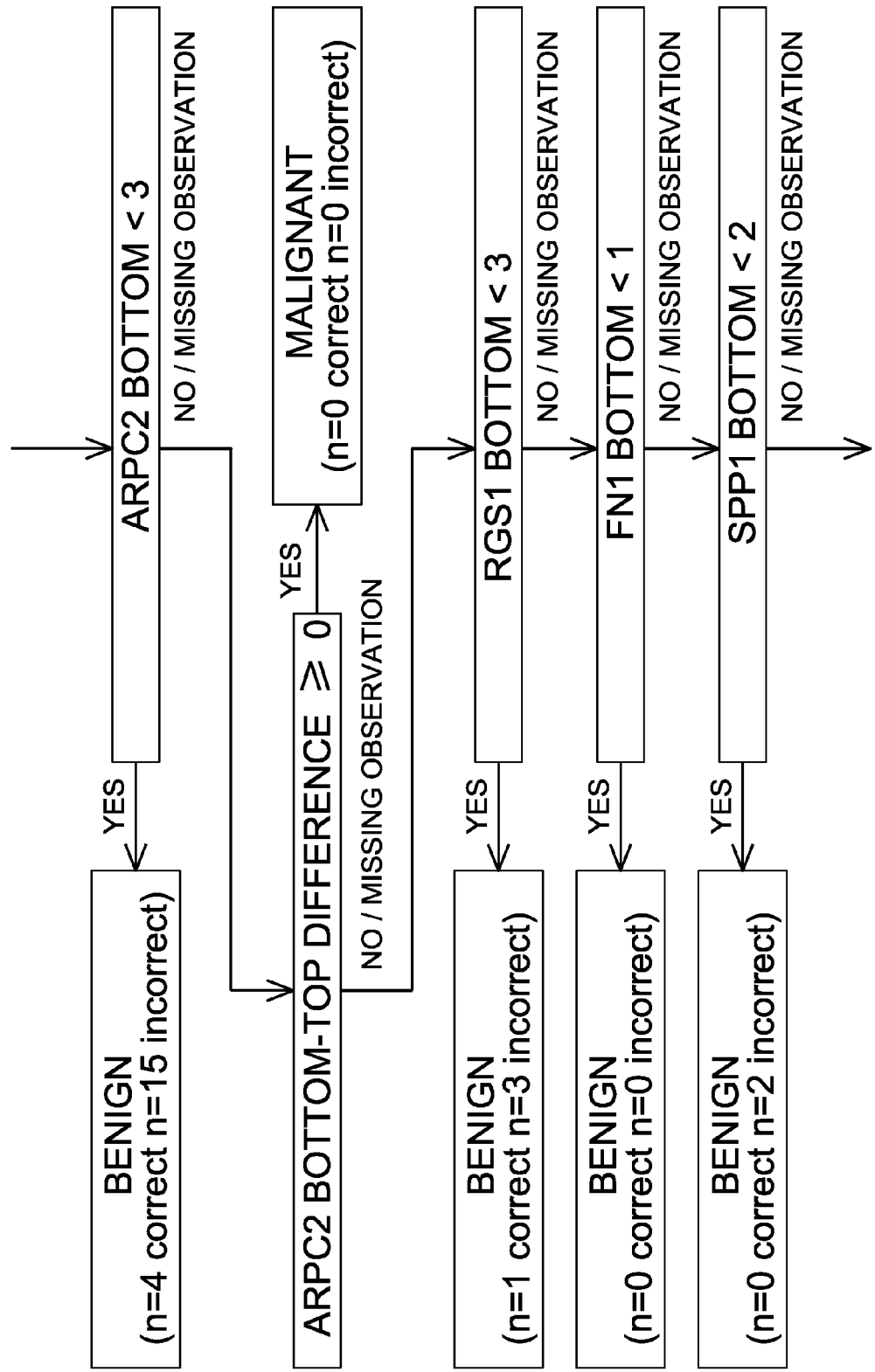
Fig. 16 Sheet 5

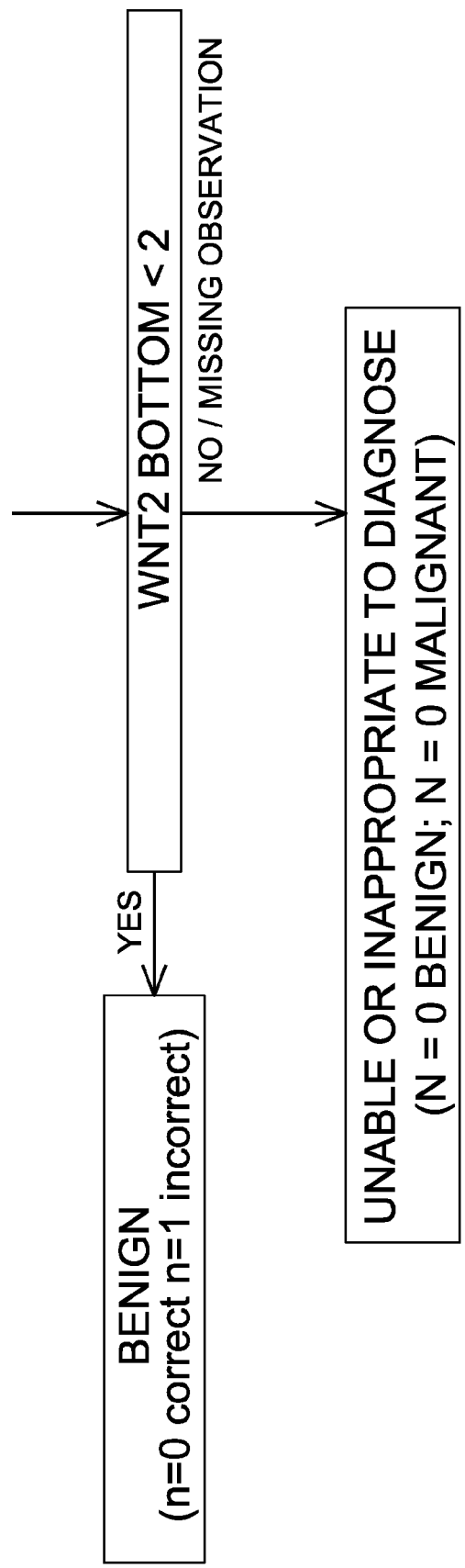
Fig. 16 Sheet 6

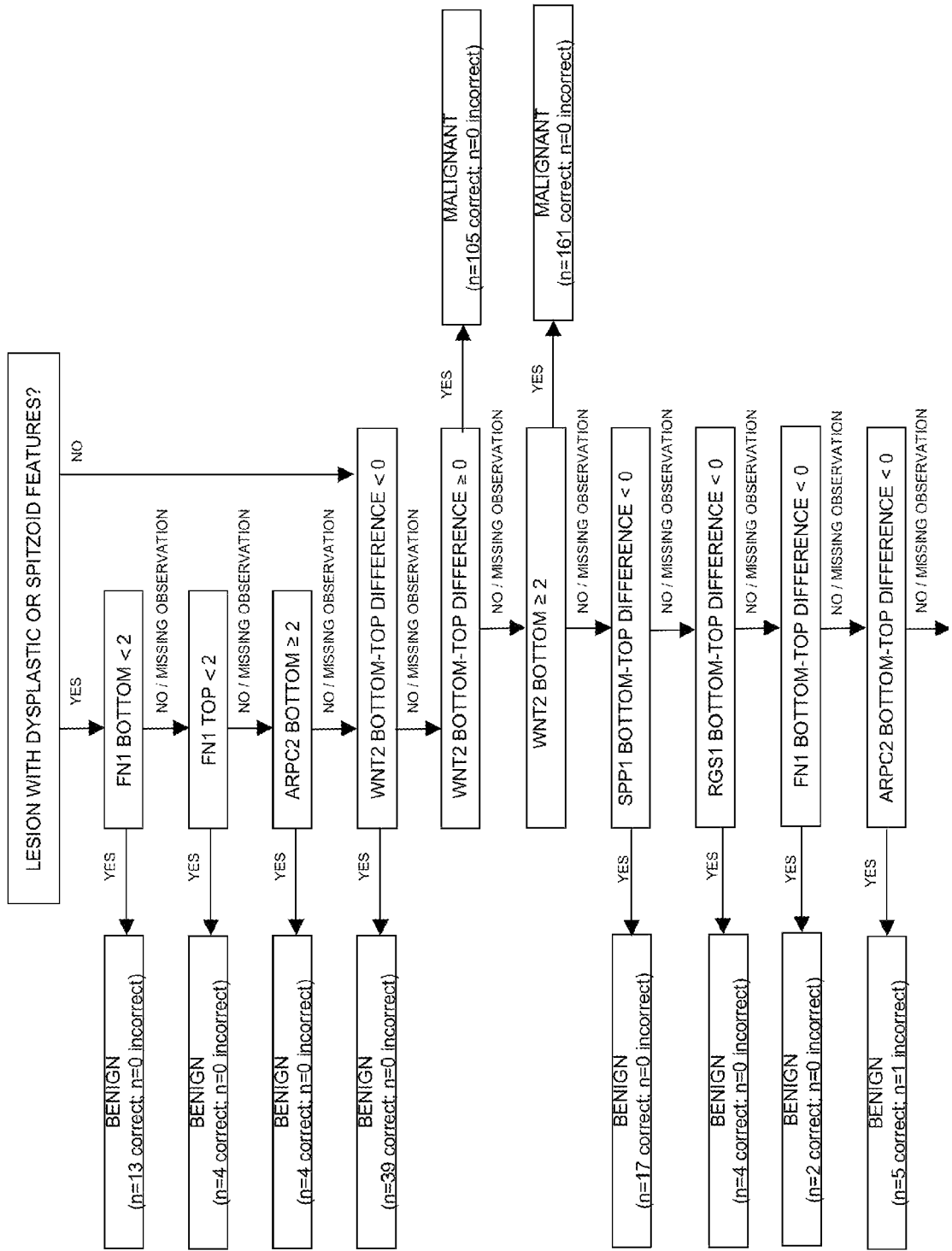
Fig. 23 sheet 1

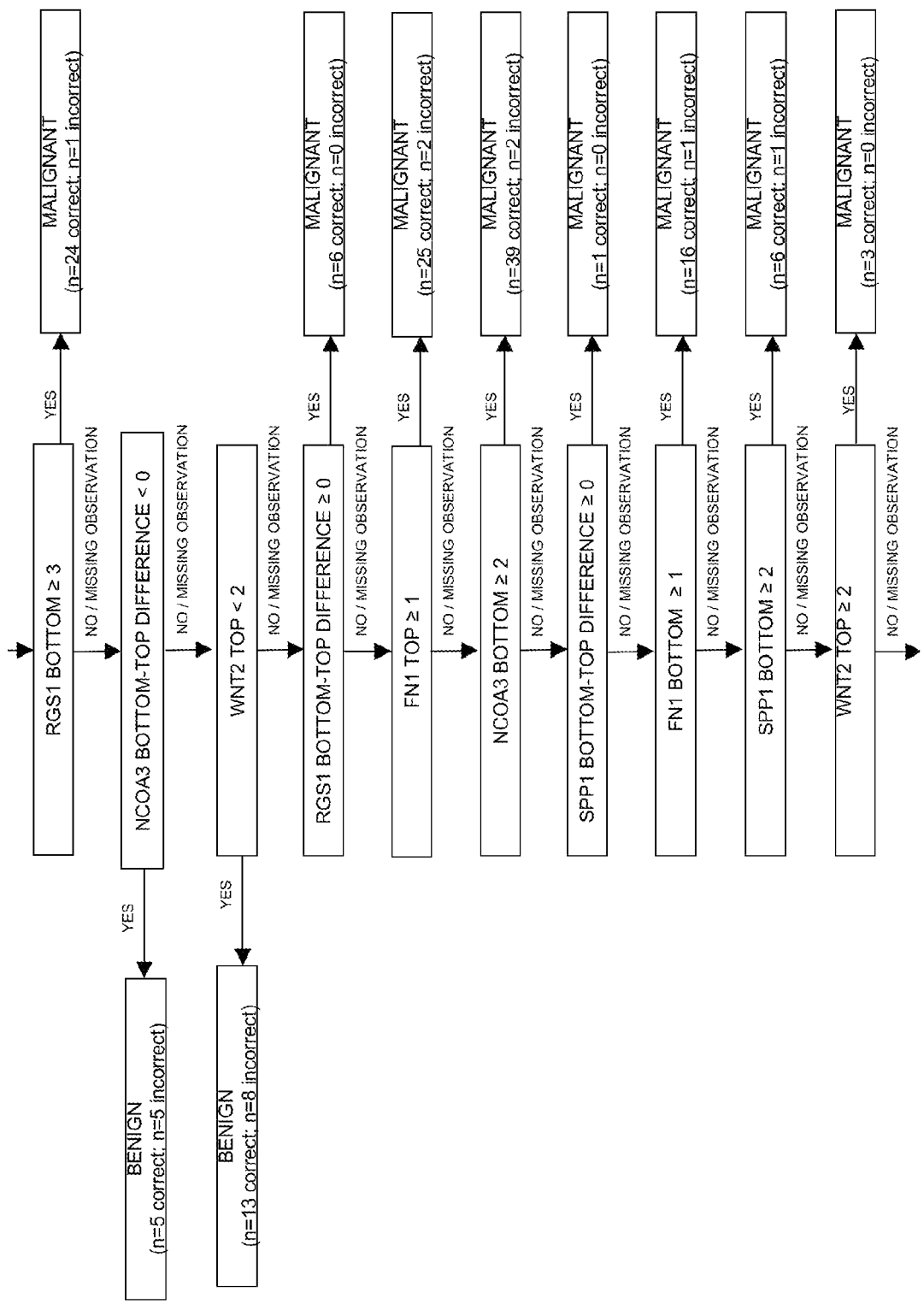
Fig. 23 sheet 2

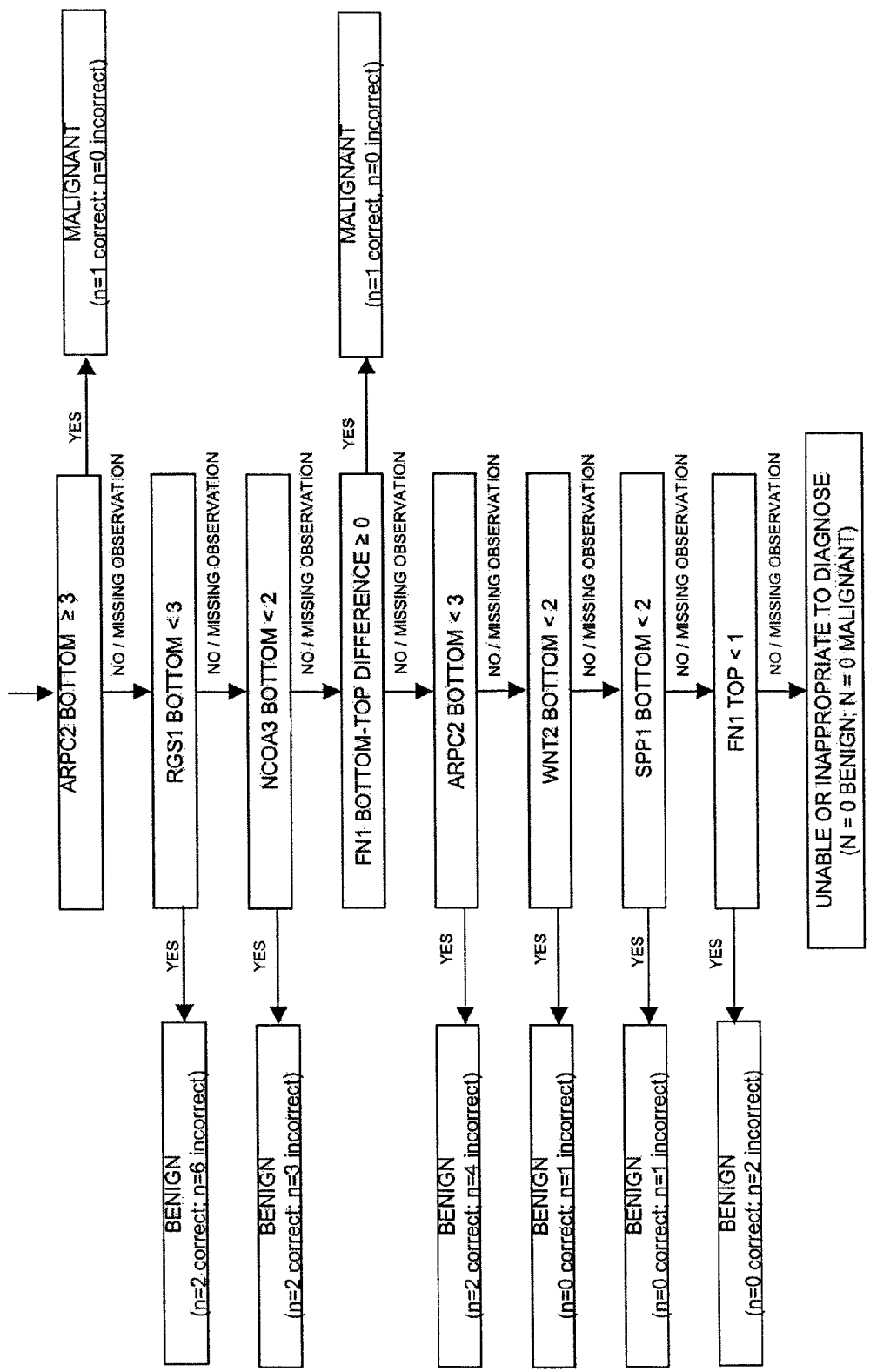
Fig.23 sheet 3

MOLECULAR DIAGNOSIS AND CLASSIFICATION OF MALIGNANT MELANOMA

CROSS-REFERENCES TO RELATED APPLICATIONS

The present application claims priority to U.S. Ser. No. 61/034,109, filed Mar. 5, 2008, herein incorporated by reference in its entirety.

The present application also incorporates by reference U.S. Ser. No. 60/842,730, filed Sep. 6, 2006, U.S. Ser. No. 60/908, 774, filed Mar. 29, 2007, 60/951,060, filed Jul. 20, 2007, and International Application No. PCT/US2007/077793, filed Sep. 6, 2007.

STATEMENT AS TO RIGHTS TO INVENTIONS MADE UNDER FEDERALLY SPONSORED RESEARCH OR DEVELOPMENT

This invention was made with Government support under NCI Grant No. RO1 CA114337 and CA122947. The Government has certain rights in this invention.

BACKGROUND OF THE INVENTION

Melanoma is the fifth most-common malignancy in the United States, the incidence of which is rising more rapidly than for any other form of cancer. Currently about one in seventy Americans is expected to develop melanoma during their lifetime. Melanoma is a malignant tumor of melanocytes (pigment cells). Although most melanomas arise in the skin, this cancer may also arise at mucosal surfaces or at other sites to which neural crest cells migrate. Melanomas that have not spread beyond their site of origin are highly curable as these early forms are thin lesions that have not invaded beyond the papillary dermis. The treatment of such early localized melanomas is surgical excision with margins proportional to the microstage of the primary lesion. Some melanomas that have spread to regional lymph nodes may be curable with wide excision of the primary tumor and removal of the involved regional lymph nodes. In contrast, more advanced forms of melanoma present a high risk of mortality from metastasis. When metastasis occurs, cancer cells may spread via the lymph nodes to distant sites such as the liver, lungs, or brain. The prognosis for patients in the later stages of this disease is poor with average survival from six to ten months.

The ability to cure early forms of melanoma coupled with its rapid conversion into an incurable metastatic form underscores the need for more accurate diagnostic methods for both the early detection of this disease and for better markers to serve as prognosticators of disease progression to afford better informed medical treatment strategies. Compounding the problem of devising appropriate therapeutic strategies based on accurate diagnoses and prognoses is the fact that physicians have found that melanoma frequently exhibits unpredictable clinical behavior. For instance, while the vertical thickness of the primary tumor is one of the most important prognostic factors determining survival, many patients with thick melanomas are free of metastasis while a small subset of patients with thin tumors die of their disease. Improved markers are therefore required to improve prognostic algorithms for newly diagnosed melanoma patients. Although extensively studied, no molecular factors are routinely used in the diagnosis and prognostic evaluation of melanoma patients. Such biomarkers would provide new avenues for early melanoma detection and would constitute targets for melanoma risk assessment, as well as targets for new drug development. The methods and compositions of this invention provide these additional tools for the care of patients with melanoma.

BRIEF SUMMARY OF THE INVENTION

Generally, the methods of this invention find particular use in diagnosing or providing a prognosis for melanoma by detecting the markers NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1 (FN1), and/or POU5F1/Oct3/4, which are differentially expressed (down or upregulated) in melanoma cells and correlate with melanoma progression. These markers can thus be used diagnostically to distinguish melanoma from benign nevi. They can also be used prognostically to determine the probability of overall survival, SLN status, relapse free survival, and disease specific survival. The markers can be used alone or in combination. In one embodiment, Wnt-2, ARPC2, SPP1, RGS1, and FN1 are used in a five marker diagnostic assay to distinguish benign nevi from melanoma. In another embodiment, NCOA3 and SPP1, and NCOA3, SPP1, and RGS1 are used in a two or three marker prognostic assay to determine the probability of overall survival, SLN status, relapse free survival, and disease specific survival. In a further embodiment, ARPC2, FN1, NCOA3, RGS1, SPP1, and WNT2 are used in a six marker diagnostic assay for melanoma. In another embodiment, RGS1, NCOA3, SPP1, and PHIP are used in a four marker prognostic assay for melanoma.

Diagnostic and prognostic kits comprising reagents for detecting one or more markers are provided. Also provided by the invention are methods for identifying compounds that are able to prevent or treat melanoma progression by modulating the markers NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4. Finally, therapeutic methods are provided, wherein melanoma is treated using siRNA molecules that specifically bind to one or more of the markers NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4.

In a first embodiment, this invention provides a method of diagnosing melanoma in a subject by contacting a biological sample from the subject with one or more than one reagent that specifically binds to a polypeptide marker selected from the group consisting of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 or one or more than one reagent that specifically binds to a nucleic acid marker selected from the group consisting of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 and then determining whether or not one or more than one marker is differentially expressed in the sample in order to provide a diagnosis for melanoma. In an aspect of this embodiment, the method includes determining whether or not two or more of the markers are differentially expressed in the sample, where the markers are independently selected. In another aspect of this embodiment, the reagent can be an antibody, which can be monoclonal. In another aspect of this embodiment, the reagent can be a nucleic acid, including an oligonucleotide or RT PCR primer set. In other aspects of this embodiment, the melanoma is primary melanoma or metastatic melanoma and the sample can be a skin biopsy. In further aspects of this embodiment, the diagnosis distinguishes between benign nevi versus malignant melanoma. In one particular aspect of this embodiment, the marker is Wnt-2. In some formats, the step of determining can be performed using an enzyme immunoassay, such as an ELISA or immunohistochemical assay. In other formats, the step of determining can be performed using FISH or CGH.

In a second embodiment, this invention provides a method of providing a prognosis for melanoma in a subject by contacting a biological sample from the subject with a reagent that specifically binds to a polypeptide marker selected from the group consisting of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 or a reagent that specifically binds to a nucleic acid marker selected from the group consisting of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 and then determining whether or not the marker is differentially expressed in the sample, thus providing a prognosis for melanoma. In an aspect of this embodiment, the method includes determining whether or not two or more of the markers are differentially expressed in the sample, where the markers are independently selected. In another aspect of this embodiment, the reagent can be an antibody, which can be monoclonal. In another aspect of this embodiment, the reagent can be a nucleic acid, including an oligonucleotide or RT PCR primer set. In other aspects of this embodiment, the melanoma is a primary melanoma or a metastatic melanoma and the sample can be a skin biopsy. In further aspects of this embodiment, the prognosis can be metastasis to regional lymph nodes, relapse, or death. In one particular aspect of this embodiment, the marker is NCOA3. In some formats, the step of determining can be performed using an enzyme immunoassay, such as an ELISA or immunohistochemical assay. In other formats, the step of determining can be performed using FISH or CGH.

In a third embodiment, this invention provides a method of identifying a compound that prevents or treats melanoma progression by contacting a compound with a sample containing a cell that expresses the NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 markers and then determining the functional effect of the compound on the marker, thus identifying a compound that prevents or treats melanoma. In some aspects of this embodiment, the method includes determining the functional effect of the compound on two or more of the markers, where the markers are each independently selected. In various aspects of the this embodiment, the compound can be a small molecule, siRNA, ribozyme, or antibody, which can be monoclonal. In some aspects of this embodiment, the melanoma is a primary melanoma or a metastatic melanoma.

In a fourth embodiment, the present invention provides a method of diagnosing or providing a prognosis for melanoma in a subject by (a) contacting a biological sample from the subject with reagents that specifically bind to the polypeptide or nucleic acid markers for: Wnt-2, osteopontin, ARPC2, RGS1, and Fibronectin 1, and then determining whether or not the markers are differentially expressed in the subject, thus providing a diagnosis or prognosis for melanoma. In some aspects, the method includes further detecting a polypeptide or nucleic acid marker, including markers for PHIP (pleckstrin homology domain interacting protein), WIF1, G1P3/IFN alpha inducible protein, MIP1 alpha, Bfl1/Bcl-2-related protein A1, or POU5F1/Oct3/4. In some formats, the step of determining can be performed using an enzyme immunoassay, such as an ELISA or immunohistochemical assay. In other formats, the step of determining can be performed using FISH or CGH.

In a fifth embodiment, the present invention provides a method of diagnosing or providing a prognosis for melanoma in a subject by (a) contacting a biological sample from the subject with reagents that specifically bind to two or more polypeptide or nucleic acid markers for: Wnt-2, osteopontin, ARPC2, RGS1, or Fibronectin 1, and then determining whether or not the markers are differentially expressed in the subject, where the markers are each independently selected, thus providing a diagnosis or prognosis for melanoma. In some aspects of this embodiment, the reagents bind to the polypeptide markers Wnt-2, osteopontin, ARPC2, RGS1, and Fibronectin 1. In other aspects of this embodiment, the reagents bind to the polypeptide markers osteopontin, NCOA3, and RGS1. In versions of this last aspect, the method further includes detecting a polypeptide or nucleic acid marker for Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, Fibronectin 1, or POU5F1/Oct3/4. In some formats, the step of determining can be performed using an enzyme immunoassay, such as an ELISA or immunohistochemical assay. In other formats, the step of determining can be performed using FISH or CGH.

In a sixth embodiment, the present invention provides a method of diagnosing or providing a prognosis for melanoma in a subject by (a) contacting a biological sample from the subject with reagents that specifically bind to the polypeptide or nucleic acid markers for: osteopontin, NCOA3, and RGS1, and then determining whether or not the markers are differentially expressed in the subject, thus providing a diagnosis or prognosis for melanoma. In an aspect of this embodiment, the method includes further detecting a polypeptide or nucleic acid marker, including markers for Wnt-2, PHIP (pleckstrin homology domain interacting protein), WIF1, ARPC2, G1P3/IFN alpha inducible protein, MIP1 alpha, Bfl1/Bcl-2-related protein A1, Fibronectin 1, and POU5F1/Oct3/4. In some formats, the step of determining can be performed using an enzyme immunoassay, such as an ELISA or immunohistochemical assay. In other formats, the step of determining can be performed using FISH or CGH.

In a seventh embodiment, the present invention provides a method of diagnosing or providing a prognosis for melanoma in a subject by (a) contacting a biological sample from the subject with reagents that specifically bind to two or more polypeptide or nucleic acid markers for: osteopontin, NCOA3, or RGS1, where the markers are independently selected, and then determining whether or not the markers are differentially expressed in the subject, thus providing a diagnosis or prognosis for melanoma. In an aspect of this embodiment, the reagents specifically bind to polypeptide or nucleic acid markers for osteopontin and NCOA3. In some formats, the step of determining can be performed using an enzyme immunoassay, such as an ELISA or immunohistochemical assay. In other formats, the step of determining can be performed using FISH or CGH.

In an eighth embodiment, the present invention provides a kit for diagnosing or providing a prognosis for melanoma in a subject. The kit can include a first container containing a first reagent that specifically binds to a polypeptide or nucleic acid marker, which can be a marker for: NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, and a second container containing a second reagent that specifically binds to a polypeptide or nucleic acid marker, which can be a marker for NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, where the second reagent binds a different marker than the first reagent. In one particular aspect of this embodiment, the first reagent specifically binds a NCOA3 marker and the second reagent binds an osteopontin marker. In another aspect of this embodiment, the first and the second reagent specifically binds a polypeptide or nucleic acid marker for Wnt-2, osteopontin, ARPC2, RGS1, or Fibronectin 1, where the second reagent binds a different marker than the first reagent. The kit can further contain additional reagents for performing detection by using an enzyme immunoassay, such as an ELISA or immunohistochemical assay. In other formats, the kit can further contain additional reagents for performing detection using FISH or CGH.

In a ninth embodiment, the present invention provides a method of diagnosing or providing a prognosis for melanoma in a subject by (a) administering to the subject a reagent that specifically binds to a polypeptide or nucleic acid marker for: NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, and then determining whether or not the marker is differentially expressed in the subject, thus providing a diagnosis or prognosis for melanoma. In some aspects of this embodiment, the method includes determining whether or not two or more of the markers are differentially expressed in the sample, where the markers are independently selected. In some aspects, the method of diagnosing or providing a prognosis includes the use of in vivo imaging with an antibody reagent, which can be monoclonal. Other imaging agents such as aptamers and speiglmers can be used as well.

In a tenth embodiment, the present invention provides a method of diagnosing melanoma in a subject by (a) contacting a biological sample from the subject with one or more than one reagent that specifically binds to one or more than one selected marker in the biological sample, where the markers include (i) the polypeptides Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and POU5F1/Oct3/4 or (ii) the nucleic acids encoding these polypeptides; and then (b) determining whether or not the selected marker is over expressed or under expressed in the sample, thus providing a diagnosis for melanoma in the subject. The method may also include the step of correlating elevated expression of the marker with a metastatic phenotype for cells in the sample. In various aspects of this embodiment, the reagent can be an antibody, nucleic acid, or RT PCR primer set. In further aspects, the sample is a skin biopsy. In a further aspect of this embodiment, at least one of the markers is selected from the polypeptides Wnt-2, NCOA3, PHIP, ARPC2, RGS1 and Fibronectin 1 or the nucleic acids encoding these polypeptides. In additional aspects, the diagnosis distinguishes between benign nevi versus malignant melanoma. In some formats, the step of determining can be performed using an enzyme immunoassay, such as an ELISA or immunohistochemical assay. In other formats, the step of determining can be performed using FISH or CGH.

In an eleventh embodiment, the present invention provides a method of providing a prognosis for melanoma in a subject by (a) contacting a biological sample from the subject with one or more than one reagent that specifically binds to one or more than one selected marker in the biological sample, where the markers include (i) the polypeptides Wnt-2, NCOA3, PHIP (pleckstrin homology domain interacting protein), osteopontin (SPP1), WIF1, ARPC2, G1P3/IFN alpha inducible protein, MIDI alpha, Bfl1/Bcl-2-related protein A1, RGS1, Fibronectin 1, and POU5F1/Oct3/4 or (ii) the nucleic acids encoding these polypeptides, and (b) determining whether or not the marker is over expressed or under expressed in the sample; thereby providing a prognosis for melanoma in the subject. In various aspects of this embodiment, the reagent can be an antibody, nucleic acid, or RT PCR primer set. In further aspects, the sample is a skin biopsy. In a further aspect of this embodiment, at least one of the markers is selected from the polypeptides NCOA3, osteopontin and RGS1 or the nucleic acids encoding these polypeptides. In additional aspects of this embodiment, the elevated expression of the one or more than one selected marker is correlated with a prognosis which can include metastasis to regional lymph nodes, relapse, and death. In some formats, the step of determining can be performed using an enzyme immunoassay, such as an ELISA or immunohistochemical assay. In other formats, the step of determining can be performed using FISH or CGH.

In a twelfth embodiment, the present invention provides a method of diagnosing or providing a prognosis for melanoma in a subject by (a) contacting a biological sample from the subject with two or more than two reagents that specifically bind to different selected markers in the sample, where the markers include (i) the polypeptides Wnt-2, osteopontin, ARPC2, RGS1, and Fibronectin 1 or (ii) the nucleic acids encoding the polypeptides, where the markers are each independently selected, and (b) determining whether or not the selected markers are over expressed or under expressed in the sample, thus diagnosing or providing a prognosis for melanoma in the subject. In an aspect of this embodiment, the reagents specifically bind to the polypeptide markers Wnt-2, osteopontin, ARPC2, RGS1, and Fibronectin 1, or to the nucleic acid markers encoding these polypeptides. In some formats, the step of determining can be performed using an enzyme immunoassay, such as an ELISA or immunohistochemical assay. In other formats, the step of determining can be performed using FISH or CGH.

In a thirteenth embodiment, the present invention provides a method of diagnosing or providing a prognosis for melanoma in a subject by (a) contacting a biological sample from the subject with reagents that specifically bind to selected polypeptide or nucleic acid markers in the sample, wherein the markers are osteopontin, NCOA3, and RGS1, and (b) determining whether or not the selected markers are over expressed or under expressed in the sample, thus diagnosing or providing a prognosis for melanoma in the subject. The method may further include the step of detecting a polypeptide or nucleic acid marker, including the markers for Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, Fibronectin 1, and POU5F1/Oct3/4. In some formats, the step of determining can be performed using an enzyme immunoassay, such as an ELISA or immunohistochemical assay. In other formats, the step of determining can be performed using FISH or CGH.

In a fourteenth embodiment, the present invention provides method of diagnosing or providing a prognosis for melanoma in a subject by (a) contacting a biological sample from the subject with two or more than two reagents that specifically bind different selected markers in the sample, where the markers include (i) the polypeptides osteopontin, NCOA3 and RGS1 or (ii) the nucleic acids encoding the polypeptides, and the markers are each independently selected; and (b) determining whether or not the markers are over expressed or under expressed in the sample, thus diagnosing or providing a prognosis for melanoma in the subject. In an aspect of this embodiment, the reagents specifically bind to the polypeptide markers osteopontin and NCOA3, or to the nucleic acid markers encoding osteopontin and NCOA3. In some formats, the step of determining can be performed using an enzyme immunoassay, such as an ELISA or immunohistochemical assay. In other formats, the step of determining can be performed using FISH or CGH.

In a fifthteenth embodiment, the present invention provides a kit for use in diagnosing or providing a prognosis for melanoma in a subject, where the kit contains (a) a first reagent that specifically binds a polypeptide or nucleic acid marker selected from the group consisting of Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and POU5F1/Oct3/4; and (b) a second reagent that specifically binds a polypeptide or nucleic acid marker selected from the group consisting of Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and POU5F1/Oct3/4, in which, the second reagent binds a different marker or different markers than the first reagent. In an aspect of this embodiment, the first reagent specifically binds a marker that includes the polypeptides Wnt-2, NCOA3, PHIP, ARPC2, RGS1 or Fibronectin 1, or the first reagent specifically binds a marker that includes the polypeptides NCOA3, osteopontin and RGS1. The kit can further contain additional reagents for performing detection by using an enzyme immunoassay, such as an ELISA or immunohistochemical assay. In other formats, the kit can further contain additional reagents for performing detection using FISH or CGH.

In a sixteenth embodiment, the present invention provides a method of diagnosing or providing a prognosis for melanoma in a subject by (a) administering to the subject one or more than one reagent that specifically binds to one or more than one selected marker in the subject, the markers including (i) the polypeptides Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and POU5F1/Oct3/4, or (ii) the nucleic acids encoding the polypeptides, and then, (b) determining whether or not the marker is over expressed or under expressed in the subject, thus providing a diagnosis or prognosis for melanoma.

In a seventeenth embodiment, the present invention provides a method of identifying a compound that prevents or treats melanoma progression by (a) contacting a compound with a sample comprising a cell that expresses a marker selected from the group consisting of Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, and (b) determining the functional effect of the compound on the marker, thus identifying a compound that prevents or treats melanoma. In an aspect of this embodiment, the method of identifying a compound includes determining the functional effect of the compound on two or more of the markers, where the markers are each independently selected.

In an eighteenth embodiment, the present invention provides a method of diagnosing melanoma in a subject by contacting a biological sample from the subject with reagents that each bind specifically to at least one selected marker in the biological sample, the selected markers comprising: (i) the polypeptides ARPC2, FN1, NCOA3, RGS1, osteopontin (SPP1), and WNT2, or (ii) the nucleic acids encoding the polypeptides, where there is at least one reagent binding to each marker, and (b) determining whether or not the selected marker is over expressed or under expressed in the sample, thus providing a diagnosis for melanoma in the subject. In an aspect of this embodiment, the reagents can be antibodies, which can be monoclonal. In some aspects, the antibodies can be labeled. In another aspect of this embodiment, the reagents can be nucleic acids, including an oligonucleotide or RT PCR primer set. In other aspects of this embodiment, the melanoma is primary melanoma or metastatic melanoma, and the sample can be a skin biopsy. In further aspects of this embodiment, the diagnosis distinguishes between benign nevi versus malignant melanoma. In some aspects, a determination is performed that correlates elevated expression of the selected markers with a metastatic phenotype for cells in the sample. In some formats, the step of determining can be performed using an enzyme immunoassay, such as an ELISA or immunohistochemical assay. In other formats, the step of determining can be performed using FISH or CGH.

In an nineteenth embodiment, the present invention provides a kit for use in diagnosing melanoma in a subject, the kit comprising reagents that each bind specifically to at least one selected marker in the biological sample, the selected markers comprising: (i) the polypeptides ARPC2, FN1, NCOA3, RGS1, osteopontin (SPP1), and WNT2, or (ii) the nucleic acids encoding the polypeptides, where there is at least one reagent binding to each marker. In an aspect of this embodiment, the reagents can be antibodies, which can be monoclonal. In some aspects, the antibodies can be labeled. In another aspect of this embodiment, the reagents can be nucleic acids, including an oligonucleotide or RT PCR primer set. The kit can further contain additional reagents for performing detection by using an enzyme immunoassay, such as an ELISA or immunohistochemical assay. In other formats, the kit can further contain additional reagents for performing detection using FISH or CGH.

In an twentieth embodiment, the present invention provides a method of diagnosing melanoma in a subject, the method comprising the steps of: (a) administering to the subject a reagents that each bind specifically to at least one selected marker in the subject, the selected markers comprising (i) the polypeptides ARPC2, FN1, NCOA3, RGS1, osteopontin (SPP1), and WNT2, or (ii) the nucleic acids encoding the polypeptides, where there is at least one reagent binding to each marker, and (b) determining whether or not the marker is over expressed or under expressed in the subject, thus providing a diagnosis for melanoma. In an aspect of this embodiment, the reagents can be antibodies, which can be monoclonal. In another aspect of this embodiment, the antibodies can be labeled.

In a twenty-first embodiment, the present invention provides a method of providing a prognosis for melanoma in a subject by (a) contacting a biological sample from the subject with reagents that each bind specifically to at least one selected marker in the biological sample, the selected markers comprising: (i) the polypeptides RGS1, NCOA3, osteopontin (SPP1), and PHIP, or (ii) the nucleic acids encoding the polypeptides, where there is at least one reagent binding to each marker, and (b) determining whether or not the selected marker is over expressed or under expressed in the sample; thereby providing a diagnosis for melanoma in the subject. In an aspect of this embodiment, the reagents can be antibodies, which can be monoclonal. In some aspects, the antibodies can be labeled. In another aspect of this embodiment, the reagents can be nucleic acids, including an oligonucleotide or RT PCR primer set. In other aspects of this embodiment, the melanoma is a primary melanoma or a metastatic melanoma, and the sample can be a skin biopsy. In further aspects of this embodiment, the prognosis can be metastasis to regional lymph nodes, relapse, or death. In some formats, the step of determining can be performed using an enzyme immunoassay, such as an ELISA or immunohistochemical assay. In other formats, the step of determining can be performed using FISH or CGH.

In a twenty-second embodiment, the present invention provides a kit for use in providing a prognosis for melanoma in a subject, the kit comprising reagents that each bind specifically to at least one selected marker in the biological sample, the selected markers comprising: (i) the polypeptides RGS1, NCOA3, osteopontin (SPP1), and PHIP, or (ii) the nucleic acids encoding the polypeptides, where there is at least one reagent binding to each marker. In an aspect of this embodiment, the reagents can be antibodies, which can be monoclonal. In some aspects, the antibodies can be labeled. In another aspect of this embodiment, the reagent can be nucleic acids, including an oligonucleotide or RT PCR primer set. The kit can further contain additional reagents for performing detection by using an enzyme immunoassay, such as an ELISA or immunohistochemical assay. In other formats, the kit can further contain additional reagents for performing detection using FISH or CGH.

BRIEF DESCRIPTION OF THE DRAWINGS

FIG. 8: Low-power (40×, panel A) and high-power (100×, panel B) photomicrographs of Wnt-2 immunostaining in a compound melanocytic nevus, showing intense staining in the intraepidermal nevus nests, with diminished staining in subepidermal and dermal nests.

FIG. 16. Diagnostic algorithm utilized for the training and validation sets combining marker intensity scores as well as top-to-bottom differences. For each diagnostic statement in the algorithm the number of correct and incorrect observations in the training set are included.

FIG. 23. Diagnostic algorithm using both staining intensity scores and top-to-bottom differences for six-gene diagnostic assay for melanoma.

DETAILED DESCRIPTION OF THE INVENTION

Introduction

Figure 1:
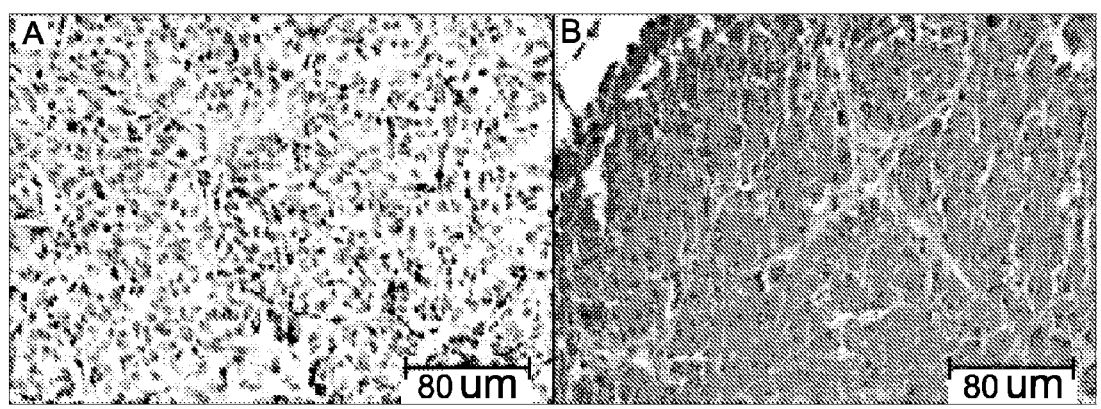
FIG. 1: Photomicrographs of primary melanoma demonstrating absent (panel A) and intense (panel B) NCOA3 immunostaining.

Despite intense investigation, no molecular markers are in routine use for the diagnosis and prognostic evaluation of melanoma patients. A prerequisite toward the development of such markers is knowledge of genes that are differentially expressed in melanoma cells.

We determined that the genes Wnt-2, NCOA3, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and POU5F1/Oct3/4 show differential expression in melanoma.

As detailed below, these genes display distinctive expression patterns that are characteristic of different aspects of melanoma progression, and thus, can be used to diagnose and prognose different stages of this cancer. For instance, our data reveals that NCOA3 is a good indicator of melanoma metastasis to regional lymph nodes, disease relapse, and death, while Wnt-2 can be a diagnostic marker for benign nevi versus malignant melanoma. Furthermore, our data indicates that SPP1 is overexpressed in melanomas as compared with benign nevi. Our data also reveals that NCOA3 may be used as a predictor of a subset of desmoplastic melanoma that will metastasize to regional lymph nodes. These results reveal that the markers disclosed herein may be used alone or in combination to provide more definitive diagnostic and prognostic tools for the clinician.

In addition, the proteins encoded by these genes are differentially expressed in melanomas.

Accordingly, this invention provides methods for the diagnosis and prognostic evaluation of melanoma based on the differential expression of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, and/or POU5F1/Oct3/4 in melanoma cells. The markers can be used alone or in combinations of two or more, or as a panel or markers. In one embodiment, a six marker assay based on the differential expression of ARPC2, FN1, NCOA3, RGS1, osteopontin (SPP1), and WNT2 is utilized for the diagnosis of melanoma. In another embodiment, a four marker assay based on the differential expression of RGS1, NCOA3, osteopontin (SPP1), and PHIP is utilized for providing a prognosis of melanoma. The invention also provides kits for diagnosis or prognosis of melanoma comprising one or more reagents for detecting the markers. The invention also provides therapeutic siRNAs complementary to a sequence of one or more of the markers for treatment of melanoma.

Definitions

Melanoma is a form of cancer that begins in melanocytes, the cells that produce pigment. While frequently occurring on the skin, melanoma can also occur in the eye and rarely in the membranes of the nasal passages, oral, pharyngeal mucosa, vaginal and anal mucosa. The American Joint Committee on Cancer (AJCC) has devised a system for classifying melanomas into 4 stages (with many substages) based on pathological criteria and survival rates. Melanoma may arise from moles or benign nevi on the skin and progress through the stages defined by the AJCC staging system. See, e.g., *Harrison's Principles of Internal Medicine*, Kasper et al., $16^{th}$ ed., 2005, for additional background.

The term "marker" refers to a molecule (typically protein, nucleic acid, carbohydrate, or lipid) that is expressed in the cell, expressed on the surface of a cancer cell or secreted by a cancer cell in comparison to a normal cell, and which is useful for the diagnosis of cancer, for providing a prognosis. Such markers are molecules that are differentially expressed, e.g., overexpressed or underexpressed in a melanoma or other cancer cell in comparison to a normal cell, for instance, 1-fold over/under expression, 2-fold over/under expression, 3-fold over/under expression or more in comparison to a normal cell, a nevi, or a primary cancer (vs. metastases). Further, a marker can be a molecule that is inappropriately synthesized in the cancer cell, for instance, a molecule that contains deletions, additions or mutations in comparison to the molecule expressed on a normal cell.

Markers may be used singly or in combination with other markers for any of the uses, e.g., diagnosis or prognosis of melanoma, as disclosed herein.

As used herein, "a melanoma evaluation marker" refers to a marker differentially expressed in melanoma cells and refers equivalently to a polypeptide or nucleic acid which encodes the polypeptide or any portion of the polypeptide.

"Biological sample" includes sections of tissues such as biopsy and autopsy samples, and frozen sections taken for histologic purposes. Such samples include skin samples, samples of muscosal surfaces, blood and blood fractions or products (e.g., serum, plasma, platelets, red blood cells, and the like), sputum, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse, rabbit.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., skin, mucosal surface, etc.), the size and type of the tumor (e.g., solid or suspended, blood or ascites), among other factors. Representative biopsy techniques include, but are not limited to, excisional biopsy, incisional biopsy, needle biopsy, surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally contains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "overexpress," "overexpression" or "overexpressed" interchangeably refer to a protein or nucleic acid that is transcribed or translated at a detectably greater level, usually in a cancer cell, in comparison to a normal cell, a nevi, or a primary cancer. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell. Overexpression can also include any expression in a sample cell when compared to the absence of expression in a normal cell.

The terms "underexpress," "underexpression" or "underexpressed" interchangeably refer to a protein or nucleic acid that is transcribed or translated at a detectably lower level, usually in a cancer cell, in comparison to a normal cell, a nevi, or a primary cancer. The term includes underxpression due to transcription, post transcriptional processing, translation, post-translational processing, cellular localization (e.g., organelle, cytoplasm, nucleus, cell surface), and RNA and protein stability, as compared to a normal cell. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% etc. in comparison to a normal cell. In certain instances, underexpression is 1-fold, 2-fold, 3-fold, 4-fold or more lower levels of transcription or translation in comparison to a normal cell. Underexpression can also include the absence of expression in a sample cell when compared to any expression in a normal cell.

"Therapeutic treatment" and "cancer therapies" refers to chemotherapy, hormonal therapy, radiotherapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

An "antisense" polynucleotide is a polynucleotide that is substantially complementary to a target polynucleotide and has the ability to specifically hybridize to the target polynucleotide.

Ribozymes are enzymatic RNA molecules capable of catalyzing specific cleavage of RNA. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, which is incorporated herein by reference in its entirety). Ribozyme molecules designed to catalytically cleave target mRNA transcripts can also be used to prevent translation of subject target mRNAs.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% form amide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

In one embodiment, the antibody is conjugated to an "effector" moiety. The effector moiety can be any number of molecules, including labeling moieties such as radioactive labels or fluorescent labels.

The amino acid or nucleotide sequences of representative markers for use in the present invention are available for online retrieval from any suitable source, as will be understood by those with skill in the art with reference to this disclosure. For example, the following amino acid and nucleotide sequences, which are incorporated herein by reference, are available from the NCBI website using the Entrez search engine.

NCOA3 refers to a member of the steroid receptor coactivator protein family in humans. Accession numbers for representative nucleic acids encoding NCOA3 include: NM_008679, BC092516, and BC088343, among others. Accession numbers for representative NCOA3 proteins include: CAI42141, CAC17693, CAB40662, AAH88343, and NP_032705, among others.

Wnt-2 refers to a member of a family of extracellular proteins that can bind to cell surface receptors to activate a signaling pathway in cells. Accession numbers for representative nucleic acids encoding Wnt-2 include: NM_003391 and NM_023653, among others. Accession numbers for representative Wnt-2 proteins include: NP_004176, NP_078613, and AAF30299, among others.

PHIP (pleckstrin homology domain interacting protein) refers to proteins which were originally identified as proteins which bind to the pleckstrin homology (PH) domain on insulin receptor substrate-1 (IRS-1) protein, which is a substrate for phosphorylation by the insulin receptor tyrosine kinase. See, e.g., Farhang-Fallah, J. et al., *J. Biol. Chem.*, 275: 40492-40497 (2000). Accession numbers for representative nucleic acid and protein sequences for PHIP include: AAH08909, NP060404, XP999437, and NM017934, among others.

Osteopontin, or SPP1 (secreted phosphoprotein 1), refers to a family of phosphorylated glycoproteins that are abundant in bone mineral matrix and accelerates bone regeneration and remodeling. It is also produced in other tissues and plays a role in the regulation and progression of many diseases, as by enhancing the invasive and proteolytic capabilities of tumor cells. Accession numbers for representative protein sequences for osteopontin include: AAA62729, AAA59974, CAA 40091, AAC28619, and NM_000582, among others.

Accession numbers for representative sequences for WIF1, ARPC2, G1P3/IFN alpha inducible protein, MIP1 alpha, Bfl1/Bcl-2-related protein A1, RGS1, Fibronectin 1, or POU5F1/Oct3/4 are as follows: WIF1: NM_007191; ARPC2: NM_152862 and NM_005731; GIP3 aka IFI6: NM_022872, NM_002038, and NM_022873; Mip-1 alpha aka CCL3: NM_002983; Bfl-1 aka BCL2A1: NM_004049; RGS1: NM_002922; FN1 (fibronectin 1): NM_212475, NM_054034, NM 212476, NM_002026, NM_212474, NM_212478, and NM_212482; and POU5F1: NM_002701 and NM_203289.

The nucleic acids encoding NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, particularly NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a marker protein such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, e.g., a chemical or phenotypic effect such as altered transcriptional activity of NCOA3 or altered activity of the Wnt-2 signaling pathway and the downstream effects of such proteins on cellular metabolism and growth. A functional effect therefore includes ligand binding activity, transcriptional activation or repression, the ability of cells to proliferate, expression in cells during melanoma progression, and other characteristics of melanoma cells. "Functional effects" include in vitro, in vivo, and ex vivo activities.

By "determining the functional effect" is meant assaying for a compound that increases or decreases a parameter that is indirectly or directly under the influence of a marker such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. Determination of the functional effect of a compound on melanoma cell progression can also be performed using assays known to those of skill in the art such as metastasis of melanoma cells by tail vein injection of melanoma cells in mice. The functional effects can be evaluated by many means known to those skilled in the art, e.g., microscopy for quantitative or qualitative measures of alterations in morphological features, measurement of changes in RNA or protein levels for other genes expressed in melanoma cells, measurement of RNA stability, identification of downstream or reporter gene expression (CAT, luciferase, GFP and the like), e.g., via chemiluminescence, fluorescence, colorimetric reactions, antibody binding, inducible markers, etc.

"Inhibitors," "activators," and "modulators" of the markers are used to refer to activating, inhibitory, or modulating molecules identified using in vitro and in vivo assays of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4. Inhibitors are compounds that, e.g., bind to, partially or totally block activity, decrease, prevent, delay activation, inactivate, desensitize, or down regulate the activity or expression of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, e.g., antagonists. "Activators" are compounds that increase, open, activate, facilitate, enhance activation, sensitize, agonize, or up regulate activity of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, e.g., agonists. Inhibitors, activators, or modulators also include genetically modified versions of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing melanoma markers such as NCOA3, Wnt-2, PHIP (pleckstrin homology domain interacting protein), osteopontin (SPP1), WIF1, ARPC2, GIP3/IFN alpha inducible protein, MIP1 alpha, Bfl1/Bcl-2-related protein A1, RGS1, Fibronectin 1, or POU5F1/Oct3/4 in vitro, in cells, or cell extracts, applying putative modulator compounds, and then determining the functional effects on activity, as described above.

Samples or assays comprising melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 that are treated with a potential activator, inhibitor, or modulator are compared to control samples without the inhibitor, activator, or modulator to examine the extent of inhibition. Control samples (untreated with inhibitors) are assigned a relative protein activity value of 100% Inhibition of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 is achieved when the activity value relative to the control is about 80%, preferably 50%, more preferably 25-0%. Activation of melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate melanoma markers such as NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Diagnostic and Prognostic Methods

The present invention provides methods of diagnosing, or providing a prognosis, for melanoma by detecting the expression of markers differentially expressed in melanoma cells at different stages of malignancy. Diagnosis involves determining the expression level of a NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 polypeptide or nucleic acid in a patient or patient sample and then comparing the expression level to a baseline or range. Typically, the baseline value is representative of expression levels of the polypeptide or nucleic acid in a healthy person not suffering from melanoma, as measured using a biological sample such as a skin biopsy. Variation of levels of a polynucleotide or nucleic acid of the invention from the baseline range (either up or down) indicates that the patient has a cancer or is at risk of developing a cancer, depending on the marker used. In the case of NCOA3, Wnt-2, PHIP (pleckstrin homology domain interacting protein), osteopontin (SPP1), ARPC2, G1P3/IFN alpha inducible protein, MIP1 alpha, Bfl1/Bcl-2-related protein A1, RGS1, Fibronectin 1, or POU5F1/Oct3/4, overexpression would be consistent with a diagnosis of melanoma. In the case of Wif1, underexpression would be consistent with a diagnosis of melanoma.

As used herein, the term "providing a prognosis" refers to providing a prediction of the probable course and outcome of melanoma. The methods can also be used to devise a suitable therapy for melanoma treatment, e.g., by indicating whether or not the melanoma is still at a benign stage or if the melanoma had advanced to a stage where aggressive therapy would be required.

Antibody reagents can be used in assays to detect expression levels of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 in patient samples using any of a number of immunoassays known to those skilled in the art. Monoclonal antibody reagents suitable for use in detecting the expression of NCOA3 are disclosed in U.S. Application No. 61/033,663, filed on Mar. 4, 2008. Moreover, monoclonal antibody reagents suitable for use in detecting the expression of Wnt-2 are disclosed in U.S. Application No. 61/033,641, filed on Mar. 4, 2008. These references are hereby incorporated by reference for all purposes.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.*, 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical (IHC) assays; capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis*, 18:2184-93 (1997); Bao, *J. Chromatogr. B. Biomed. Sci.*, 699:463-80 (1997). Liposome immunoassays, such as flow-injection liposome immunoassays and liposome immunosensors, are also suitable for use in the present invention. See, e.g., Rongen et al., *J. Immunol. Methods*, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody to proteins can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman®assays available from, e.g., Applied Biosystems, can be used to detect nucleic acids and variants thereof. In other embodiments, qPCR and nucleic acid microarrays can be used to detect nucleic acids. Reagents that bind to selected cancer biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, fluorescent in situ hybridization (FISH), comparative genomic hybridization (CGH), and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

FISH and CGH are methods for analyzing genomic DNA for unbalanced genetic alterations. In brief, genomic DNA from a test sample (e.g., melanoma cells) is labeled (e.g., a red fluorescent label) and mixed with normal genomic DNA labeled with another color (e.g., a green fluorescent label) and the mixture is hybridized to a normal human metaphase spread, tissue preparation, or other reference standard. Regions of chromosomal imbalance (increased or decreased copy number) in the melanoma sample are located or mapped relative to the normal metaphase chromosomes as increases or decreases in the green to red fluorescence ratio. Detailed protocols for performing FISH or CGH are available in the art, for example, in *Molecular Cytogenetics: Protocols and Applications*, edited by Yao-Shan Fan, Humana Press, 2002; Cancer Cytogenetics: Methods and Protocols, edited by John Swansbury, Humana Press, 2003.

In performing FISH and CGH, a chromosomal sample is prepared by depositing cells, either as single cell suspensions or as a tissue preparation, on solid supports such as glass slides and fixed by choosing a fixative which provides the best spatial resolution of the cells and the optimal hybridization efficiency. In situ hybridization generally entails the following principal steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization; and (5) detection of the hybridized nucleic acid fragments. In some cases, it is necessary to block the hybridization capacity of repetitive sequences. For such purposes, human genomic DNA can be used as an agent to block such hybridization. For the hybridization, a test probes that hybridizes to a chromosomal region of interest (e.g., one or more of the markers disclosed herein) is labelled with one dye, and a control probe that hybridizes to a different region is labelled with a second dye. A nucleic acid that hybridizes to a stable portion of the chromosome of interest, such as the centromere region, is often useful as the control probe. By using such controls, differences between efficiency of hybridization from sample to sample can be accounted for. If multiple test markers are used in a single hybridization, each can be labeled with a separately distinguishable label.

Given the sensitivity of FISH and CGH methods, a variety of test samples may be used. Paraffin embedded tumor sections can be used, as can fresh or frozen material. Other types of preparations include those derived from uncultured primary tumors (see, e.g., Kallioniemi, A. et al., *Cytogenet. Cell Genet.* 60:190-193 (1992)). For instance, blood samples or small biopsy tissue samples from tumors can be used. (see, e.g., Kallioniemi, A. et al., *Cytogenet. Cell Genet.* 60:190-193 (1992)). Small numbers of cells obtained from aspiration biopsy or cells in bodily fluids (e.g., blood, urine, sputum and the like) can also be analyzed.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.,* 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In some embodiments, melanoma in a patient may be diagnosed or otherwise evaluated by visualizing expression in situ of one or more of the gene sequences or polypeptides disclosed herein. Those skilled in the art of visualizing the presence or expression of molecules including nucleic acids, polypeptides and other biochemicals in living patients will appreciate that the gene expression information described herein may be utilized in the context of a variety of visualization methods. Such methods include, but are not limited to, single-photon emission-computed tomography (SPECT) and positron-emitting tomography (PET) methods. See, e.g., Vassaux and Groot-wassink, "In Vivo Noninvasive Imaging for Gene Therapy," J. Biomedicine and Biotechnology, 2: 92-101 (2003); Turner, J., Smyth, P., Fallon, J. F., Kennedy, J. L., Potkin, S. G., FIRST BIRN (2006). Imaging and genetics in schizophrenia. Neuroinformatics, in press.

PET and SPECT imaging shows the chemical functioning of organs and tissues, while other imaging techniques—such as X-ray, CT and MRI—show structure. The use of PET and SPECT imaging is useful for identifying and monitoring the development of melanoma. In some instances, the use of PET or SPECT imaging allows diseases to be detected years earlier than the onset of symptoms. The use of small molecules for labelling and visualizing the presence or expression of polypeptides and nucleotides has had success, for example, in visualizing proteins in the brains of Alzheimer's patients, as described by, e.g., Herholz K et al., *Mol Imaging Biol.,* 6(4): 239-69 (2004); Nordberg A, *Lancet Neurol.,* 3(9):519-27 (2004); *Neuropsychol Rev.,* Zakzanis K K et al., 13(1):1-18 (2003); Kung M P et al, *Brain Res.,* 1025(1-2):98-105 (2004); and Herholz K, *Ann Nucl Med.,* 17(2):79-89 (2003). Antibodies and nucleic acid probes are also useful.

The differentially expressed genes disclosed herein, or their encoded peptides, or fragments thereof, can be used in the context of PET and SPECT imaging applications. After modification with appropriate tracer residues for PET or SPECT applications, molecules which interact or bind with the nucleic acid markers or with any polypeptides encoded by those transcripts may be used to visualize the patterns of gene expression and facilitate diagnosis and prognosis as described herein. Similarly, if the encoded polypeptides encode enzymes, labeled molecules which interact with the products of catalysis by the enzyme may be used for the in vivo imaging and diagnostic application described herein.

Compositions and Kits

The invention provides compositions and kits for practicing the assays described herein using antibodies specific for the polypeptides or nucleic acids specific for the polynucleotides of the invention.

Kits for carrying out the diagnostic assays of the invention typically include, in suitable container means, a probe that comprises an antibody or nucleic acid sequence that specifically binds to the marker polypeptides or polynucleotides of the invention, and a label for detecting the presence of the probe. The kits may include several antibodies or polynucleotide sequences encoding polypeptides of the invention, e.g., a first antibody and/or second and/or third and/or additional antibodies that recognize NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4.

The container means of the kits will generally include at least one vial, test tube, flask, bottle, syringe and/or other container into which a first antibody specific for one of the polypeptides or a first nucleic acid specific for one of the polynucleotides of the present invention may be placed and/or suitably aliquoted. Where a second and/or third and/or additional component is provided, the kit will also generally contain a second, third and/or other additional container into which this component may be placed. Alternatively, a container may contain a mixture of more than one antibody or nucleic acid reagent, each reagent specifically binding a different marker in accordance with the present invention. The kits of the present invention will also typically include means for containing the antibody or nucleic acid probes in close confinement for commercial sale. Such containers may include injection and/or blow-molded plastic containers into which the desired vials are retained.

The kits may further comprise positive and negative controls, as well as instructions for the use of kit components contained therein, in accordance with the methods of the present invention.

In Vivo Imaging

The various markers of the invention also provide reagents for in vivo imaging such as, for instance, the imaging of metastasis of melanoma to regional lymph nodes using labeled reagents that detect NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 protein or nucleic acid. In vivo imaging techniques may be used, for example, as guides for surgical resection or to detect the distant spread of melanoma. For in vivo imaging purposes, reagents that detect the presence of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4, such as antibodies, may be labeled with a positron-emitting isotope (e.g., 18F) for positron emission tomography (PET), gamma-ray isotope (e.g., 99 mTc) for single photon emission computed tomography (SPECT), a paramagnetic molecule or nanoparticle (e.g., Gd3+ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

Furthermore, such reagents may include a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. Nos. 4,452,720, 5,227,487, and 5,543,295.

Other fluorescent labels suitable for use in the practice of this invention include a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. A cargo portion C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. Nos. 6,080,852, 6,025,505, 5,936,087, 5,750,409. A cargo portion C may include a cyanine dye, such as, for example, Cy3, Cy3B, Cy3.5, Cy5, Cy5.5, Cy7. Phosphorescent compounds including porphyrins, phthalocyanines, polyaromatic compounds such as pyrenes, anthracenes and acenaphthenes, and so forth, may also be used.

Reagents such as antibodies may include a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, radioactive isotopes of Lu, and others.

Methods to Identify Compounds

A variety of methods may be used to identify compounds that prevent or treat melanoma progression. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4 can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce the expression of NCOA3, Wnt-2, PHIP (pleckstrin homology domain interacting protein), osteopontin (SPP1), WIF1, ARPC2, G1P3/IFN alpha inducible protein, MIP1 alpha, Bfl1/Bcl-2-related protein A1, RGS1, Fibronectin 1, or POU5F1/Oct3/4.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds is possible using the integrated systems of the invention.

Methods to Inhibit Marker Protein Expression Using Nucleic Acids

A variety of nucleic acids, such as antisense nucleic acids, siRNAs or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

The following examples are offered to illustrate, but not to limit the invention.

Example 1

Correlation of NCOA3 Overexpression with Melanoma Outcome

NCOA3 expression was assessed using immunohistochemical analysis of a melanoma tissue microarray (TMA) containing primary melanomas from 343 patients with defined histology and follow up. The impact of the presence or absence of various prognostic factors on relapse-free (RFS) and disease-specific (DSS) survival of melanoma patients was assessed using Cox regression and Kaplan-Meier analysis. The impact of presence or absence of various factors on sentinel lymph node (SLN) metastasis was assessed using logistic regression analysis.

As our results below demonstrate, increasing degree of NCOA3 expression was significantly predictive of SLN metastasis (P=0.013) and the mean number of SLN metastases (P=0.031). Kaplan-Meier analysis demonstrated a significant association between NCOA3 overexpression and reduced RFS (P=0.021) and DSS (P=0.030). Logistic regression analysis revealed increasing degree of NCOA3 expression to be an independent predictor of SLN status (P=0.017).

Multivariate Cox regression analysis showed the independent impact of NCOA3 expression on RFS (P=0.0095) and DSS (P=0.021). NCOA3 was the most powerful factor predicting DSS, outperforming tumor thickness and ulceration. Thus, these results identify NCOA3 as a novel, independent marker of melanoma outcome, with a significant impact on SLN metastasis, RFS and DSS.

Characterization and Construction of Melanoma TMA

We constructed a TMA of 343 primary melanomas with at least two years of follow up, documented relapse, or having undergone SLN biopsy. The demographic breakdown of the cohort appears in Table 1. Of the 343 patients, 259 had undergone SLN biopsy, thus providing information regarding SLN status. The criteria for undergoing SLN biopsy include the following: melanoma >1.0 mm in thickness, or presence of any of the following histologic factors in melanomas under 1.0 mm thick: Clark level IV or V, ulceration, vascular involvement, microsatellites, extensive regression (covering greater than 50% of the diameter of the tumor), or inadequate biopsy (partial biopsy showing melanoma transected at the base). The mean follow up of this cohort was 49 months, with a median follow up of 45 months. The TMAs were constructed as previously described by taking 1.0 mm in diameter tissue cores from the paraffin block (see Kashani-Sabet M. et al., *J Clin Oncol*, 22:617-623, 2004; Kononen J. et al., *Nat Med* 4: 844-847, 1998.

TABLE 1

Summary of patient demographics

| Demographic Variable | Number (%, if applicable) |
| --- | --- |
| Age (Median) | 53 |
| Male gender | 227 (66.2) |
| Anatomical location | |
| Head and neck | 60 (17.5) |
| Trunk | 137 (39.9) |
| Extremity | 146 (42.6) |
| Histologic tumor type | |
| Superficial spreading melanoma | 159 (46.4) |
| Nodular melanoma | 121 (35.3) |
| Acral melanoma | 19 (5.5) |
| Lentigo maligna melanoma | 11 (3.2) |
| Desmoplastic melanoma | 9 (2.6) |
| Melanoma not otherwise classified | 24 (7.0) |
| Tumor thickness | |
| T1 ($\leq$1.0 mm) | 22 (6.4) |
| T2 (1.01-2.0 mm) | 110 (32.1) |
| T3 (2.01-4.0 mm) | 97 (28.3) |
| T4 ($\geq$4.0 mm) | 114 (33.2) |

Immunohistochemistry

Slides were deparaffinized and rehydrated in xylene, then microwaved in 10 mM citrate buffer. Endogenous peroxidase activity was blocked with 3% hydrogen peroxide, and the slides sequentially incubated with Avidin and Biotin blocking reagents. The primary antibody, mouse monoclonal anti-NCOA3 IgG (Abcam #ab14139) was then added at a 1:10 dilution and incubated for 60 min at room temperature. Biotinylated horse anti-mouse IgG antibody (Vector Laboratories, Burlingame, Calif.) was used as a secondary antibody for amplification, followed by incubation with ABC-HRP (Vector Laboratories) for 30 min, and DAB/Hydrogen peroxide solution (Sigma).

Evaluation of Immunohistochemical Staining

The regions of most intense staining were scored for each tissue array core. Expression of NCOA3 protein was graded using the following scale: no staining (0), weak staining (1), moderate staining (2), and intense staining (3). The arrays were scored by a pathologist blinded to the identity of the cases, and each score was replicated by a separate, independent scoring trial. A consensus score was determined for the few instances of discrepant scoring across replicated trials. Specificity controls for NCOA3 staining included breast tumor, melanoma cell lines (LOX and FEM) and melanoma tissue sections. Positive controls included breast tumor sections as well as LOX and FEM cells, while negative controls included tonsil tissue and the breast carcinoma cell line T47D. The negative control used for immunohistochemistry included the use of phosphate buffered saline instead of primary antibody, with all other experimental conditions kept constant.

Statistical Analyses

Statistical methods used to assess the significance of various prognostic factors on melanoma outcome were previously described. (see Kashani-Sabet M. et al., *J Clin Oncol*, 22:617-623, 2004; Kashani-Sabet M. et al., *J Clin Oncol*, 20:1826-1831, 2002; Kashani-Sabet, M. et al., *Arch Dermatol.* 137:1169-1173, 2001. For both RFS and DSS, the definition of high NCOA3 scores (defined as a score of 2 or 3) was originally selected on the basis of the best cutoffs for predictive value of DSS on Kaplan-Meier analysis, and the same cutoffs were uniformly and consistently used in all subsequent univariate and multivariate analyses of RFS and DSS. The association between high NCOA3 expression and RFS or DSS was assessed using the Fisher exact test and both univariate and multivariate Cox regression. For SLN status, the best cutoffs were determined to be a score of 0 vs. 1 or 2 vs. 3 on the basis of the results of univariate logistic regression analysis, and the same cutoffs were uniformly and consistently used for all subsequent analyses examining SLN status. The association between increasing NCOA3 expression and SLN metastasis was assessed using Chi-square analysis and both univariate and multivariate logistic regression. The association between increasing NCOA3 expression and mean SLN count was assessed using the analysis of variance (ANOVA) and the directional Le test. With the exception of this directional analysis, all P values reported are two sided. In addition to the prognostic factors analyzed by the AJCC, the following factors were included in the dataset: mitotic rate, tumor vascularity, presence or absence of microsatellites, vascular involvement, and regression. The coding for clinical or pathological attributes was performed as previously described (see Kashani-Sabet M. et al., *J Clin Oncol*, 22:617-623, 2004).

Results

Given our cDNA microarray results suggesting differential expression of the NCOA3 gene in metastatic melanomas when compared with unrelated primary tumors, we aimed to examine the prognostic impact of NCOA3 expression at the protein level in a TMA containing 343 primary melanoma cores. NCOA3 expression was analyzed using a commercially available monoclonal antibody targeting human NCOA3 (mouse monoclonal anti-NCOA3 IgG (Abcam #ab14139)), and scored by an observer blinded to patient outcomes.

NCOA3 expression was absent in 20 (8%, FIG. 1A) and intense (score of 3) in 111 (32.4%, FIG. 1B) of the 343 cores examined. Expression of NCOA3 did not significantly correlate with histologic subtype of melanoma (data not shown), with the possible exception of desmoplastic melanomas, in which only one primary tumor exhibited intense staining. In addition, NCOA3 expression did not correlate with several known histologic prognostic factors for melanoma, such as tumor thickness, ulceration, Clark level, mitotic rate, vascular involvement, microsatellites, or tumor vascularity (data not shown).

Figure 2:
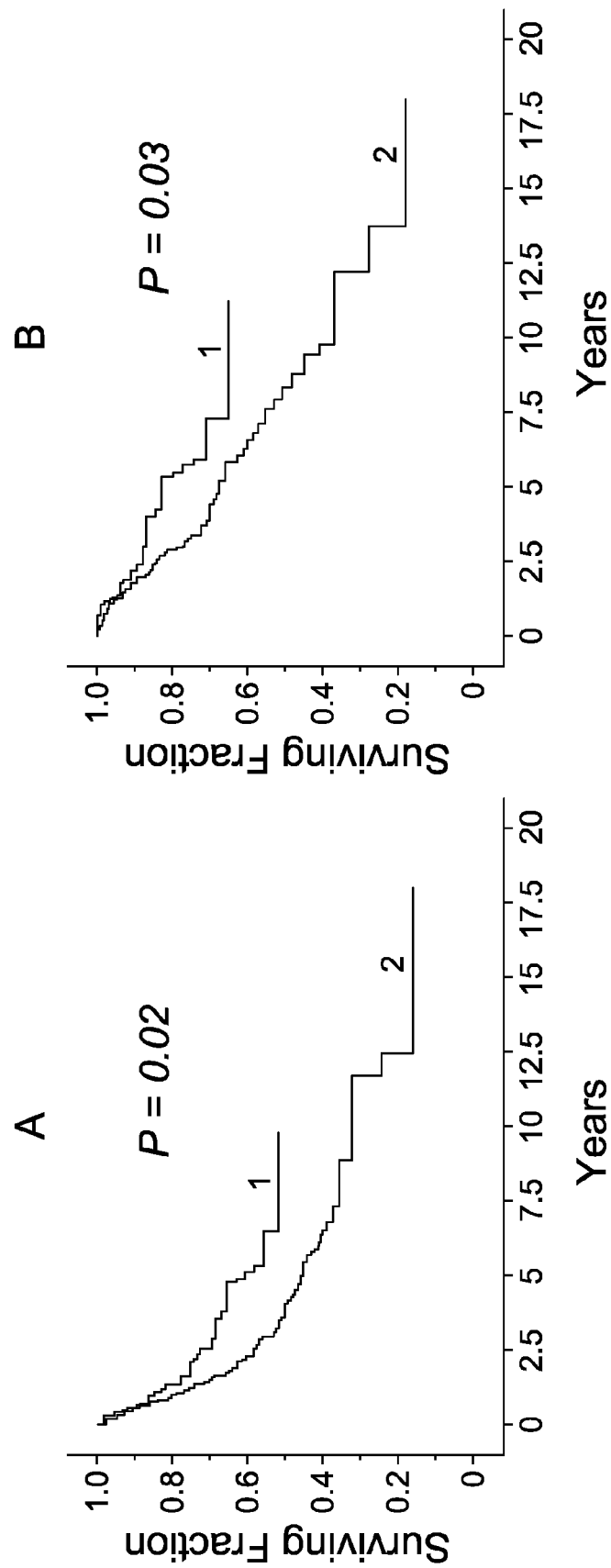
FIG. 2: Kaplan-Meier analysis of relapse free survival (RFS) (panel A) and disease specific survival (DSS) (panel B) according to NCOA3 expression level.

First, we analyzed the association between NCOA3 expression and melanoma outcome by univariate analysis. High NCOA3 expression (defined as a score of 2 or 3) significantly increased the risk of melanoma relapse (52.2% vs. 35.9%, P=0.010, Fisher exact test) and reduced the RFS of melanoma patients in this cohort when analyzed by Kaplan-Meier analysis (P=0.021, Log-Rank test, FIG. 2A). High NCOA3 expression was associated with increased risk of death due to melanoma (31.9% vs. 18.5%, P=0.021, Fisher exact test) and reduced DSS by Kaplan-Meier analysis (P=0.030, Log-rank test, FIG. 2B).

In addition to risk of relapse and death, increasing NCOA3 expression correlated significantly with positive SLN status, a measure of micrometastasis to the regional nodal basin, by logistic regression analysis (P=0.013). Patients with an NCOA3 staining score of 0 had a 7.1% prevalence of SLN positivity, which increased to 27.4% in patients with a score of 1 or 2, and 38.3% in patients with a score of 3 (P=0.036, Chi-square test). Intriguingly, level of NCOA3 expression also correlated with SLN tumor burden as measured by mean number of SLNs involved. Thus, in patients with an NCOA3 staining score of 0, the mean number of nodes involved was 0.07. This increased to 0.47 nodes in patients with a score of 1 or 2, and 0.57 nodes in patients with a score of 3 (P=0.0004 ANOVA, P=0.030 Le directional test).

Next, we examined the impact of NCOA3 expression on melanoma outcome by multivariate analysis. Multivariate Cox regression analysis was performed, including NCOA3 status and six clinical and histological prognostic factors evaluated by the AJCC staging committee for melanoma, including tumor thickness and ulceration, the factors currently used in the AJCC staging classification for cutaneous melanoma (see Balch C. M et al., *J Clin Oncol*, 19:3622-3634, 2001; Balch C. M et al., *J Clin Oncol*, 19:3635-3648, 2001). This analysis revealed NCOA3 status to be an independent predictor of both RFS (Table 2) and DSS (Table 3). In the Cox regression analysis of DSS, NCOA3 emerged as the most powerful factor determining survival, surpassing both tumor thickness and ulceration. Subsequently, multivariate logistic regression analysis demonstrated NCOA3 expression to be an independent predictor of SLN status when the six other prognostic factors were included in the model (Table 4).

Finally, we aimed to assess the predictive value of various prognostic factors when all 12 factors included in the dataset (and available for analysis) were entered in the multivariate models. In addition to the seven factors mentioned previously, this analysis included mitotic rate, degree of tumor vascularity, as well as presence or absence of vascular involvement, microsatellites, and regression. NCOA3 overexpression remained significantly predictive of DSS and SLN status (data not shown), when all 12 factors were included in the multivariate models.

TABLE 2

Cox regression analysis of impact of clinical, histological, and molecular factors on RFS of melanoma cohort

| Prognostic factor | Risk Ratio | Chi-square | P value (two-tailed) |
| --- | --- | --- | --- |
| Clark level | 2.22 | 16.77 | <.00005 |
| Ulceration | 1.94 | 13.86 | .0002 |
| NCOA3 level (2,3 vs. 0,1) | 1.69 | 6.72 | .0095 |
| Tumor thickness | 1.27 | 5.28 | .022 |
| Site | 1.39 | 3.61 | .057 |
| Age | 1.03 | .22 | .64 |
| Sex | 1.04 | .04 | .85 |

TABLE 3

Cox regression analysis of impact of clinical, histological, and molecular factors on DSS of melanoma cohort

| Prognostic factor | Risk Ratio | Chi-square | P value (two-tailed) |
|---|---|---|---|
| NCOA3 level (2,3 vs. 0,1) | 1.91 | 5.29 | .021 |
| Tumor thickness | 1.34 | 4.69 | .030 |
| Ulceration | 1.65 | 4.89 | .027 |
| Clark level | 1.75 | 5.00 | .025 |
| Age | 1.09 | 1.65 | .20 |
| Site | 1.41 | 2.27 | .13 |
| Sex | 1.00 | .0002 | .99 |

TABLE 4

Logistic regression analysis of impact of clinical, histological, and molecular factors on SLN metastasis

| Prognostic factor | Chi-square | P value (two-tailed) |
|---|---|---|
| Decreasing age | 12.92 | .0003 |
| Tumor thickness | 8.10 | .0044 |
| Clark level | 5.14 | .023 |
| NCOA3 expression (3 vs. 1, 2 vs. 0) | 5.70 | .017 |
| Sex | 1.43 | .23 |
| Ulceration | 0.79 | .37 |
| Site | 0.09 | .76 |

Discussion

These results show that NCOA3 overexpression in primary cutaneous melanoma correlates significantly with melanoma relapse and disease-specific-death. NCOA3 expression was significantly predictive of RFS and DSS of this cohort when the six prognostic factors analyzed by the AJCC staging committee were included in the multivariate models. Importantly, NCOA3 expression outperformed tumor thickness in each of these analyses, and emerged as the most powerful factor predicting DSS. Since the publication of the revised AJCC staging classification for melanoma (see Balch C. M et al., *J Clin Oncol*, 19:3635-3648, 2001), few molecular prognostic factors have been shown to be of independent prognostic significance when the six factors analyzed by the AJCC staging committee have been included in multivariate models, highlighting the potential significance of the findings correlating NCOA3 expression and outcome associated with melanoma.

In addition, NCOA3 status continued to provide independent prognostic information regarding DSS and SLN status when all 12 available prognostic factors were included in the model. This analysis included factors such as mitotic rate and vascular involvement, which have been shown in various analyses to be more powerful than ulceration (see Kashani-Sabet M. et al., *J Clin Oncol*, 20:1826-1831, 2002; Azzola M. F. et al., *Cancer*, 97:1488-1498, 2003. Taken together, these results demonstrate the utility of NCOA3 as a novel, independent molecular marker of melanoma outcome, with a significant impact on important outcome measures for melanoma.

Interestingly, the metastases examined in the gene expression profiling study that overexpressed NCOA3 were primarily lymph node metastases, indicating the potential importance of NCOA3 expression to melanoma lymph node metastasis. Not only did high NCOA3 expression correlate with a significantly increased risk of SLN metastasis.

Figure 3:
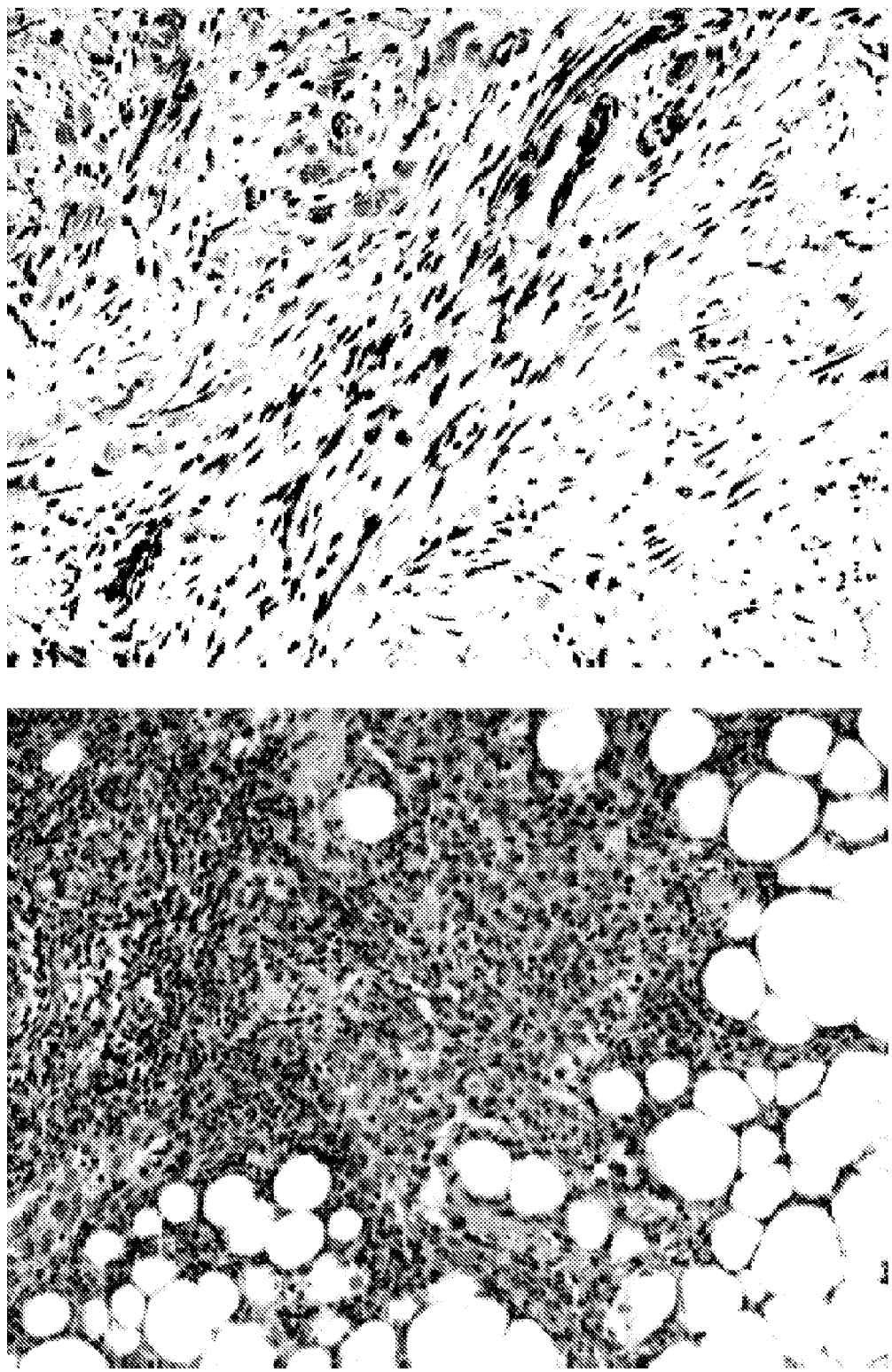
FIG. 3: Upper Panel. NCOA3 immunostaining in a desmoplastic melanoma. Note brown staining of spindled cells. Lower panel. NCOA3 immunostaining in the lymph node metastasis from the same patient. Note diffuse staining of tumor cells in the center.

Consistent with the strong correlation between NCOA3 expression and SLN status was the observation that high NCOA3 expression was rarely seen in the small subset of desmoplastic melanomas included in this analysis. We have also performed immunohistochemistry on a patient with desmoplastic melanoma with positive sentinel lymph node biopsy. The analysis demonstrates positivity in both the primary tumor as well as the lymph node metastasis (FIG. 3). This suggests the utility of NCOA3 immunostaining in identifying cases of desmoplastic melanoma that undergo sentinel lymph node metastasis.

Given the predominance of patients undergoing SLN biopsy in this data set, it is possible that some of the results reported herein may have been skewed by selection bias. Controversy still exists as to the selection of patients undergoing SLN biopsy in the setting of thin (<1.0 mm) and thick (>4.0 mm) tumors, and particular histological subtypes, such as desmoplastic melanoma. Thus, the selection criteria used to recommend SLN biopsy may have influenced the reported outcome data. As a result, the significance of NCOA3 overexpression may be most relevant to patients undergoing SLN biopsy.

Finally, these results reveal the broad-based significance of NCOA3 as a prognostic marker in cancer given its importance in hormone-sensitive and hormone-independent malignancies.

In conclusion, our results show a significant correlation between NCOA3 overexpression and increased risk of relapse and reduced survival associated with melanoma. In addition, they reveal NCOA3 expression to be independently predictive of several measures of melanoma outcome, including DSS, RFS, and SLN status, revealing that NCOA3 is a novel prognostic marker for primary cutaneous melanoma.

Example 2

Figure 4:
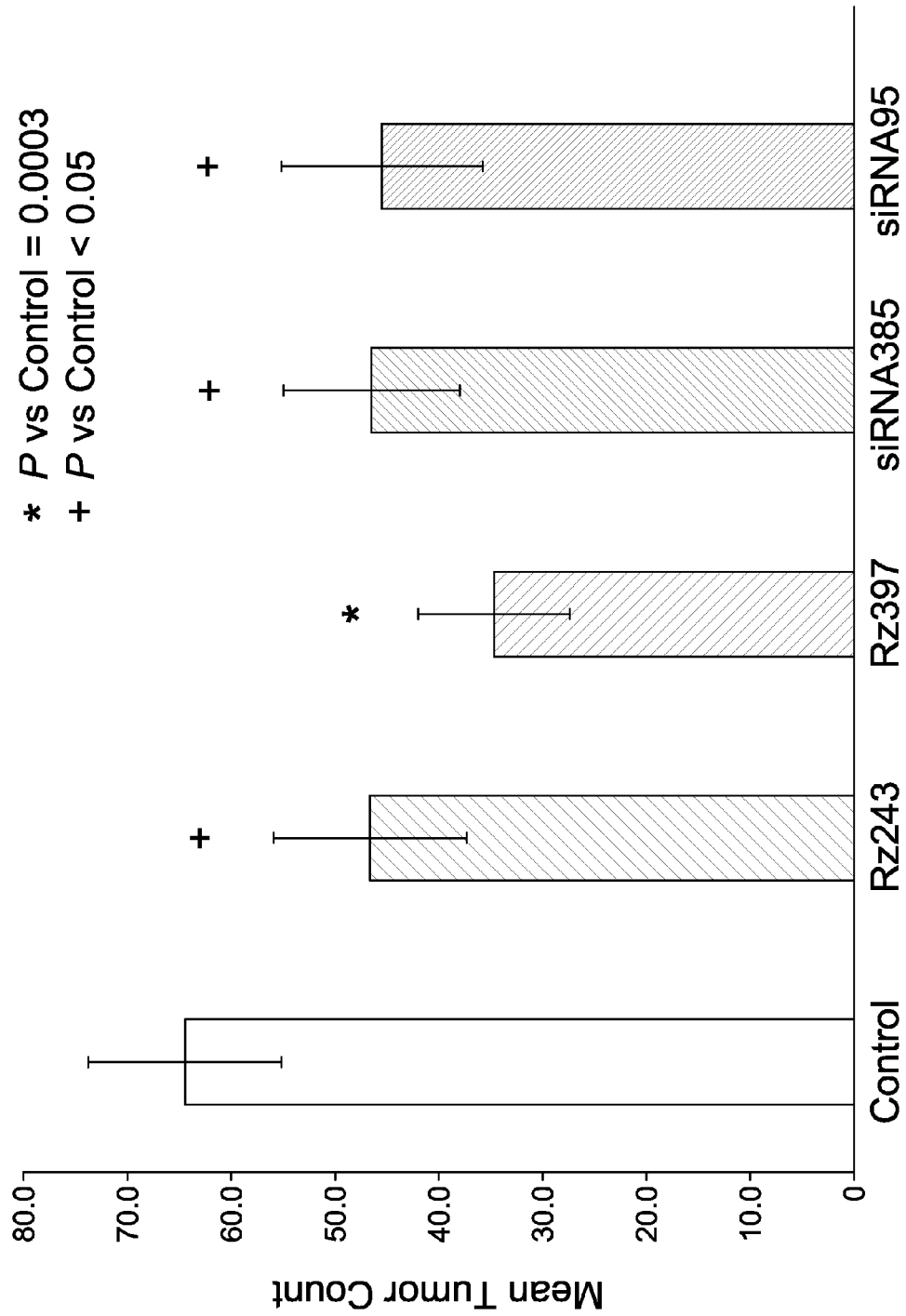
FIG. 4: Anti-metastatic activity of ribozymes (Rz) and siRNAs targeting murine NCOA3. B16-F10 melanoma cells were injected intravenously into groups of 10 C57B1/6 mice. On days 3 and 10 following injection, cationic lipid:DNA complexes encoding control vector sequences or two ribozymes and siRNAs targeting different sites of murine NCOA3 RNA were injected intravenously. Mice were sacrificed on day 25 and analyzed for number of metastatic lung tumors. All four constructs demonstrated significant reductions in metastatic tumor burden compared with the control (4613) vector alone (P<0.05).
Figure 5:
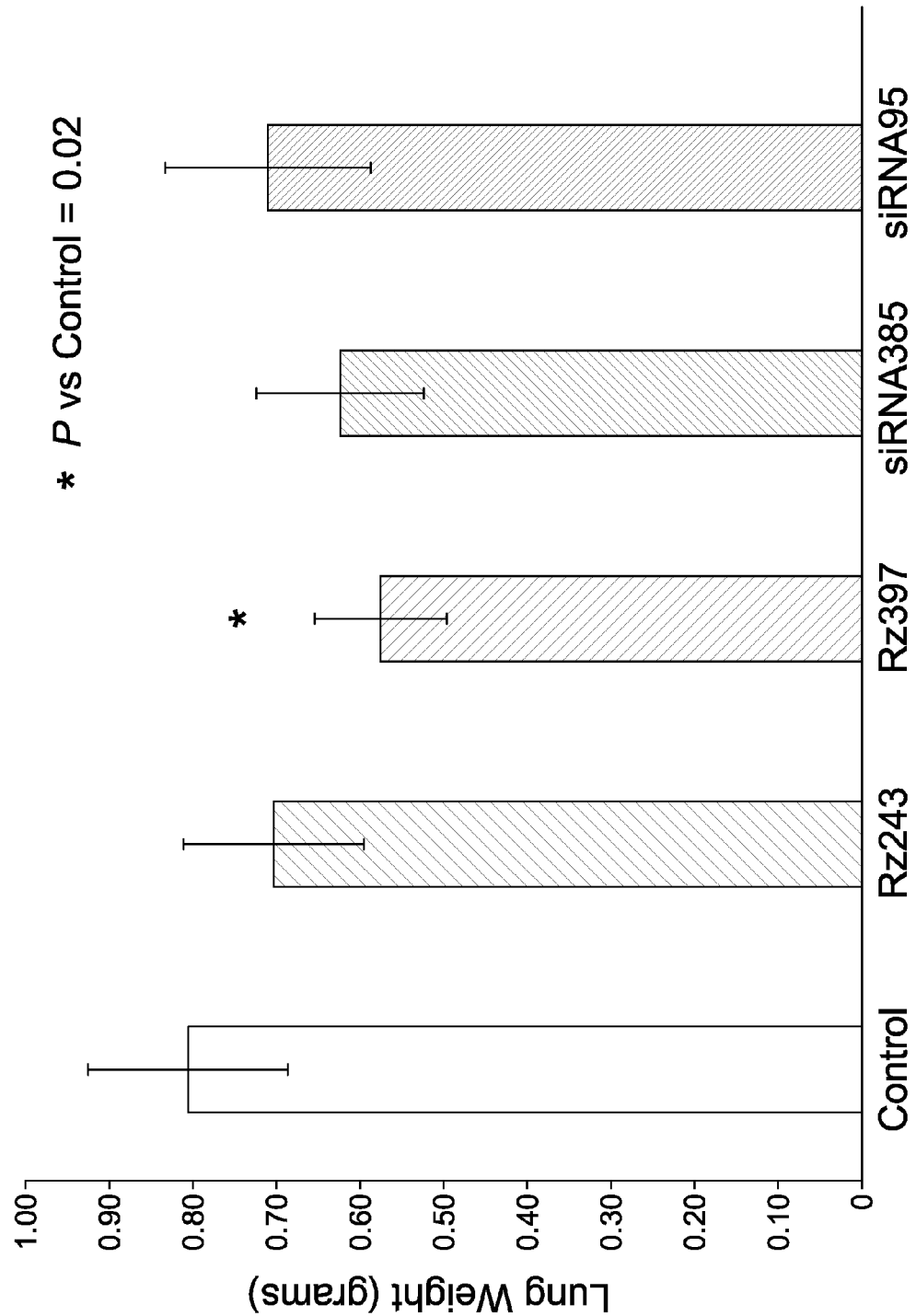
FIG. 5: Lung weights of tumor-bearing mice treated with various anti-NCOA3 or control constructs. Experimental details are identical to those described in FIG. 4.

Inhibition of NCOA3 Suppresses Metastatic Progression of Melanoma in Murine Models This example shows that expression of the NCOA3 gene is important for maintenance of the metastatic phenotype in melanoma. We used systemic non-viral ribozyme (Kashani-Sabet, 2002) and siRNA-based gene delivery in order to target the NCOA3 gene. Hammerhead ribozymes and siRNAs targeting murine NCOA3 were cloned into our expression plasmid, and tumor-bearing mice were treated with control or NCOA3-suppressing vectors on day 3 and 10 following tumor cell inoculation. Analysis of the metastatic tumor burden in the lung (as evidenced by number of lung tumors) showed a significant decrease in animals treated with either the anti-NCOA3 ribozyme or siRNA versus vector control (FIG. 4). Analysis of lung weights, another measure of metastatic tumor burden, revealed Rz397 as the only construct to significantly suppress the lung weights of C57B1/6 mice (FIG. 5). These studies clearly demonstrate the utility of gene expression profiling in the identification of functional, as well as molecular markers of melanoma progression. Furthermore, they indicate that markers identified by cDNA microarray analyses can represent targets for therapy of metastatic melanoma.

Figure 6:
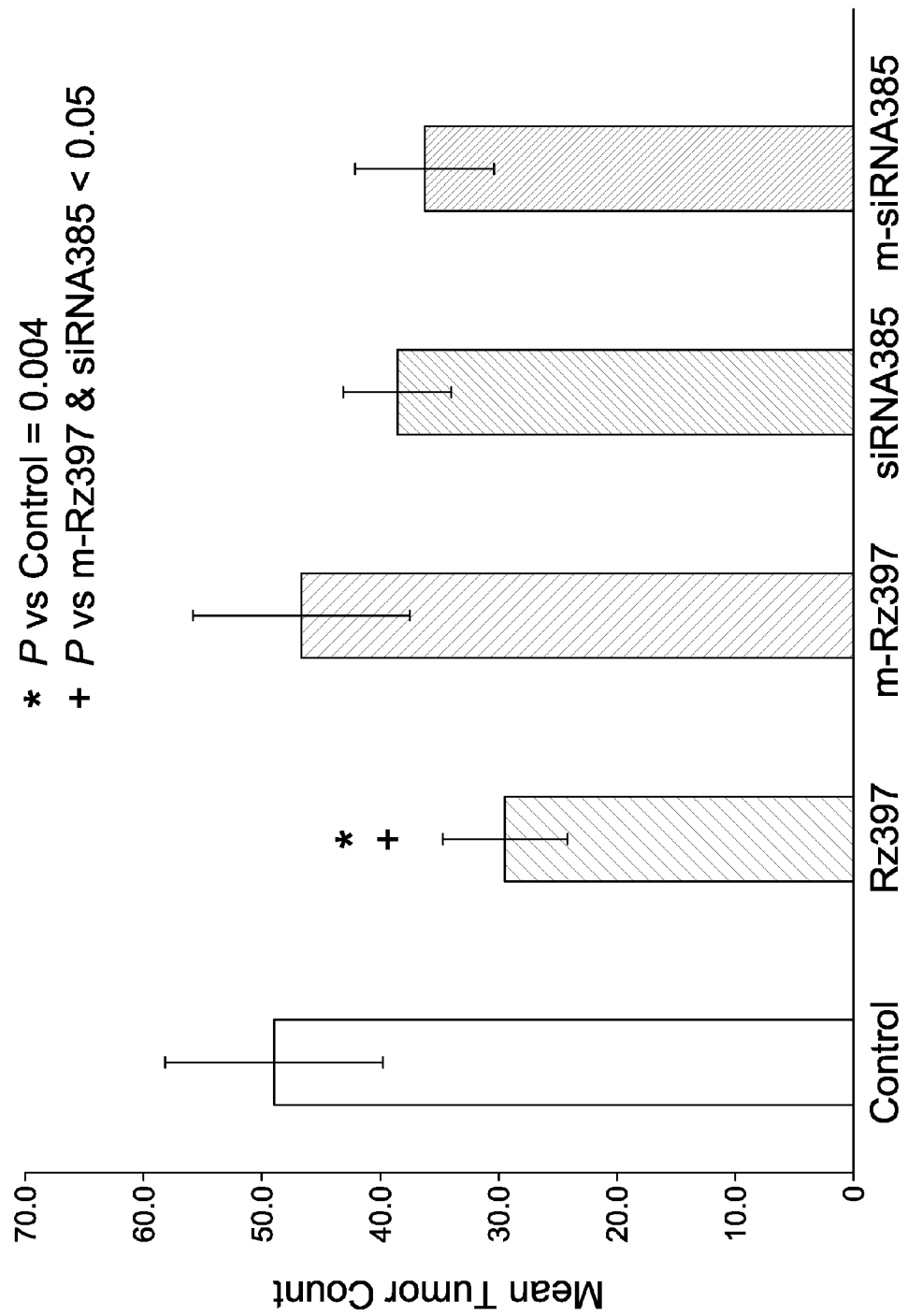
FIG. 6: Anti-metastatic activity of ribozyme 397 (Rz) targeting NCOA3 against murine breast cancer. 4T1 breast carcinoma cells were injected intravenously into groups of 10 BALB/c mice. On days 3 and 10 following injection, cationic lipid:DNA complexes encoding control vector sequences, Rz397, siRNA385, and mutant controls containing a single base mutation in the ribozyme (m-Rz397) or siRNA (m-siRNA385) were injected intravenously. Mice were sacrificed on day 25 and analyzed for number of metastatic lung tumors. The Rz397-treated mice had significantly fewer lung tumors than mice treated with siRNA385, m-Rz397, or with the control vector alone.

Interestingly, systemic administration of the anti-NCOA3 ribozyme targeting nucleotide 397 also suppressed the metastatic progression of 4T1 murine breast carcinoma cells in BALB/c mice (FIG. 6). In the 4T1 model, the ribozyme was superior in its anti-tumor effects compared with the siRNA targeting the same region of NCOA3, as well as the vector control and mutant, disabled ribozyme and siRNA controls.

These results suggest the potential therapeutic utility of targeting NCOA3 in the therapy of metastatic breast cancer as well as melanoma.

Figure 7:
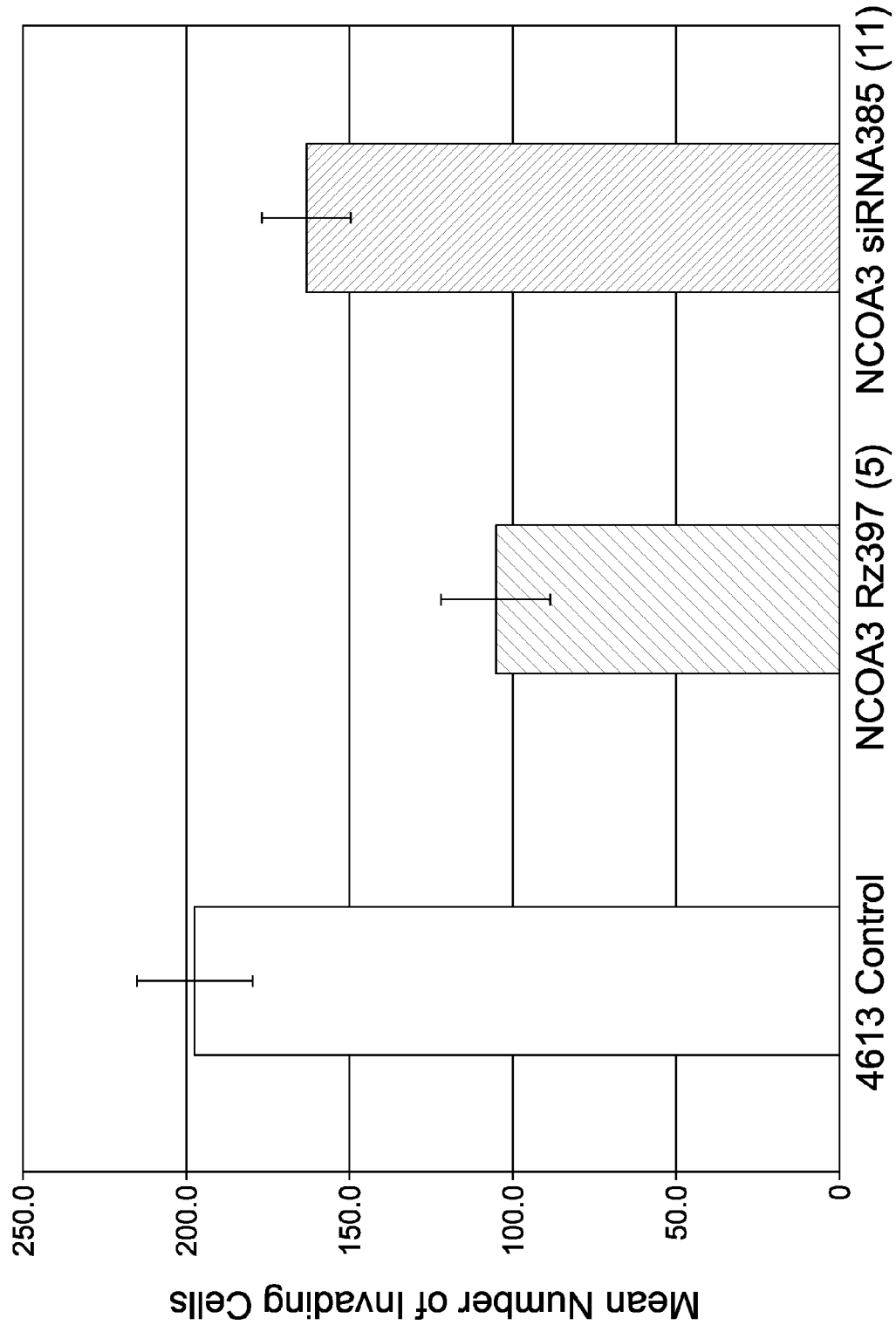
FIG. 7: Targeting NCOA3 suppresses tumor cell invasion in vitro. B16 cells were transfected with vector only, or vector expressing Rzs397 or siRNA385 targeting murine NCOA3, and invasion was determined using a Boyden chamber assay 24 hrs following transfection.

Finally, transient transfection of Rz397 or siRNA385 into B16 melanoma cells in vitro reduced tumor cell invasion into matrigel, suggesting a potential mechanism whereby targeting NCOA3 suppresses tumor metastasis (FIG. 7).

Example 3

Differential Expression of Wnt-2 in the Progression of Melanoma

We performed immunohistochemical analysis of WNT-2 expression in a test set tissue microarray of 40 benign nevi and 376 primary melanomas, and a validation set of 34 tissue sections of primary melanoma arising in association with a nevus. Benign nevi showed strong staining for Wnt-2 in the junctional zone of the nevus, with almost universal loss of expression at the nevus base. In contrast, primary melanomas showed a more uniform staining pattern, without apparent variation in staining throughout the vertical growth phase. Wnt-2 immunostaining at the base of primary melanomas was significantly higher than at the base of nevi. Matched-pair analysis of Wnt-2 expression of melanoma arising in association with a nevus showed that the Wnt-2 staining in the nevus junctional zone was significantly higher in all cases compared with the base of the same nevus. In addition, Wnt-2 scores for the primary melanomas were significantly higher in all cases when compared with their matched controls at the nevus base. These results presented below validate the importance of WNT pathway activation in melanoma progression, and reveal that Wnt-2 as a novel biomarker for melanoma.

Selection of Nevi and Melanomas for Incorporation into Data Set

Two data sets were constructed for the analysis performed in this study: (i) a test set consisting of a tissue microarray of 138 benign nevi and 376 primary melanomas, and (ii) a validation set of 34 tissue sections of primary melanoma arising in a nevus. Of the 138 nevi included in the nevus arrays, 40 had a portion of the epidermis included in the core to allow for accurate analysis of Wnt-2 staining at the junctional zone of the nevus versus the nevus base. The composition of the 40 nevi in the microarrays studied is as follows: 5 acquired compound nevi, 9 congenital compound nevi, 7 acquired intradermal nevi, 17 congenital intradermal nevi, 1 acquired dysplastic nevus, and 1 junctional nevus. The histologic subtypes of primary melanoma included in the melanoma microarrays is as follows: 176 superficial spreading melanoma, 132 nodular melanoma, 14 lentigo maligna melanoma, 22 acral melanoma, 10 desmoplastic melanoma, and 22 melanoma not otherwise classified. In the validation set, we created tissue sections from 34 cases of primary melanoma arising in a nevus. Of the 34 cases, 28 had nevus with both junctional and dermal components, whereas 31 had both dermal nevus and invasive melanoma. The following is the breakdown of histologic subtype for nevus and melanoma: 22 congenital nevi, 8 acquired nevi, 1 dysplastic nevus, 19 superficial spreading melanoma, 7 nodular melanoma, and 5 melanoma not otherwise classified.

Tissue Arrays

Tissue microarrays were created as previously described by taking 1.0 mm in diameter tissue cores using a Beecher arraying instrument (see Kononen, J. et al., *Nat Med*, 1998, 4: 844-847; Kashani-Sabet M. et al., *J Clin Oncol*, 2004, 22: 617-623). Following construction of the block, 5 µm sections were cut using a tissue microtome and placed on charged slides. A total of 16 melanoma arrays and a total of 4 nevus arrays were made with an average of approximately 40 tissues per array. Melanoma arrays included a total of 673 tissue cores (457 primary melanomas with duplicate cores for 150 patients). Nevus arrays included a total of 138 tissue cores. Of the 457 primary melanomas on the tissue microarray, 376 were interpretable for Wnt-2 staining.

Immunohistochemistry

Slides were baked at 60° C. for 30 min prior to staining, and deparaffinized and rehydrated by rinsing in xylene. The slides were then microwaved in 10 mM citrate buffer. Endogenous peroxidase activity was blocked with 3% hydrogen peroxide. After washing with PBS, the slides were incubated at room temperature for 30 min with normal rabbit serum to reduce nonspecific background staining, and then washed with PBS. The primary antibody, goat polyclonal anti-Wnt-2 IgG (Biovision) was then added at a 1:5 dilution and incubated overnight at 4° C. Biotinylated goat anti-rabbit IgG antibody (Vector Laboratories, Burlingame, Calif.) was used as a secondary antibody for amplification, followed by incubation with ABC-HRP (Vector Laboratories) for 30 min, and DAB/Hydrogen peroxide solution (Sigma). Slides were counterstained with hematoxylin and mounted with permount. The same Wnt-2 immunohistochemical staining protocol was utilized for tissue array slides and routine sections.

Evaluation of Immunohistochemical Staining

The regions of most intense staining were scored for each tissue array core and tissue section. Expression of Wnt-2 protein was graded using the following scale: no staining (0), weak staining (1+), moderate staining (2+), and intense staining (3+). Specimens with no invasive melanoma or nevus or specimens that were not interpretable were excluded from the analysis. The arrays and sections were scored by a pathologist blinded to the identity of the cases with two separate scorings and a consensus score determined for discrepant scoring. Specificity controls for Wnt-2 staining included breast tumor, melanoma cell lines (LOX and FEM) and melanoma tissue sections.

Statistical Analysis

Statistical methods used to assess the significance of various prognostic factors on the outcome associated with melanoma are as follows: in the tissue microarrays, the potential difference between Wnt-2 immunostaining in the nevus junctional zone and the nevus base was tested using the binomial sign test and the Wilcoxon matched-pairs signed-ranks test. The potential difference between Wnt-2 immunostaining in the nevus base and in the melanoma base was tested using the Mann-Whitney test. In the tissue sections of primary melanoma arising in a nevus, the potential difference between Wnt-2 immunostaining in the nevus junctional zone and the nevus base was tested using the binomial sign test and the Wilcoxon matched-pairs, signed-ranks test. The potential difference between Wnt-2 immunostaining in the nevus base and in the melanoma base was tested using the binomial sign test and the Wilcoxon matched-pairs, signed-ranks test. All P values reported are two sided.

Results

Given our cDNA microarray results showing differential expression of the Wnt pathway in melanomas when compared with nevi, we aimed to probe the differential expression of Wnt-2 in a larger, independent cohort of melanocytic neoplasms. To this end, we constructed a test set containing tissue microarrays with 138 melanocytic nevi and 376 primary melanomas, and a validation set of 34 tissue sections containing primary melanomas with a pre-existing nevus. Wnt-2 expression was analyzed using a commercially available monoclonal antibody targeting human Wnt-2. In the process of optimizing the immunohistochemical staining for Wnt-2, we found an intriguing staining pattern for Wnt-2 in benign nevi. Benign nevi showed a strong staining for Wnt-2 in the junctional zone of the nevus, with almost universal loss of expression at the nevus base (FIG. 8).

As a result of this finding, we restricted our analysis of Wnt-2 expression in the nevus tissue microarrays to those nevus cores containing a piece of the epidermis, such that comparison of the immunostaining between the nevus junctional zone and nevus base would be possible. This reduced the effective nevus array set to 40 cases. In each of the 40 cases examined, Wnt-2 immunostaining was higher in the junctional zone of the nevus, when compared with its matched base, a finding that was highly significant (P<0.00005, binomial sign test). The loss of Wnt-2 immunostaining at the nevus base was still significant when broken down into nevus subtypes for the two most common histologic subtypes of nevus present in the arrays, namely intradermal and compound melanocytic nevi (P<0.001, binomial sign test).

Figure 9:
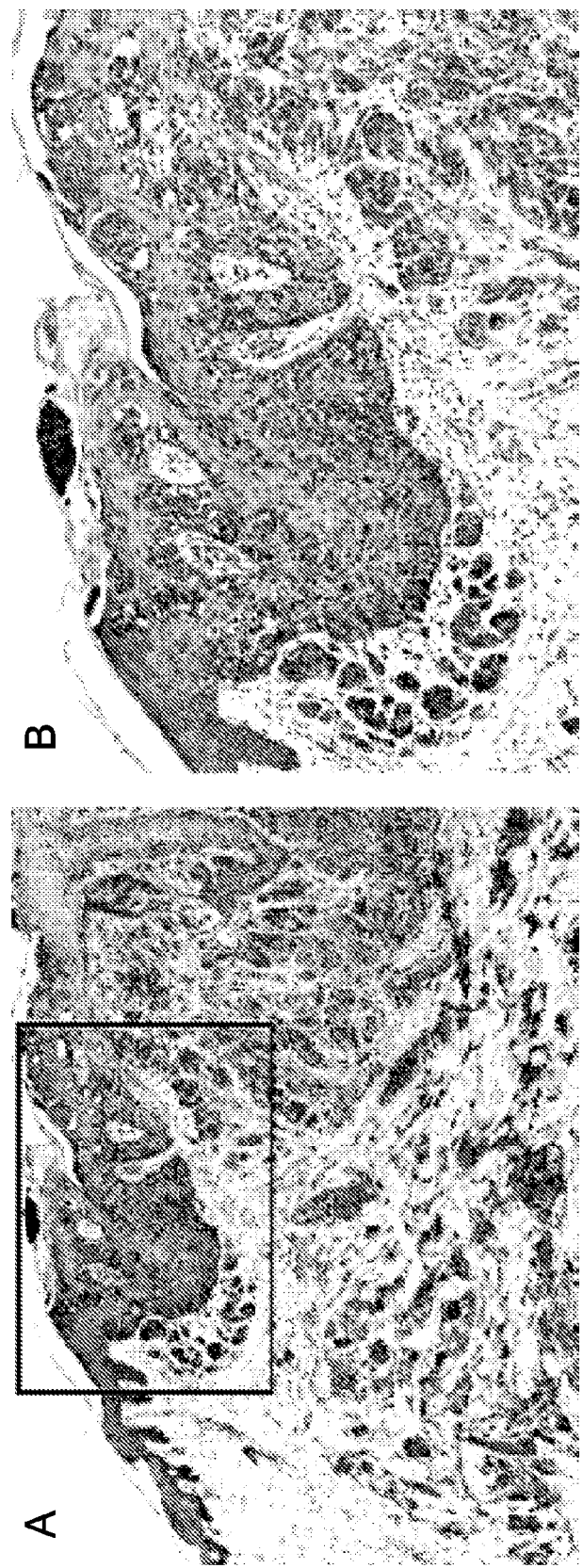
FIG. 9: Low-power (40×, panel A) and high-power (100×, panel B) photomicrographs of Wnt-2 immunostaining in a primary melanoma (4.1 mm thick, Clark level IV) demonstrating intensely staining intraepidermal melanoma clusters invading into the dermis.

Next, we examined Wnt-2 immunostaining in a tissue array containing 376 primary melanoma cores. In contrast to nevi, primary melanomas demonstrated a more uniform pattern of staining, with no decrease in staining throughout the vertical growth phase (FIG. 9). The great majority of primary melanomas analyzed demonstrated some Wnt-2 expression, as staining was absent in only 8 cases (3.8%). Moreover, strength of Wnt-2 expression was uniformly present across the different histologic subtypes of melanoma (Table 5). There was no significant correlation between Wnt-2 expression and several well-known prognostic markers for melanoma, including tumor thickness, Clark level, ulceration, mitotic rate, microsatellites, and vascular involvement (data not shown).

TABLE 5

Degree of Wnt-2 Expression Across Different Histologic Subtypes of Primary Melanoma

| Histologic Subtype Number of Cases (%) | Wnt-2 Score | | | |
|---|---|---|---|---|
| | 0 | 1 | 2 | 3 |
| SSM | 7/176 (4.0) | 45/176 (25.6) | 92/176 (52.3) | 32/176 (18.2) |
| NM | 5/132 (3.8) | 28/132 (21.2) | 60/132 (45.5) | 39/132 (29.5) |
| LMM | 0/14 | 5/14 (35.7) | 7/14 (50) | 2/14 (14.3) |
| AM | 1/22 (4.5) | 7/22 (31.8) | 11/22 (50) | 3/22 (13.6) |
| DM | 0/10 | 5/10 (50) | 3/10 (30) | 2/10 (20) |
| NOC | 1/22 (4.5) | 10/22 (45.5) | 8/22 (36.4) | 3/22 (13.6) |

Abbreviations: SSM, superficial spreading melanoma; NM, nodular melanoma; LMM, lentigo maligna melanoma; AM, acral melanoma; DM, desmoplastic melanoma; NOC, melanoma not otherwise classified.

We then compared the Wnt-2 immunostaining in the primary melanomas with that observed in the nevi. Given the pattern of Wnt-2 expression in the nevi, we compared the Wnt-2 score at the base of the nevus with that observed at the base of the melanoma. The mean score at the base of the melanomas (1.88) was significantly greater than the mean score at the base of the nevi (0.57, P<0.00005, unpaired T test).

In order to further examine the differential Wnt-2 expression between nevi and primary melanomas observed in the tissue microarrays, we reasoned that an optimal setting in which to evaluate potential differences were in cases of melanoma with pre-existing nevi, for which many potential confounding factors (age, gender, anatomical location, and potentially irrelevant histologic subtypes of nevus and melanoma, among others) are automatically controlled, thereby creating a de-facto matched-pairs analysis. Thus, we amassed a validation set of 34 cases of primary melanoma in association with a nevus, and performed immunohistochemical staining of Wnt-2 on 5 μM tissue sections.

Initially, we analyzed Wnt-2 expression in the nevus junctional zone versus the nevus base. Of the 34 cases, 28 had both junctional zone and nevus base present within the section. In each of the 28 cases, the Wnt-2 immunostaining at the junctional zone of the nevus was higher than its matched base, a finding that was highly significant (P<0.00005, binomial sign test and Wilcoxon matched-pairs, signed-ranks test). The dramatic decrease in the expression of Wnt-2 at the nevus base was corroborated by analyzing the percentage of cases with high versus low Wnt-2 scores. Thus, 90.6% of the junctional zones scored a 2 or 3, whereas, 94.1% of the nevi base scored a 0 or 1 (Table 6). Interestingly, there was no absent staining (score of 0) in the junctional zone of any nevi, and no robust staining (score of 3) in the base of the nevi examined, further illustrating this dichotomy.

TABLE 6

Degree of Wnt-2 immunostaining in nevus junctional zone versus nevus base

| Wnt-2 score | Nevus junctional zone (% cases expressing score) | Nevus base |
|---|---|---|
| 0/1+ | 9.4% | 94.1% |
| 2/3+ | 90.6% | 5.9% |

Figure 11:
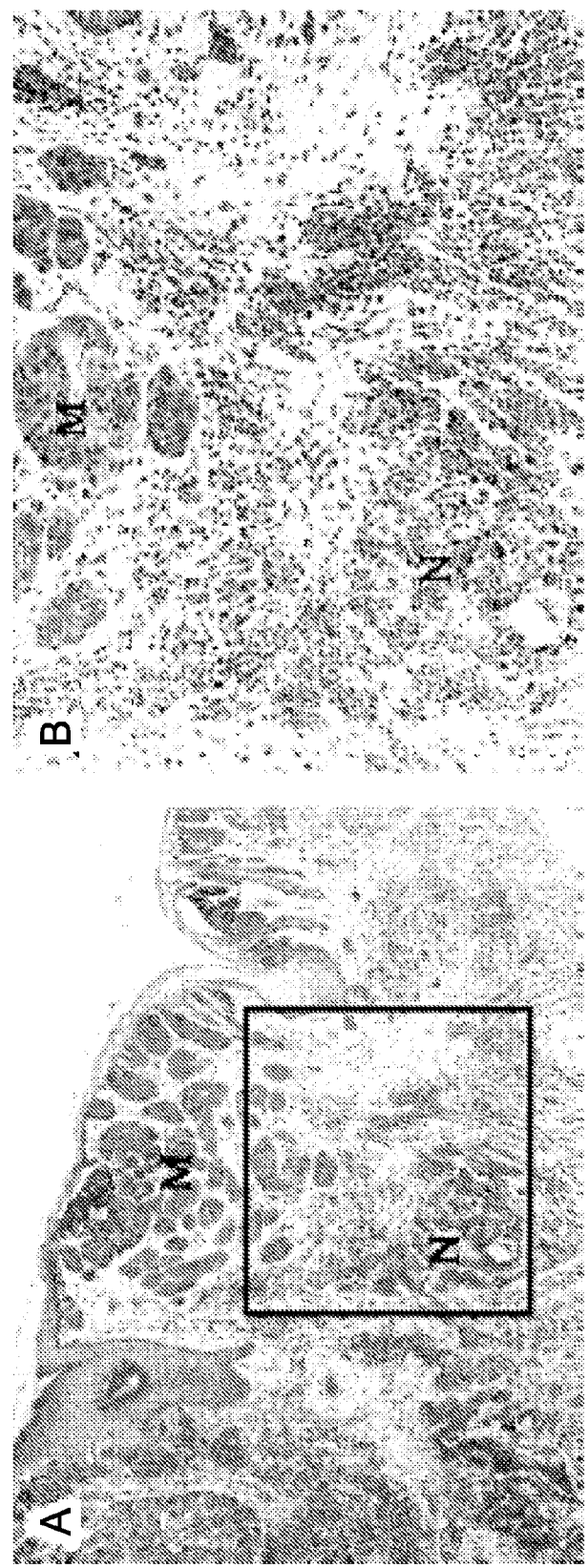
FIG. 11: Low-power (40×, panel A) and high-power (100×, panel B) photomicrographs of Wnt-2 immunostaining of a primary melanoma arising in a nevus, showing intensely staining melanoma (M) in both junctional and dermal components, with absent staining in an underlying dermal congenital nevus (N).

Finally, we compared the pattern of Wnt-2 expression at the base of the melanoma with that at the base of its associated nevus in the stained specimens. Of the 34 cases, 31 had both nevus base and melanoma base for comparison. In 29 cases, the Wnt-2 immunostaining was significantly higher at the base of the melanoma when compared with its matched nevus base (as shown in FIG. 11), with two cases showing identical Wnt-2 scores (P<0.00005, binomial sign test and Wilcoxon matched-pairs, signed-ranks test). In no case was Wnt-2 expression higher at the base of the nevus when compared with the melanoma. Once again, this phenomenon was reflected in the strength of Wnt-2 staining within the nevi and melanomas. Thus, 100% of melanomas had a Wnt-2 score of greater than 0, compared with 32.4% of the nevi (Table 7). None of the melanomas had absent Wnt-2 expression (score of 0), and none of the nevi showed strong staining (score of 3) at their base.

TABLE 7

Wnt-2 immunostaining in melanoma base versus nevus base

| Wnt-2 score | Melanoma base | Nevus base |
|---|---|---|
| 0 (% cases expressing score) | 0% | 67.6% |
| >0 (% cases expressing score) | 100% | 32.4% |

We have also performed Wnt-2 immunostaining on three additional cohorts, (i) dysplastic nevi, (ii) Spitz nevi, and (iii) misdiagnosed melanocytic neoplasms. Our analysis reveals that the differential Wnt-2 expression observed in the nevus cohorts can be extended specifically to dysplastic nevi (p<0.05) and Spitz nevi (p−0.004), nevus subtypes that are notable for the difficulty in distinguishing them from melanoma at the histopathologic level. In each of these cases, the Wnt-2 immunostaining was higher in the nevus junctional zone than in the nevus base, findings that were both statistically significant. Finally, we analyzed 7 cases in which an ambiguous melanocytic neoplasm was misdiagnosed based on subsequent disease recurrence (5 cases where a diagnosis of nevus proved incorrect) or expert pathology review (2 cases where a diagnosis of melanoma was overturned). In 6 of the 7 cases, the pattern of Wnt-2 immunostaining pointed to the eventual correct diagnosis, including all five of the cases initially misdiagnosed as nevus. These results show the ability of Wnt-2 immunostaining to assist in the diagnosis of ambiguous melanocytic neoplasms given its ability to correctly diagnose 85.7% of such cases.

Discussion

In this study, we provide convincing evidence of the differential expression of Wnt-2 at the protein level in the progression of melanoma. Our results clearly indicate that Wnt-2 is differentially expressed in melanomas when compared with melanocytic nevi, both in the tissue microarray analysis as well as in the matched-pair analysis, in which each melanoma was paired with its pre-existing nevus. In this latter analysis, only melanomas were found to express Wnt-2 highly at their base, and only nevi were shown to have absent Wnt-2 expression at their base.

In addition, an interesting pattern of Wnt-2 expression was observed in the melanocytic nevi. In every case examined, the expression of Wnt-2 was significantly lower in the nevus base than its junctional zone. Moreover, Wnt-2 immunostaining was absent at the base of a significant proportion (55%) of nevi examined across both the array studies and the analysis of melanoma arising in a nevus.

The significant differences in the pattern of Wnt-2 staining in nevi versus melanomas show the utility of Wnt-2 immunostaining in the molecular diagnosis of ambiguous melanocytic neoplasms. The results from the nevus and melanoma tissue arrays show a specificity of 98% for high Wnt-2 staining in the diagnosis of melanoma, with a specificity of 70%. Our data distinguishes between nevi and melanomas based on Wnt-2 expression level. Melanocytic lesions staining intensely (score of 2 or 3+) at their base were highly likely to be melanomas (99.6%). Lesions showing little staining at their base (score of 0 or 1) were melanomas 30% of the time, yielding the sensitivity observed. However, these lesions would then be analyzed in their junctional zone, with the nevi demonstrating decreased staining in the deeper portions in virtually every case, while melanomas demonstrated uniform staining between the junctional and deeper zones. To date, while markers of tumor cell proliferation (such as Ki-67; see Smolle, J. et al., *Am J Dermatopathol*, 1989, 11:301-307; Rieger, E. et al., *J Cutan Pathol*, 1993, 20:229-236; Kaleem, Z. et al., *Mod Pathol*, 2000, 13:217-222) have been analyzed for their role in this differential diagnostic dilemma, no markers have been shown to exhibit a strong difference in expression between nevus and melanoma to be clinically useful.

The decrease in immunostaining observed with Wnt-2 has been observed with a few other markers, including S100A6, Melan-A, and HMB-45 (see Fullen, D. R. et al., *J Cutan Pathol*, 2001, 28:393-399; Busam, K. J. et al., *Am J Surg Pathol*, 1998, 22:976-982; Kucher, C. et al., *Am J Dermatopathol*, 2004, 26:452-457). However, these markers are not routinely utilized to distinguish between nevi and primary melanomas. In addition, in some of these studies, intradermal nevi were the dominant nevus type examined. Intradermal nevi are known to undergo significant maturation at their base. In our study, when broken down by nevus subtype, there was significant downregulation of Wnt-2 immunostaining at the base of intradermal nevi, compound nevi (in general), as well as acquired compound nevi dysplastic and Spitz nevi, which may not have the same pattern of maturation. This demonstrates a more broad-based utility of Wnt-2 as a molecular diagnostic marker for melanoma.

The cDNA microarray results described in this invention also allow diagnostic versus prognostic markers to be distinguished in melanoma. Gene expression profiling revealed that distinct gene expression signatures characterized the transition from nevus to primary melanoma as that from primary to metastatic melanoma (see Haqq C. et al., *Proc Natl Acad Sci USA*, 2005, 102: 6092-6097). Accordingly, markers that were differentially expressed in the nevus to melanoma transition can be most useful as diagnostic markers, whereas markers identified in the primary to metastasis transition can be most useful as prognostic markers. This is supported by the Wnt-2 immunostaining results that suggest its greatest utility as a diagnostic rather than a prognostic marker. While there was a significant difference in Wnt-2 immunostaining between nevi and melanoma, there was no significant association between Wnt-2 expression and several known prognostic markers for melanoma.

Figure 10:
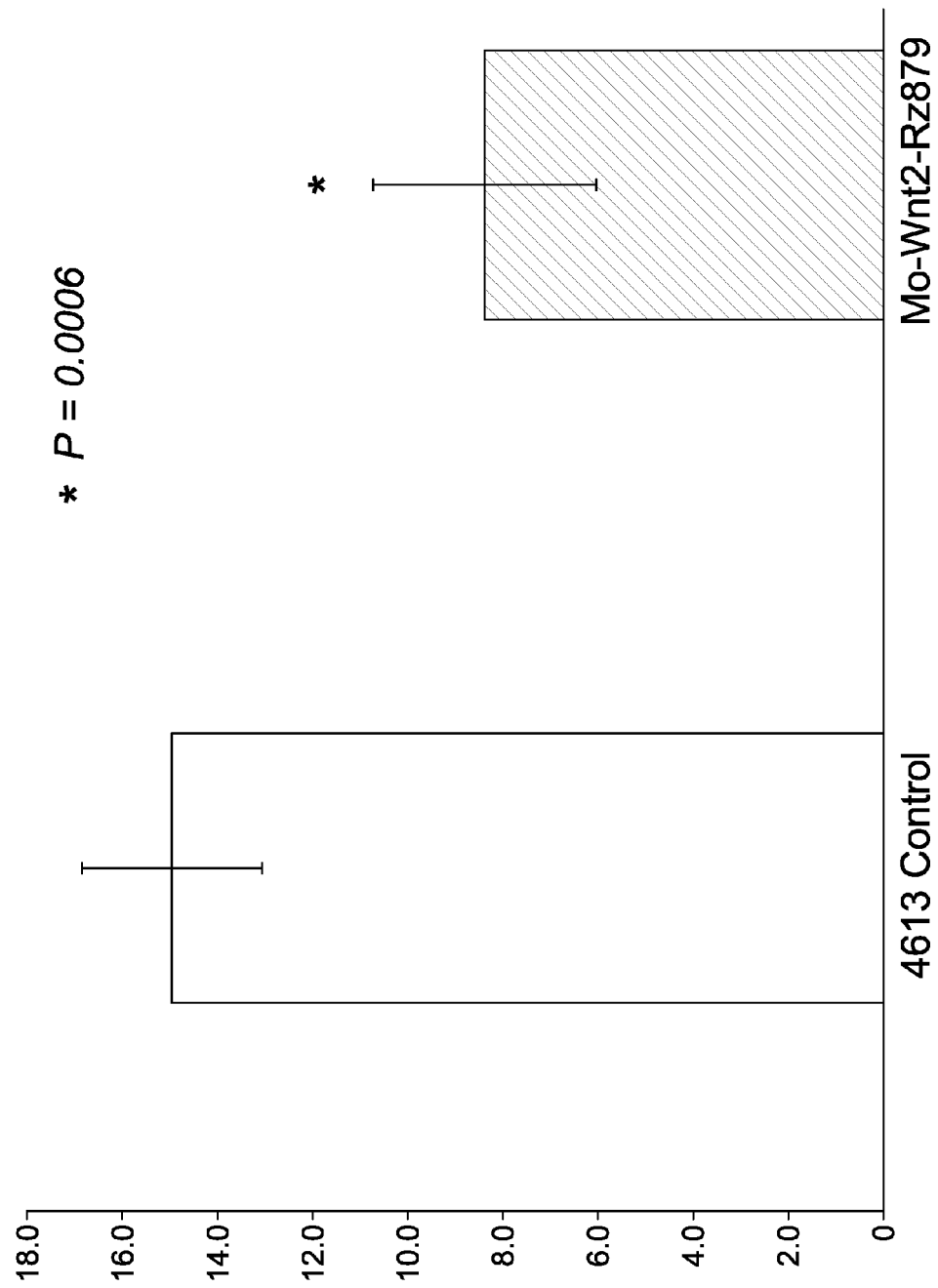
FIG. 10: Anti-metastatic activity of a ribozyme targeting murine Wnt-2 (Mo-Wnt2-Rz879). B16-F10 melanoma cells were injected intravenously into groups of 10 C57B1/6 mice. On day 7 following injection, cationic lipid:DNA complexes encoding control vector sequences or a ribozyme targeting different murine Wnt-2 RNA were injected intravenously. Mice were sacrificed on day 25 and analyzed for number of metastatic lung tumors. The anti-Wnt-2 ribozyme demonstrated significant reductions in metastatic tumor burden compared with the control (4613) vector alone (P=0.0006).

In order to analyze the potential therapeutic benefit of Wnt-2 targeting to metastatic progression, we analyzed the anti-tumor efficacy of systemic delivery of a hammerhead ribozyme targeting murine Wnt-2 against B16 melanoma. B16 cells were injected intravenously into C57B1/6 mice, and the mice treated either with a control empty vector or a plasmid vector expressing the anti-Wnt-2 ribozyme 7 days following tumor cell injection. Metastatic burden was assessed by the number of metastatic lung tumors upon sacrifice. As shown in FIG. 10, a single injection of the anti-Wnt-2 ribozyme expressing construct resulted in significant suppression of large (>2 mm), angiogenic-dependent lung tumors. These studies support the role of targeting Wnt-2 in the suppression of metastatic progression.

Taken together, these results show the importance of Wnt-2 to melanocyte transformation. While WNT pathway activation appears to occur early in the development of melanoma, data from both in vitro and in vivo studies suggest that Wnt-2 expression is required for ongoing survival and proliferation of melanoma cells. Both antibody- and siRNA-based targeting of Wnt-2 resulted in induction of apoptosis of several melanoma cell lines in vitro, and in significant suppression of growth of xenografts in vivo. Preliminary studies obtained in our laboratory also suggest a requirement for Wnt-2 expression in the metastatic progression of melanoma in murine models (see FIG. 10 above). Thus, these results suggest the potential therapeutic utility of Wnt-2 targeting as a rational therapeutic strategy for melanoma. And the immunostaining assay used here may aid in the identification of a patient cohort eligible for a targeted therapeutic approach with specific Wnt-2 inhibitors.

In conclusion, our studies demonstrate the differential expression of the WNT pathway in melanomas versus nevi, confirming results previously obtained from gene expression profiling of melanocytic neoplasms. In addition, they confirm the importance of WNT-2 activation in the progression of melanoma. Finally, they teach the utility of Wnt-2 as a novel biomarker for melanoma and as a potential target for therapy.

Example 4

Role of PHIP in Melanoma

Figure 12:
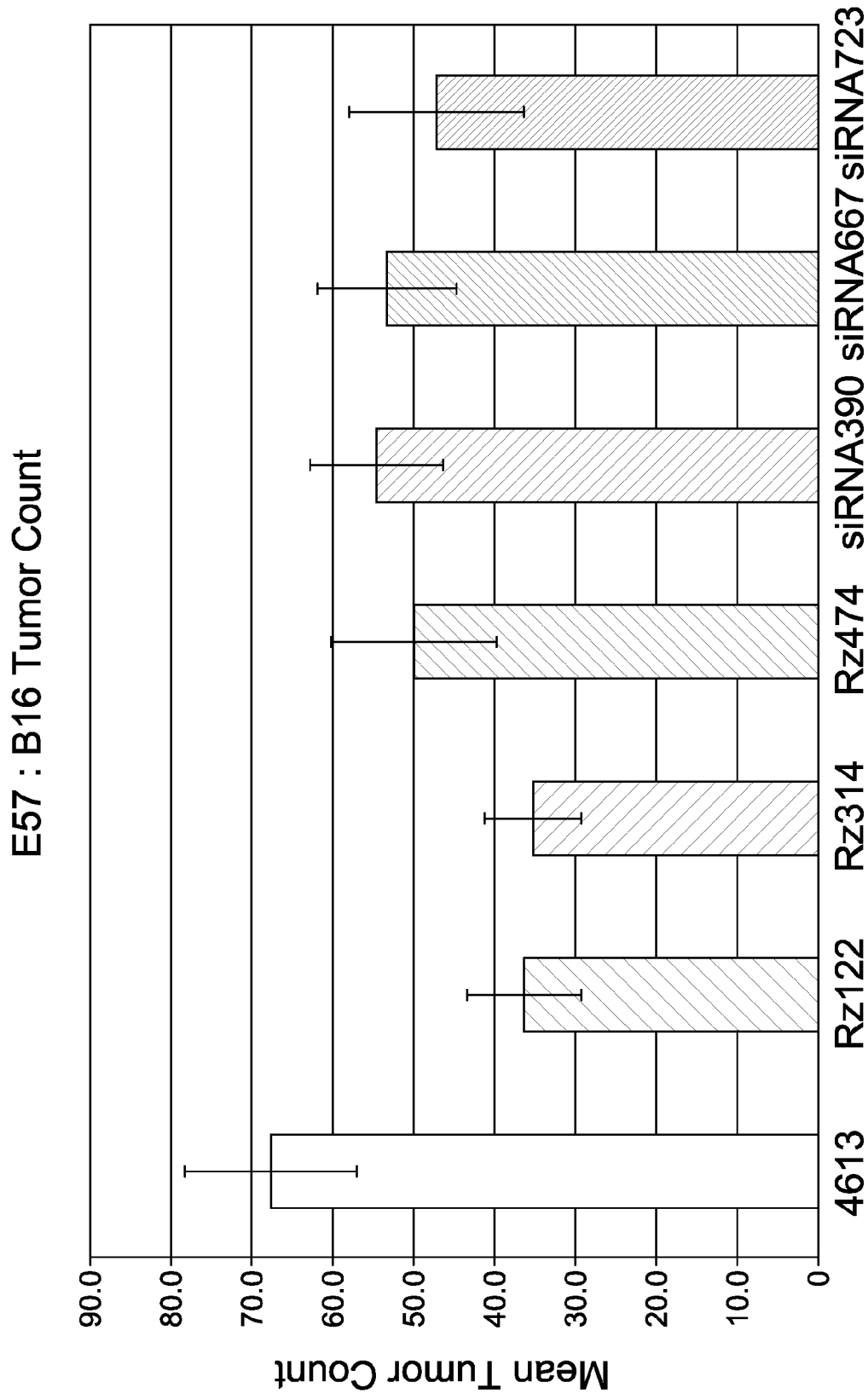
FIG. 12: Anti-metastatic activity of ribozymes (Rz) and siRNAs targeting murine PHIP. B16-F10 melanoma cells were injected intravenously into groups of 10 C57B1/6 mice. On days 3 and 10 following injection, cationic lipid:DNA complexes encoding control vector sequences or three ribozymes and siRNAs targeting different sites of murine PHIP RNA were injected intravenously. Mice were sacrificed on day 25 and analyzed for number of metastatic lung tumors. Two ribozyme (Rz122 and Rz314) and one siRNA (siRNA723) construct demonstrated significant reductions in metastatic tumor burden compared with the control (4613) vector alone (P<0.05).
Figure 13:
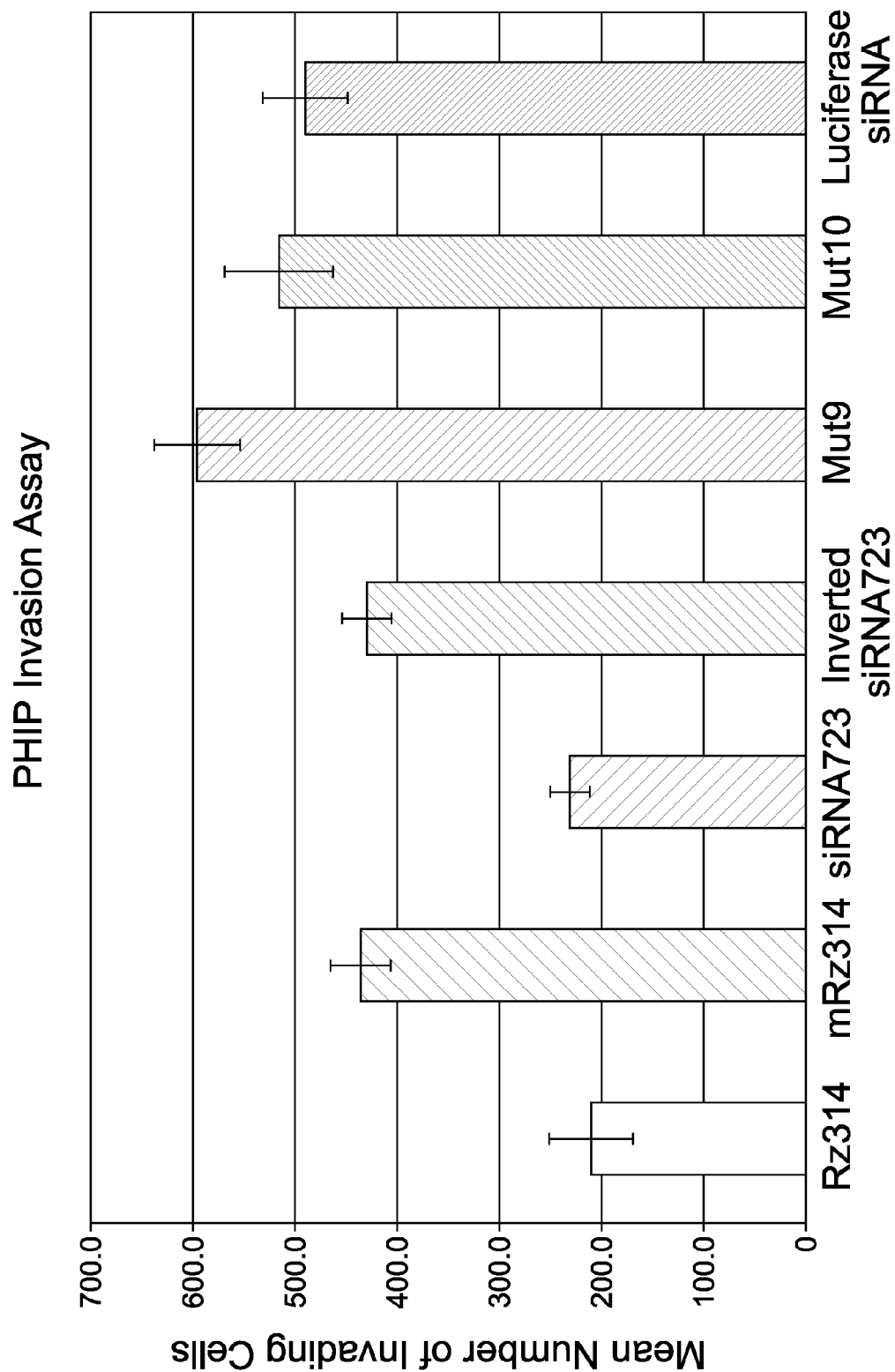
FIG. 13: Targeting PHIP suppresses tumor cell invasion in vitro. B16 cells were transfected with vector expressing Rz314 or siRNA385 targeting murine PHIP, and invasion was determined using a Boyden chamber assay 24 hrs following transfection. There was a significant suppression in B16 invasion by Rz314 when compared with a disabled mutant ribozyme (mRz314), and by siRNA723 when compared with several control, inactive siRNAs.

We have evaluated the role of the PHIP (pleckstrin homology domain interacting protein) gene in the invasive and metastatic phenotype of melanoma. We designed several ribozyme and siRNA inhibitors of murine PHIP, and cloned it into an expression plasmid. Systemic delivery of plasmid-based ribozymes and siRNAs targeting PHIP into C57B1/6 mice bearing metastatic B16 melanoma resulted in the significant suppression of metastatic progression (as evidenced by number of metastatic lung tumors) when injected on days 3 and 10 following tumor cell inoculation. In addition, we examined the mechanism by which PHIP contributes to melanoma progression (FIG. 12). We performed transient transfections of B16 cells with plasmids expressing either the active ribozyme or siRNA described above or control, disabled ribozymes or siRNAs, and examined these transfected cells for invasion into the matrigel assay. These results revealed the significant suppression of invasion by the anti-PHIP siRNA and ribozyme (FIG. 13). Taken together, these results identify a novel pro-invasive and metastatic phenotype for PHIP in melanoma, pointing to PHIP as a rational target for the therapy of melanoma metastasis.

Example 5

Role of Osteopontin in Melanoma

We also examined the prognostic role of osteopontin expression in melanoma. We assessed OPN immunostaining in a tissue microarray containing 350 primary melanoma specimens undergoing sentinel lymph node biopsy, with two years of follow up, or having documented relapse. OPN expression was recorded as 0 (absent), 1 (weak), 2 (moderate), and 3 (intense). By univariate analysis, increasing OPN expression correlated with increased risk of SLN metastasis (as determined by logistic regression), as well as reduced relapse-free (RFS) and overall survival (OS), as determined by Kaplan-Meier analysis. By multivariate logistic regression analysis, increasing OPN (defined as score of 0 versus 1, 2, and 3) expression was independently predictive of SLN metastasis with the inclusion of 6 other known prognostic markers for melanoma. By multivariate Cox regression analysis, high OPN expression (defined as score of 0 and 1 versus 2 and 3) was independently predictive of reduced relapse-free and overall survival (see Tables 8 and 9 below). These results identify OPN as a novel, independent marker of melanoma prognosis given its role in predicting SLN status, RFS, and OS.

TABLE 8

Logistic regression analysis of impact of clinical, histological, and molecular factors on SLN metastasis

| Prognostic factor | Chi-square | P value |
|---|---|---|
| Decreasing age | 15.35 | <.001 |
| Tumor thickness | 10.70 | .001 |
| OPN expression (1, 2, 3 vs. 0) | 7.60 | .006 |
| Clark level | 1.82 | .18 |
| Sex | 1.81 | .18 |
| Site | 0.80 | .37 |
| Ulceration | 0.43 | .51 |

TABLE 9

Cox regression analysis of impact of clinical, histological, and molecular factors on OS of melanoma cohort

| Prognostic factor | Risk Ratio | Chi-square | P value |
|---|---|---|---|
| OPN level (2, 3 vs. 0, 1) | 1.60 | 6.37 | .012 |
| Clark level | 1.68 | 5.84 | .016 |
| Ulceration | 1.55 | 5.77 | .016 |

TABLE 9-continued

Cox regression analysis of impact of clinical, histological, and molecular factors on OS of melanoma cohort

| Prognostic factor | Risk Ratio | Chi-square | P value |
|---|---|---|---|
| Tumor thickness | 1.29 | 5.03 | .025 |
| Site | 1.44 | 3.53 | .06 |
| Age | 1.06 | 1.29 | .26 |
| Sex | 1.065 | .10 | .75 |

Example 6

Copy Number of NCOA3 in Melanoma

Figure 14:
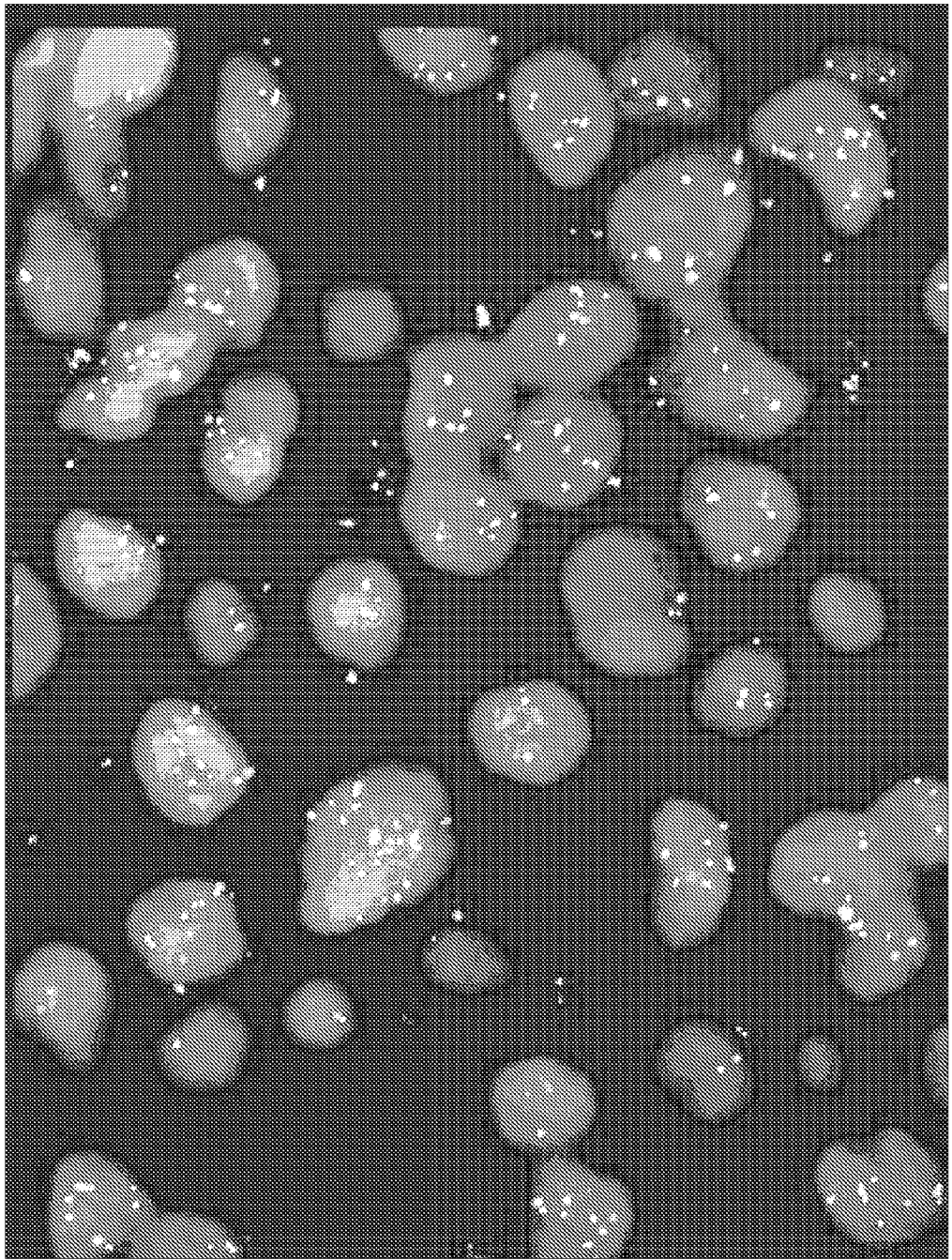
FIG. 14: Determination of the copy number of the NCOA3 gene in melanoma by fluorescence in situ hybridization (FISH).
Figure 15:
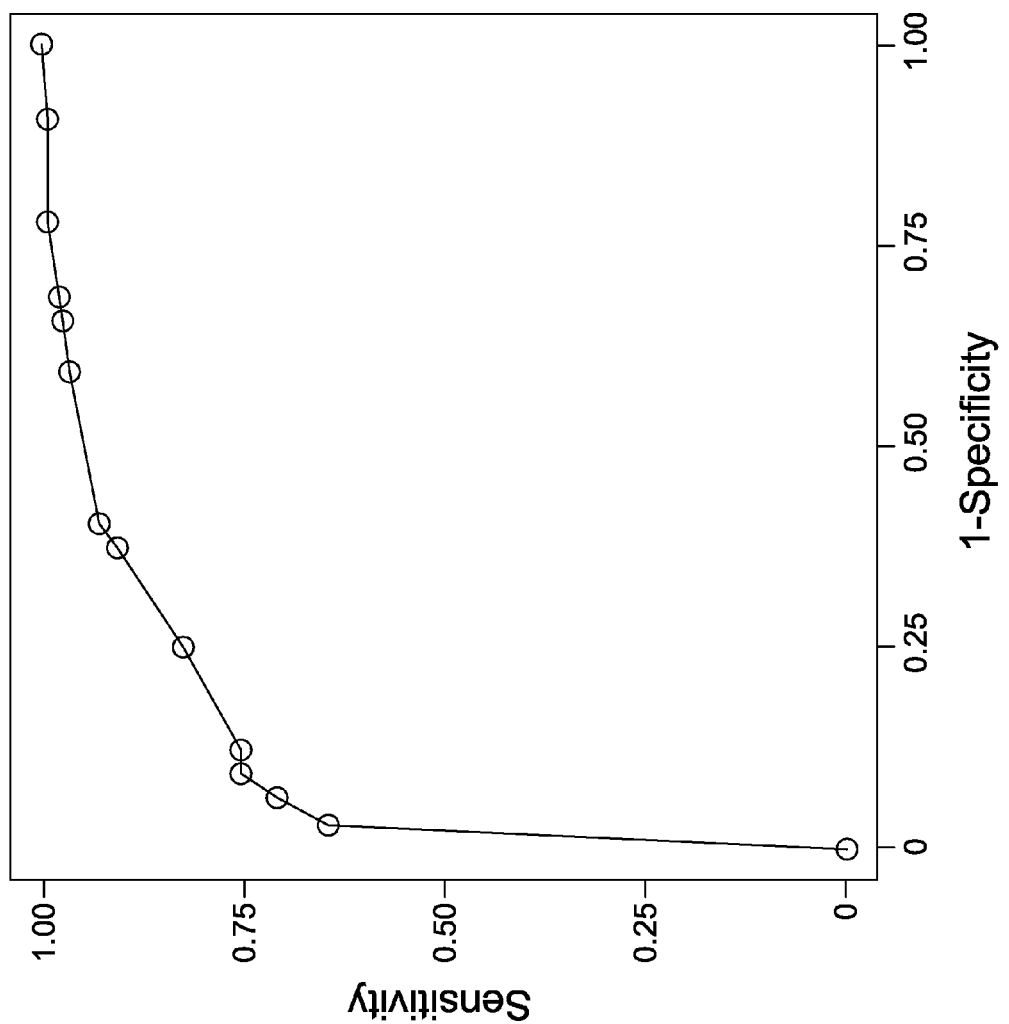
FIG. 15. ROC plot in the diagnosis of melanoma for the multi-marker assay using combined marker intensity scores for all five markers.
Figure 17:
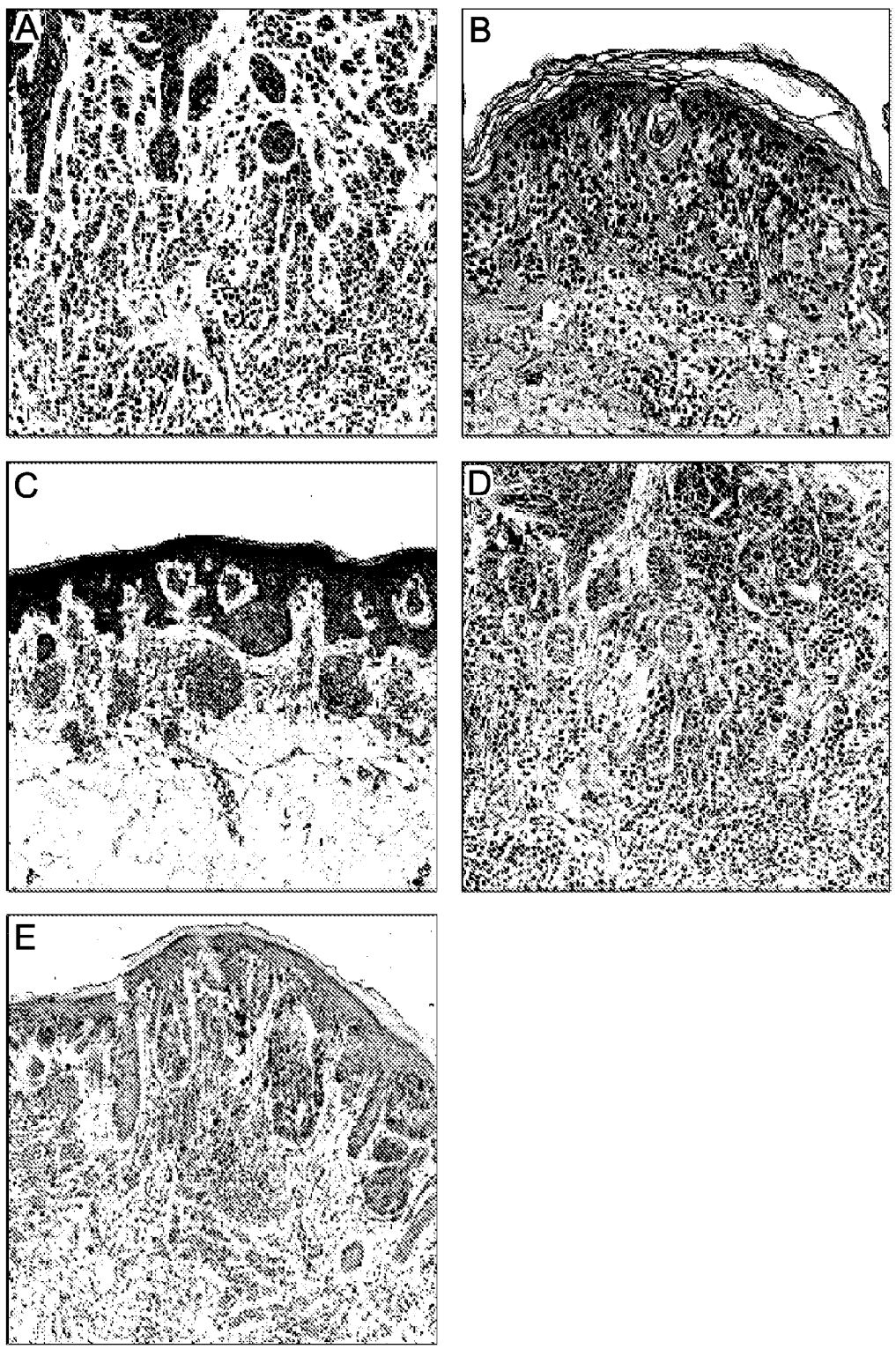
FIG. 17A-E. Representative photomicrographs of immunostaining for ARPC2 (panel A), FN1 (panel B), RGS1 (panel C), SPP1 (panel D), and WNT2 (panel E) in benign nevi.
Figure 18:
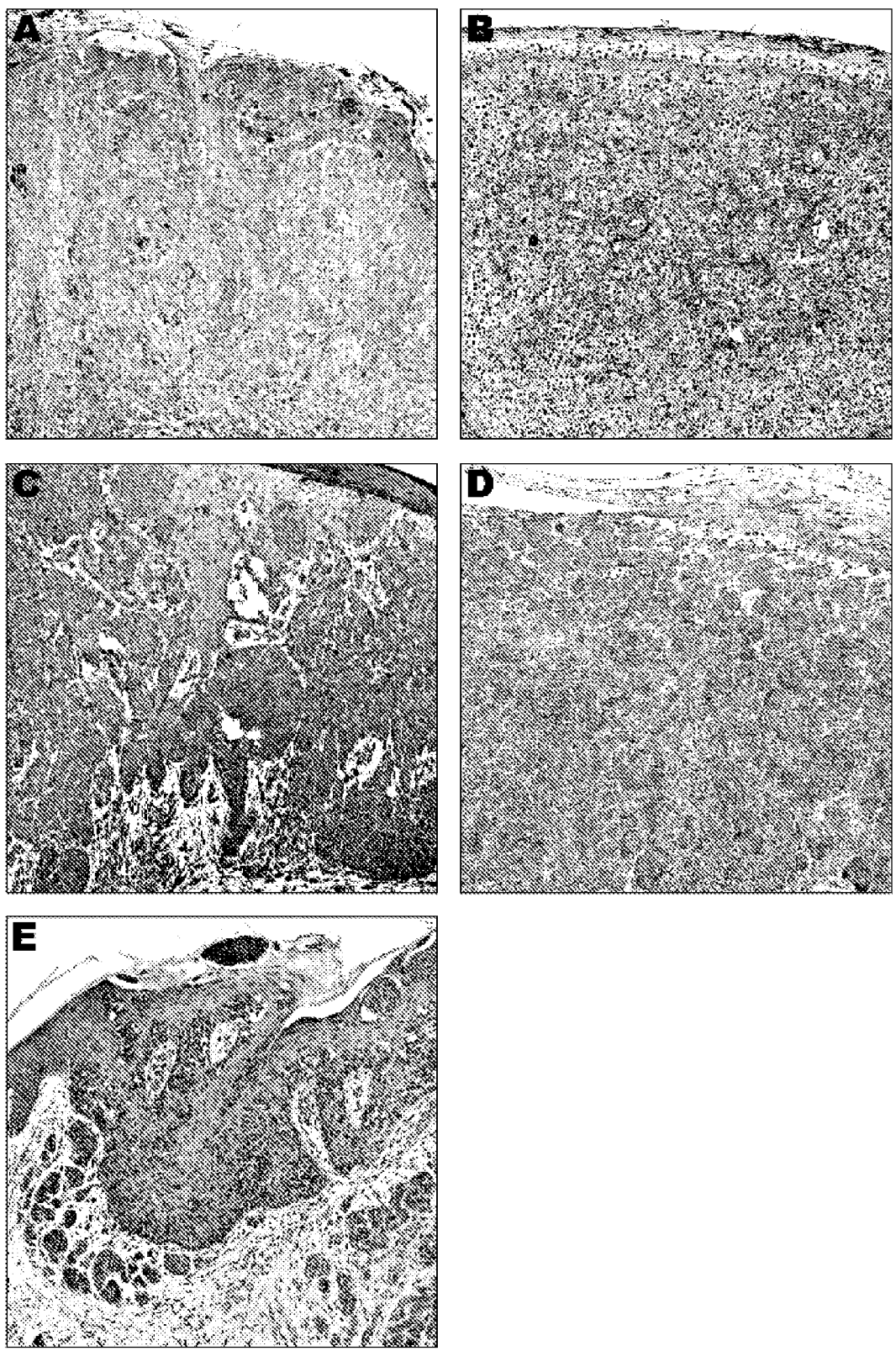
FIG. 18A-E. Representative photomicrographs of immunostaining for ARPC2 (panel A), FN1 (panel B), RGS1 (panel C), SPP1 (panel D), and WNT2 (panel E) in melanomas.
Figure 19:
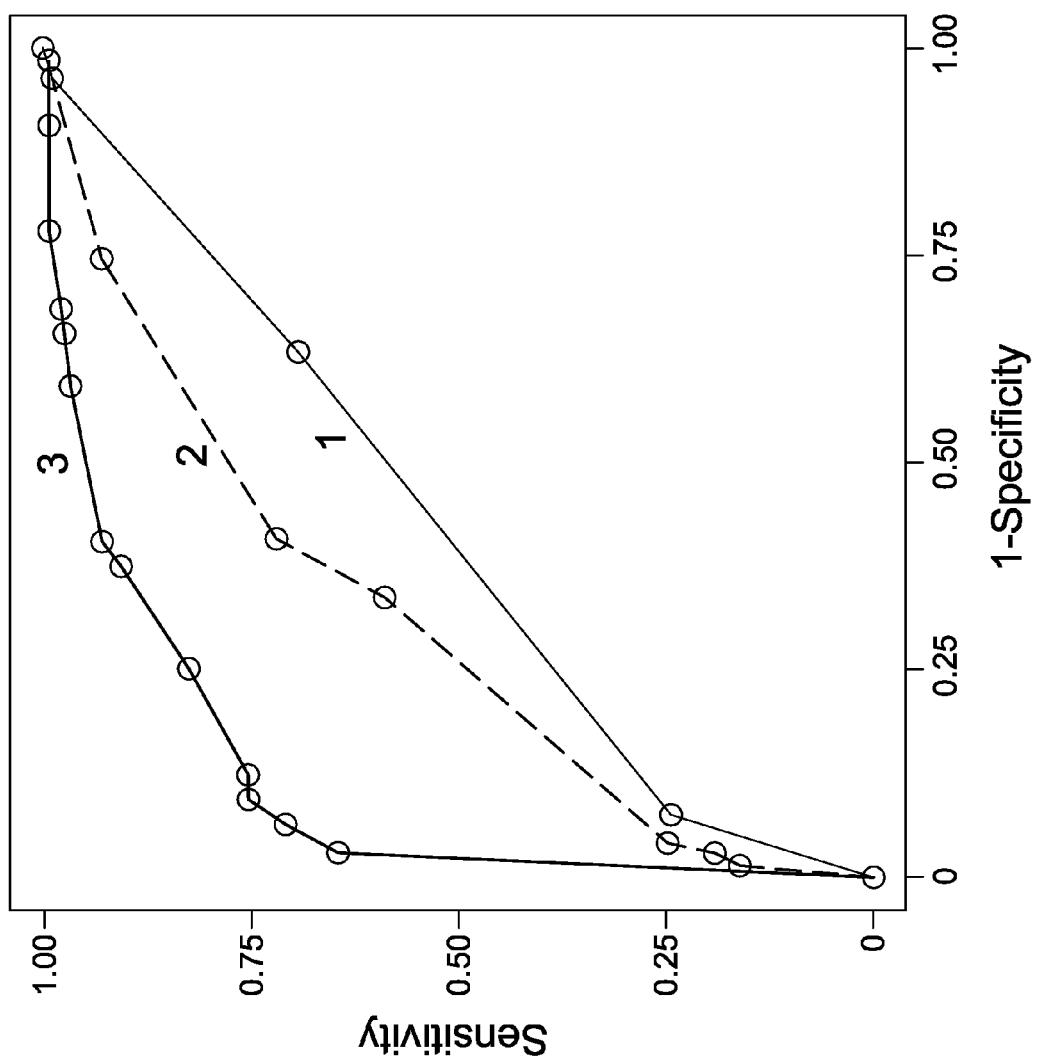
FIG. 19. ROC plots in the diagnosis of melanoma utilizing one marker alone (FN1), three markers (FN1, ARPC2, SPP1), and all five markers.
Figure 20:
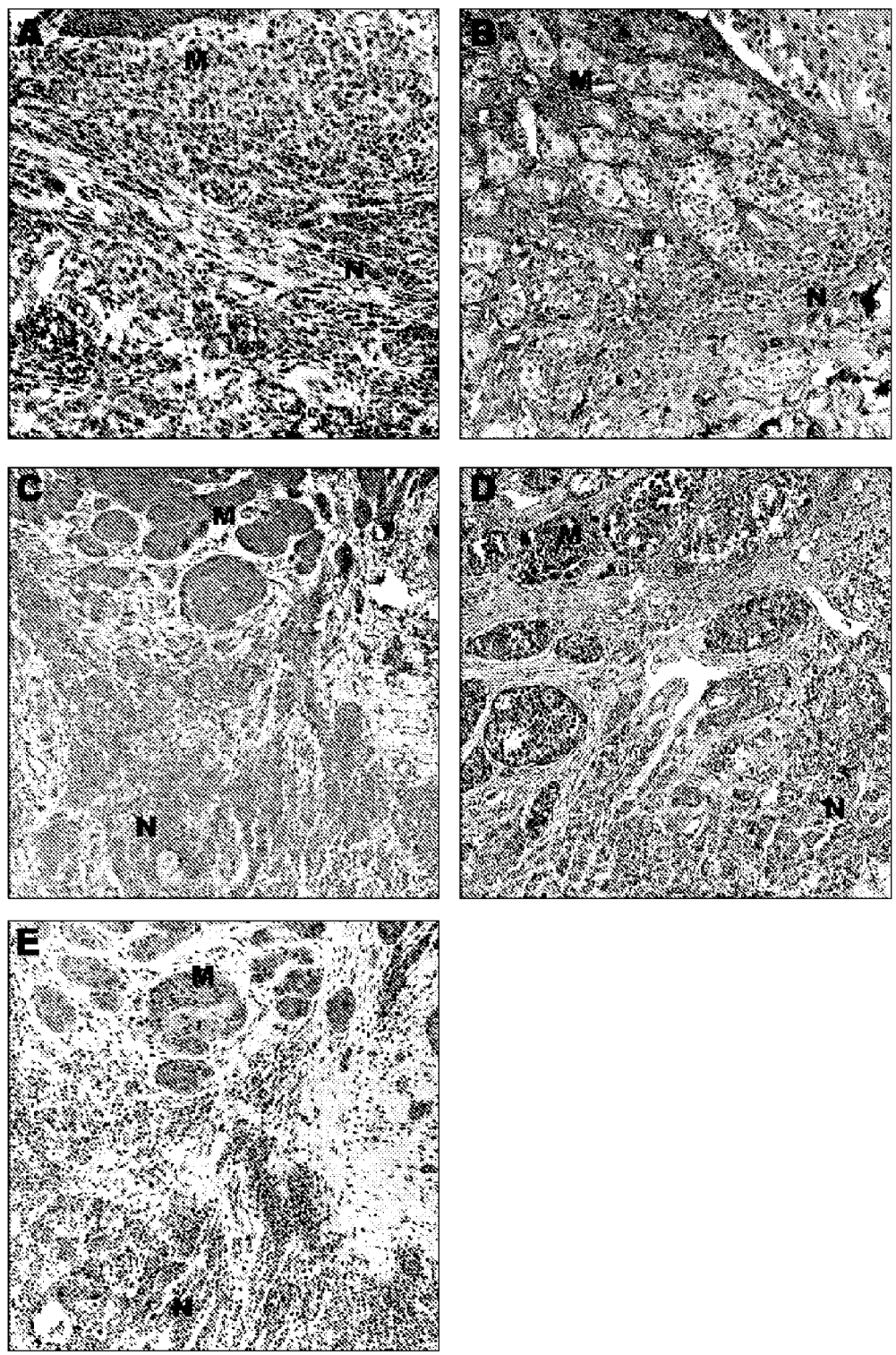
FIG. 20 A-E. Representative photomicrographs of immunostaining for ARPC2 (panel A), FN1 (panel B), RGS1 (panel C), SPP1 (panel D), and WNT2 (panel E) in melanomas arising in association with a nevus, where M represents the melanoma and N represents the nevus.
Figure 21:
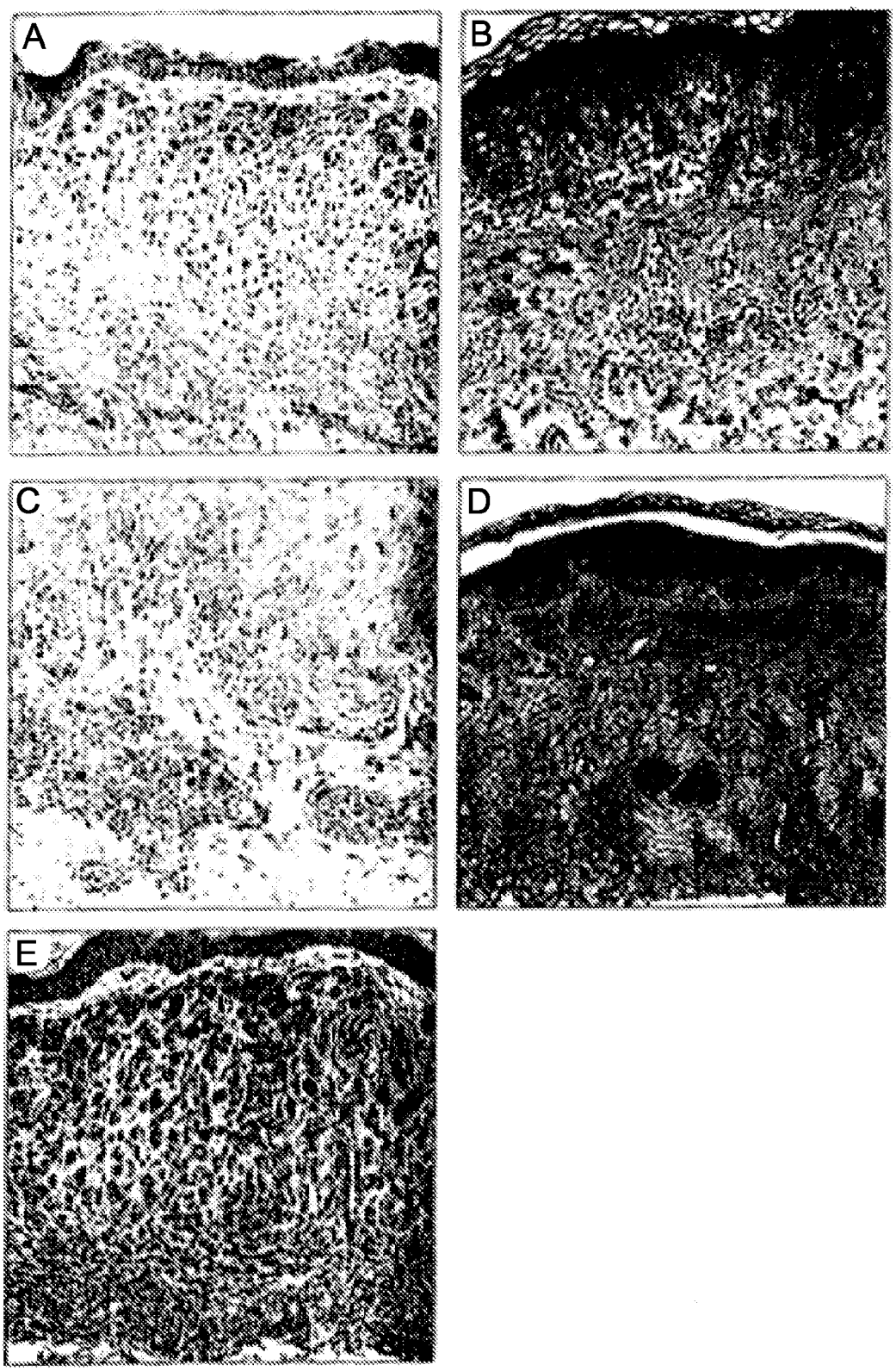
FIG. 21A-E. Immunostaining for misdiagnosed melanocytic neoplasms correctly diagnosed by each of the five markers. A) ARPC2 staining in a 44 year-old female with a 0.76 mm thick, Clark level III, non-ulcerated melanoma initially diagnosed as a benign nevus; B) FN1 staining in a 29 year-old female with a dysplastic nevus initially diagnosed as a 0.25 mm, Clark level II melanoma; C) RGS1 staining in a 31 year-old female with stage 1V metastatic melanoma with a lesion initially diagnosed as an atypical intraepidermal melanocytic proliferation; D) SPP1 staining in a 46 year-old male with a 0.8 mm, Clark level 4, non-ulcerated, desmoplastic melanoma initially diagnosed as a Spitz nevus; E) WNT2 staining in a 44 year-old female with 0.76 mm, Clark level III, non-ulcerated melanoma initially diagnosed as a benign nevus.

We also determined the copy number of NCOA3 in melanoma by fluoresecence in situ hybridization (FISH). We developed a FISH assay to detect NCOA3 expression and analyzed 4 melanoma cases that showed overexpression of NCOA3. Analysis of these cases by FISH showed that each of the cases had high copy numbers of the NCOA3 gene (FIG. 14). This is the first demonstration that elevated copy number of the NCOA3 gene is present in melanoma.

Example 7

RGS1 Expression in Melanoma

The prognostic impact of RGS1 expression on melanoma outcome was examined in a tissue microarray of 301 patients. RGS1 expression was determined using immunohistochemical analysis of archived primary melanoma tumor specimens, and a scored on a four-point scale (0-3) based on staining intensity by a pathologist blinded to the outcome of the patients.

High RGS1 expression correlated with increasing tumor thickness. In tumors with an RGS1 score of 0, the mean tumor thickness was 2.2 mm, which increased to 4.09 mm in tumors with a score of greater than 0 (P<0.00005, T test). In addition, increasing RGS1 expression correlated with increasing tumor vascularity (P=0.045). Increasing RGS1 expression was significantly correlated with SLN status by univariate logistic regression analysis (P=0.04, Chi square statistic 4.12). Increasing RGS1 expression also correlated with increasing SLN burden, as determined by mean number of positive SLNs. Thus, in patients with an RGS1 score of 0, the mean number of SLNs positive was 0.118, which increased to 0.415 in cases with a score of 1 or 2 and 0.723 in cases with a score of 3 (P=0.0055 by ANOVA). By Kaplan-Meier analysis, high RGS1 expression (defined as a score of 2 or 3) was associated with a significantly worsened disease-specific survival (DSS) when compared to cases with low RGS1 expression (score of 0 or 1) (P=0.018, log-rank test).

Multivariate Cox regression analysis showed RGS1 as a significant, independent predictor of outcome associated with melanoma as determined by relapse-free (Table 10), overall (Table 11), and disease-specific (Table 12) survival analyses. By stepwise Cox regression, Clark level, ulceration, and RGS1 expression remained significantly predictive of RFS. By stepwise Cox regression, Clark level, ulceration, site, and RGS1 expression remained significantly predictive of OS. By stepwise Cox regression, thickness and RGS1 expression remained significantly predictive of DSS. With the inclusion of 12 histologic or clinical prognostic factors, RGS1 expression was an independent predictor of RFS (P=0.04), OS (P=0.036), and DSS (P=0.01) on step-wise Cox regression analysis. These results establish RGS1 as a novel, independent prognostic factor for melanoma.

TABLE 10

Cox regression analysis of impact of various factors on relapse-free survival (RFS) of melanoma cohort

| PROGNOSTIC FACTOR | RISK RATIO | CHI-SQUARE | P VALUE |
|---|---|---|---|
| Clark level | 1.97 | 22.9 | <.00005 |
| Ulceration | 2.01 | 14.2 | .0002 |
| RGS level (0, 1, 2, 3) | 1.30 | 6.65 | .0099 |
| Site | 1.29 | 2.01 | .16 |
| Age | .94 | 1.25 | .26 |
| Sex | 1.22 | 1.12 | .29 |
| Tumor thickness | 1.12 | .87 | .35 |

TABLE 11

Cox regression analysis of impact of various factors on overall survival of melanoma cohort

| PROGNOSTIC FACTOR | RISK RATIO | CHI-SQUARE | P VALUE |
|---|---|---|---|
| Clark level | 1.43 | 5.25 | .022 |
| Ulceration | 1.72 | 6.98 | .0083 |
| RGS level (0, 1, 2, 3) | 1.34 | 6.63 | .01 |
| Site | 1.49 | 3.71 | .054 |
| Age | 1.06 | .98 | .32 |
| Tumor thickness | 1.24 | 2.69 | .10 |
| Sex | 1.31 | 1.54 | .22 |

TABLE 12

Cox regression analysis of impact of various factors on disease-specific survival of melanoma cohort

| PROGNOSTIC FACTOR | RISK RATIO | CHI-SQUARE | P VALUE |
|---|---|---|---|
| RGS level (0, 1, 2, 3) | 1.43 | 7.09 | .0077 |
| Clark level | 1.52 | 5.47 | .019 |
| Ulceration | 1.54 | 3.30 | .069 |
| Tumor thickness | 1.29 | 2.74 | .098 |
| Site | 1.29 | 1.22 | .27 |
| Sex | 1.23 | .71 | .40 |
| Age | .98 | .05 | .82 |

Example 8

Two and Three Marker Assay for Prognosis

We analyzed the impact of combined marker expression on melanoma outcome. To begin with, we examined SLN positivity in 309 primary melanoma samples where marker expression was available for both NCOA3 and SPP1. Expression of NCOA3 and SPP1 was graded as high or low based on optimal cutoffs established via logistic regression. High NCOA3 expression was defined as a score of 2 and 3, whereas high SPP1 expression was defined as a score of greater than 0. In cases with low scores for both markers, SLN positivity occurred 0% of the time; this increased to 12.5% in cases with low SPP1 and high NCOA3, 26.7% in cases with low NCOA3 and high SPP1, and 37.0% in cases with high scores for both markers. The incremental impact of marker expression on SLN status was highly significant (two-tailed P value 0.0007). In addition, increasing number of overexpressed markers was significantly predictive of SLN status as determined by univariate logistic regression analysis (Chi-square statistic 14.7, P=0.0001). A univariate logistic regression analysis analyzing the number of markers highly expressed (0, 1, or 2) showed a significant impact on SLN status with increasing marker overexpression (P=0.0004). Next, we examined the impact of combined marker expression on SLN tumor burden, as determined by mean number of positive SLNs. In cases with low scores for both markers, the mean number of positive SLNs was 0; this increased to 0.25% in cases with low SPP1 and high NCOA3, 0.38 in cases with low NCOA3 and high SPP1, and 0.63 in cases with high scores for both markers. The incremental impact of marker expression on SLN tumor burden was also significant (Non-directional Kruskal-Wallis test 0.01; Le directional significance test 0.0066).

Next, the impact of combined marker expression was examined on relapse-free survival (RFS) of melanoma in this cohort. In cases with low scores for both markers, the mean RFS was 0.45 years; this increased to 0.50 in cases with low SPP1 and high NCOA3, 0.55 in cases with low NCOA3 and high SPP1, and 0.56 in cases with high scores for both markers (Le directional significance test 0.0091). In addition, increasing number of overexpressed markers was significantly predictive of RFS as determined by univariate Cox regression analysis (P=0.017). Similarly, there was an impact on overall survival (OS) when marker data were combined. In cases with low scores for both markers, the mean OS was 0.47 years; this increased to 0.51 in cases with low SPP1 and high NCOA3, 0.55 in cases with low NCOA3 and high SPP1, and 0.57 in cases with high scores for both markers (Le directional significance test 0.018). Finally, there was an impact on disease-specific survival (DSS) when marker expression scores were combined. Thus, in cases with low scores for both markers, the mean DSS was 0.47 years; this increased to 0.52 in cases with low SPP1 and high NCOA3, 0.52 in cases with low NCOA3 and high SPP1, and 0.60 in cases with high scores for both markers (P value 0.04 ANOVA, Le directional significance test 0.0069). In addition, increasing number of overexpressed markers was significantly predictive of DSS as determined by univariate Cox regression analysis (P=0.013).

Finally, the impact of combined marker expression scores was analyzed using multivariate analyses. The impact of combined marker expression data on SLN status was analyzed using logistic regression. This analysis showed combined NCOA3/SPP1 status to be the top factor determining SLN status, outperforming the routine histological markers (Table 13 below). By step-wise regression analysis, only combined NCOA3/SPP1 status (P=0.0013), tumor thickness (P=0.0016), and vascular involvement (P=0.039) were significantly predictive of SLN status.

When multiple markers are used, the reagents for these markers may be applied and examined simultaneously, or sequentially, or both. When multiple markers are used, the step of determining the amount of expression can be effected for the markers simultaneously, sequentially or both.

TABLE 13

Cox regression analysis of impact of various factors on SLN status of melanoma cohort

| PROGNOSTIC FACTOR | CHI-SQUARE | P VALUE (TWO-TAILED) |
|---|---|---|
| Combined NCOA3/SPP1 level | 9.08 | .0026 |
| Vascular involvement | 6.05 | .014 |
| Tumor thickness | 3.95 | .047 |
| Clark level | 2.89 | .089 |
| Regression | 2.71 | .10 |
| Microsatellites | 1.38 | .24 |

TABLE 13-continued

Cox regression analysis of impact of various factors on SLN status of melanoma cohort

| PROGNOSTIC FACTOR | CHI-SQUARE | P VALUE (TWO-TAILED) |
|---|---|---|
| Ulceration | .36 | .55 |
| Mitotic rate | .34 | .56 |
| Tumor vascularity | .0024 | .96 |

The impact of combined marker expression score on RFS was examined using multivariate Cox regression. By stepwise regression analysis, combined NCOA3/SPP1 status (P=0.02), Clark level (P=0.0002), ulceration (P<0.00005), mitotic rate (P=0.0003), and microsatellites (P<0.00005) were significantly predictive of SLN status.

Finally, the impact of combined marker expression score on DSS was also examined using multivariate Cox regression. This analysis showed combined NCOA3/SPP1 status to be an independent factor determining DSS when 9 histologic factors were included in the model (Table 14 below). By stepwise Cox regression analysis, microsatellites (P=0.0001), mitotic rate (P=0.0002), ulceration (P=0.0066), and combined NCOA3/SPP1 status (P=0.029) remained significantly predictive of DSS. These results establish the significance of the prognostic impact of combining marker expression scores and demonstrate the utility of a multimarker prognostic assay for melanoma given its independent impact on SLN status, RFS, and DSS. RGS1 will also be tested in a three marker assay with NCOA3/SPP1, with preliminary results showing a significant impact on DSS (Table 15).

TABLE 14

Cox regression analysis of impact of various factors on DSS of melanoma cohort

| PROGNOSTIC FACTOR | RISK RATIO | CHI-SQUARE | P VALUE (TWO-TAILED) |
|---|---|---|---|
| Microsatellites | 3.77 | 14.2 | .0002 |
| Mitotic rate | 1.89 | 5.68 | .017 |
| Combined NCOA3/SPP1 level | 1.69 | 4.32 | .038 |
| Clark level | 1.69 | 2.80 | .09 |
| Vascular involvement | 1.25 | .60 | .44 |
| Regression | .44 | 2.35 | .44 |
| Ulceration | 1.22 | .45 | .50 |
| Tumor thickness | 1.10 | .36 | .55 |
| Tumor vascularity | 1.18 | .33 | .57 |

TABLE 15

Cox regression analysis of impact of various factors on DSS of melanoma cohort

| PROGNOSTIC FACTOR | RISK RATIO | CHI-SQUARE | P VALUE (TWO-TAILED) |
|---|---|---|---|
| Combined NCOA3/SPP1/RGS1 level | 3.33 | 7.48 | .0062 |
| SLN status | 1.80 | 3.93 | .047 |
| Tumor thickness | 1.50 | 3.34 | .068 |
| Clark level | 1.41 | 2.24 | .13 |
| Ulceration | 1.22 | .38 | .54 |
| Gender | 1.14 | .20 | .66 |
| Age | 1.04 | .17 | .68 |
| Location | .96 | .02 | .88 |

Example 9

A Multi-Marker Assay to Distinguish Benign Nevi from Malignant Melanomas

Introduction

This example demonstrates the use of immunohistochemical analysis both to verify the differences in gene expression observed at the RNA level and to test the diagnostic value of this analysis in the differential diagnosis of nevus versus melanoma.

Methods

Study Patients: Several data sets, composed of 699 melanocytic neoplasms, were constructed for the analyses performed in this study: a training set, consisting of a tissue microarray (TMA) of 119 benign nevi and 421 primary melanomas, and four validation sets: tissue sections of 38 melanomas arising in a nevus (resulting in 75 evaluable melanocytic neoplasms); 39 dysplastic nevi; 21 Spitz nevi; and 24 initially misdiagnosed melanocytic neoplasms. The composition of the 119 training set nevi in the TMAs studied is as follows: 31 congenital intradermal nevi; 29 acquired intradermal nevi; 21 acquired dysplastic nevi; 18 congenital compound nevi; 15 acquired compound nevi; 4 junctional nevi; and 1 unclassified nevus. The histologic subtypes of the 421 primary melanomas included in the training TMAs is as follows: 202 superficial spreading melanoma; 135 nodular melanoma; 23 acral melanoma; 18 lentigo maligna melanoma; 16 desmoplastic melanoma; and 27 melanoma not otherwise classified. In the tissue set containing primary melanomas arising in association with a nevus, the breakdown of histologic subtype for nevus and melanoma is as follows: 22 congenital nevi; 8 acquired nevi; 3 acquired dysplastic nevi; 1 acquired compound nevus; 1 acquired intrademial nevus; 1 congenital dysplastic nevus; 1 congenital compound nevus; 1 congenital intradermal nevus; 23 superficial spreading melanoma; 7 nodular melanoma; and 7 melanoma not otherwise classified.

Tissue arrays: Tissue microarrays were generated according to the method described by Kononen J, et al., *Nat Med*, 1998, 4:844-7; and Kashani-Sabet M, et al., *J Clin Oncol*, 2004, 22:617-23. A total of 16 melanoma arrays and a total of 4 nevus arrays were made with an average of approximately 40 tissue cores per array. Melanoma arrays included a total of 673 tissue cores (457 primary melanomas with duplicate cores for 150 patients). Nevus arrays included a total of 138 tissue cores.

Immunohistochemistry: Slides were baked at 60° C. for 30 min prior to staining, and deparaffinized and rehydrated by rinsing in xylene. The slides were then microwaved in 10 mM citrate buffer. Endogenous peroxidase activity was blocked with 3% hydrogen peroxide. In the case of WNT2, after washing with PBS, the slides were incubated at room temperature for 30 minutes with normal rabbit serum to reduce nonspecific background staining, and then washed with PBS. In the case of FN1, the slides were sequentially incubated with Avidin and Biotin blocking reagents. The primary antibody [goat polyclonal anti-WNT2 IgG (Biovision, 1:5 dilution); rabbit polyclonal anti-SPP1 IgG (Abeam, 1:200 dilution); rabbit polyclonal anti-FN1 IgG (Dako, 1:400 dilution); rabbit polyclonal anti-ARPC2 IgG (Upstate, 1:50 dilution); and chicken anti-RGS1 IgG (GeneTex, 1:100 dilution for TMAs and 1:50 dilution for tissue sections)] was then added and incubated overnight at 4° C. Biotinylated goat anti-rabbit, anti-chicken or rabbit anti-goat IgG antibody (Vector Laboratories, Burlingame, Calif.) was used as a secondary antibody for amplification, followed by incubation with ABC- HRP (Vector Laboratories) for 30 min, and DAB/Hydrogen peroxide solution (Sigma). Slides were counterstained with hematoxylin and mounted with permount. Except where noted, the same immunohistochemical staining protocol was utilized for tissue array slides and routine sections.

Evaluation of Immunohistochemical Staining: The regions of most intense staining were scored for each tissue array core and tissue section. Expression of marker proteins was graded on cellular intensity using the following scale: no staining (0), weak staining (1), moderate staining (2), and intense staining (3). Intensity of marker expression was scored both at the junction between epidermis and dermis (junctional zone, or "top") of the neoplasm as well as its base ("bottom"). The locations of "top" and "bottom" in terms of tumor refer to the top of the vertical growth (invasive) tumor and the deepest area of tumor invasion, respectively. In terms of the associated nevi, three standard types of nevi were identified and recorded (see, e.g., Sagebiel R. W., *J Invest Dermatol*, 1993; 100:322 S-325S for classification). In congenital pattern nevi, the top was recorded in the junctional and/or papillary dermal region and the bottom at the deepest identified nevus in the reticular dermis. In acquired pattern nevi, the top was recorded in the junctional region and the bottom at the deepest identified nevus in the papillary dermis. Similarly, in dysplastic nevi, the lateral growth adjacent to the precursor nevus characterizes the random atypia and architectural changes of dysplasia, and the top was recorded in the junctional region and the bottom at the deepest identified nevus in the papillary dermis and/or reticular dermis. Specimens with no melanoma or nevus were excluded from the analysis. Specimens that were not interpretable due to insufficient staining or lack of architectural features were treated as missing observations. The arrays and sections were scored by a pathologist blinded to the identity of the lesions with two separate scorings and a consensus score determined for discrepant scoring for all of the markers. Specificity external positive controls for the various antibodies were as follows: breast tumor (WNT2, SPP1); melanoma cell lines LOX and FEM (WNT2, ARPC2, SPP1); melanoma tissue sections (WNT2, FN1, ARPC2, RGS1, SPP1); normal kidney (FN1); thymus (RGS1) and non-Hodgkin lymphoma (RGS1). The technical negative control used for immunohistochemistry included the use of phosphate buffered saline instead of primary antibody, with all other conditions kept the same.

Statistical Analysis: The diagnostic efficacy of each marker's intensity (at the base of the melanocytic neoplasm) was assessed with univariate logistic regression. The diagnostic efficacy of the intensity of the combination of all five markers was assessed with multivariate logistic regression. For the multi-marker assay, the diagnostic efficacy was analyzed using receiver operating characteristics (ROC) curves and the area under the ROC curve was calculated. Specificity and sensitivity proportions were calculated and analyzed using the Fisher exact test. The difference between intensity of marker immunostaining in the nevus base and in the melanoma base was tested for each marker using the Mann-Whitney test. The difference between intensity of marker immunostaining in the lesion junctional zone and the lesion base was also tested for each marker using the Mann-Whitney test. All P values reported are two-sided.

To assess the reliability of the marker expression scores, the WNT2 intensity scores were compared with the mean densitometric intensity (derived from a quantitative imaging analysis) for each case in the training set. Initially, four sequential ranges of the mean densitometric intensity were identified that corresponded most closely with the 0-3 marker expression scale. Then, the agreement between the WNT2 marker expression scores and their mean densitometric intensity (when both were available) was defined as the percentage of lesions in which both the intensity of marker expression and the mean densitometric intensity were diagnostically equivalent. A similar percentage agreement for WNT2 scores was defined and computed for differences in "top-to-bottom" expression scores.

Based on the data from the 540 lesions in the training set, diagnostic algorithms were obtained from MDMS (Surprise, Ariz.). These algorithms first confirmed a lesion with dysplastic or Spitzoid features to be either a dysplastic or Spitz nevus, and then diagnosed all non-confirmed lesions as either a different type of benign nevus or a melanoma. Separate diagnostic algorithms were obtained for "top-to-bottom" difference scores, by themselves, and for "top-to-bottom" difference scores combined with intensity of expression scores. The final diagnostic algorithm that encompasses each of these algorithms appears in FIG. 2. This final diagnostic algorithm was applied to the lesions in all four validation sets.

Results

We next confirmed the differential protein expression of several of the corresponding transcripts identified in our prior study and examined the utility of a multi-marker diagnostic assay for melanoma in a larger, independent cohort of melanocytic neoplasms. To this end, we amassed a tissue set of 699 melanocytic neoplasms, comprising a training set of TMAs with 540 primary melanomas and melanocytic nevi, and four validation sets comprising tissue sections of 159 melanocytic neoplasms relevant to the differential diagnosis of nevus versus melanoma. Expression of five selected markers (ARC2, FN1, RGS1, SPP1, and WNT2) was initially analyzed in the training set using commercially available antibodies targeting the aforementioned proteins. Each marker was scored on a four-point scale for staining intensity.

In the process of optimizing the immunohistochemical staining of the markers, an intriguing staining pattern in benign nevi was observed. Benign nevi showed a systematically stronger staining in the junctional zone of the nevus, with loss of expression at the nevus base). By contrast, expression of the markers was more uniform in the invasive portions of melanomas in the comparison between the lesional junctional zone and base. As a result, we scored the TMAs for intensity of expression both at the junctional zone ("top") as well as at the base ("bottom") of each melanocytic neoplasm in which the orientation of the lesion was clearly demonstrable on the specimen core represented on the arrays.

Initially, each of the five markers was evaluated individually for its ability to diagnose melanoma versus nevus, using the four-point intensity scale applied to the base of each lesion. The best way to partition each marker's four-point scale was identified (shown in Table 16). The best scale partitioning method was defined as the one that maximized the resulting Chi-square value associated with its univariate logistic regression analysis. The capacity of each optimally partitioned marker to discriminate between nevi and melanomas was also assessed according to its diagnostic sensitivity and specificity proportions. Each of the five molecular markers was shown to be significantly overexpressed in melanomas when compared with nevi (Table 16).

Several analyses were performed to examine whether the combination of markers was useful in its ability to diagnose melanoma. Specifically, we examined an analysis focusing on the intensity of bottom expression scores alone, one focusing on the difference in expression between lesion junctional zone and base ("top-to-bottom" analysis), and a third analysis encompassing both types of data.

To begin with, we performed an analysis examining the intensity of expression scores assigned to the base of each lesion for the five markers combined. Optimally partitioned marker expression scores were combined via multiple logistic regression, and a probability of being malignant was assigned to each of the lesions for which complete data were available. Assigned probabilities were then partitioned at their optimal point of separation, achieving a specificity of 93.6% and a sensitivity of 75.8% (P<0.00005, Fisher exact test). In addition, a receiving operator characteristics (ROC) curve was constructed for this multi-marker analysis and is shown in FIG. 1, with an associated area under the curve (AUC) of 0.9105.

For illustrative purposes, we replicated this analysis for each of the markers individually, and for combinations of 3 markers. Analysis of a single marker (e.g., FN1) showed the smallest AUC of 0.5622, which increased to an intermediate level of 0.7036, when two additional markers were included (ARPC2 and SPP1), culminating in the AUC of 0.9105, when all five markers were included in the model.

Secondly, we performed an analysis utilizing only the differences in "top-to-bottom" marker expression for all five markers. Analysis of marker expression in the lesion junctional zone versus base showed that nevi consistently lost expression for each of the five markers when compared with melanomas, in which the marker immunostaining was much more uniform. This pattern of noticeably different "top-to-bottom" marker expression between nevi and melanomas was replicated for each of the five markers, when analyzed by the Mann Whitney test (data not shown), with specificity and sensitivity for each marker indicated in Table 17. In fact, in the case of one marker, WNT2, there was perfect separation of the two distributions of "top-to-bottom" difference scores between nevi and melanomas in the 144 lesions analyzed. Thus, every news analyzed lost expression from its junctional zone to its base, whereas every melanoma had uniform expression from the junctional zone to its base. This perfect discrimination between nevus and melanoma in the case of WNT2 rendered impossible further reliance on logistic regression as our sole analytical tool. The logistic regression estimation procedure cannot produce maximum likelihood estimates of the regression coefficients in the face of such perfect discrimination. Thus, in order to analyze the diagnostic validity of pattern of marker expression, when all five markers were combined, a diagnostic algorithm was obtained that consisted of 14 discriminatory criteria. The first four criteria focused on confirming (or not) whether a lesion with dysplastic features really was a dysplastic nevus. The remaining ten criteria focused on difference in vertical expression scores of non-dysplastic lesions determined to be directionally consistent by the above-referenced Mann Whitney tests. Application of this diagnostic algorithm to the 540 lesions in the training set yielded a specificity of 84.6% and a sensitivity of 98.7% (P<0.00005, Fisher exact test).

In order to address the reliability of the expression scores and the "top-to-bottom" differences, a quantitative imaging analysis was performed. The WNT2-stained lesions in the training set were scanned digitally and mean densitometric intensity was calculated for each lesion. The concordance between the marker intensity scale and mean densitometric intensity was 90.3% when calculated as the percentage of identically diagnosed lesions, using corresponding cut-points for diagnosing melanoma (P<0.00005, Mann Whitney test). We also evaluated the concordance in differences in the "top-to-bottom" expression scores, and observed a 98.4% agreement between the marker intensity scores and the mean densitometric analysis (P<0.00005, Mann Whitney test).

Logistic regression analysis of the mean densitometric intensity scores alone reproduced the diagnostic accuracy of WNT2 (P<0.00005) identified by marker intensity scores. In addition, a "top-to-bottom" analysis of WNT2 mean densitometric intensity scores showed a specificity of 97.1%, with a sensitivity of 96.6%, reproducing the results found by marker expression scores.

Finally, we aimed to explore the utility of the multi-marker assay to diagnose melanoma using both marker expression scores as well as "top-to-bottom" differences. Once again, given the perfect separation in vertical expression scores for WNT2, we were unable to use logistic regression. Thus, an algorithm was obtained using both data from the intensity of expression scores as well as the differential expression in the lesion junctional zone versus base (shown in FIG. 2) to discriminate between nevus and melanoma. Intriguingly, when marker expression in the nevi was examined, all of the 21 dysplastic nevi included in the training set were identifiable just on the basis of their ARPC2 and FN1 intensity of expression scores. A separate algorithm was therefore developed to confirm as actually dysplastic all nevi with dysplastic features. This confirmatory algorithm contained four discriminating criteria based on ARPC2 and FN1 expression intensity. The algorithm for dysplastic nevi was then combined with an algorithm based on "top-to-bottom" differences, as well as marker expression scores. Application of this final diagnostic algorithm to the training set achieved a specificity of 94.9% and a sensitivity of 90.6% in the diagnosis of melanoma (P<0.00005, Fisher exact test). Additional analyses were conducted using this diagnostic algorithm alone.

To validate the multi-marker assay developed in the training set, we examined both the intensity and pattern of expression of the five markers for their expression in four distinct validation sets with greater relevance to the histological distinction between nevus and melanoma. In the TMAs we had aimed to amass a large cohort of melanocytic neoplasms, both to validate the differential expression of the markers derived from cDNA microarray analysis as well as to examine the utility of our multi-marker assay. However, certain nevus subtypes do not present a differential diagnostic dilemma, and certain melanoma subtypes do not arise from pre-existing nevi.

In order to validate our results from the training set, an optimal setting to evaluate potential differences in expression were cases of melanoma arising in association with pre-existing nevi, for which many potential confounding factors (age, gender, anatomical location, and potentially irrelevant histologic subtypes of nevus and melanoma, among others) are automatically controlled. Thus, we amassed a validation set of 38 cases of primary melanoma in association with a nevus, resulting in 75 evaluable melanocytic neoplasms. In addition, we collected two additional validation sets directly relevant to this histological differential diagnosis: 21 cases of Spitz nevus; and 39 cases of dysplastic nevus. These are the two most commonly problematic nevus subtypes in the histological differential diagnosis of nevus versus melanoma. Finally, we examined marker expression in a data set of 24 previously misdiagnosed lesions, including 6 lesions initially diagnosed as melanoma that were subsequently diagnosed as nevus by a consensus dermatopathology review, and 18 lesions initially diagnosed as nevus that subsequently recurred locally and/or metastasized and were retrospectively diagnosed as melanoma. In all of the validation sets, in view of the importance of marker expression at the nevus junctional zone versus nevus base, we examined marker expression using immunohistochemical analysis on 5 μM tissue sections.

Utilizing the algorithms with both intensity of marker expression score as well as the differences in "top-to-bottom" expression scores, the multi-marker assay achieved a 94.7% specificity and 97.3% sensitivity in diagnosing melanoma in the 75 melanomas arising in a nevus (Supplementary Figure xx). In addition, the algorithm developed from the analysis of dysplastic nevi on the TMA correctly identified 94.9% (37/39) of dysplastic nevus sections and 95.2% (20/21) of Spitz nevi. Finally, the multi-marker assay correctly diagnosed 18/24 (75.0%) of the previously misdiagnosed lesions. When the various sets of training and validation melanocytic neoplasms were combined, the multi-marker assay yielded a specificity of 95.1% and a sensitivity of 90.5% (P<0.00005, Fisher exact test). A comparison of the sensitivity, specificity, and AUC of the multi-marker assay in the various data sets and using various diagnostic algorithms is presented in Table 18.

Discussion

This example discloses a multi-marker molecular assay to distinguish melanoma from benign nevus using five biomarkers that were suggested by a recent cDNA microarray analysis. In that analysis, unsupervised hierarchical cluster analysis correctly separated nevus from melanoma in a small number of freshly available melanocytic neoplasms on the basis of gene expression profiles, and demonstrated a large gene set that was differentially expressed in melanomas versus nevi (see Haqq C. et al. *Proc Natl Acad Sci USA,* 2005; 102:6092-7). In this example, we validated the differential expression of five of the genes suggested by that analysis, and tested the utility of a multi-marker assay to diagnose melanoma versus nevus. This multi-marker immunohistochemical assay showed a specificity of 94.9% and a sensitivity of 90.6% in a training set comprised of a TMA containing a large number of nevi and primary melanomas. On the basis of this analysis, the multi-marker diagnostic assay was then subjected to four different validation sets with direct relevance to the differential diagnosis of nevus versus melanoma, and was able to accurately diagnose a high percentage of melanomas arising in a nevus, Spitz and dysplastic nevi, as well as previously misdiagnosed melanocytic neoplasms. In the combined data set, the multi-marker assay yielded a specificity of 95.1% and a sensitivity of 90.5% in the diagnosis of melanoma.

Our results demonstrate that a multi-marker assay comprised of ARPC2, FN1, RGS1, SPP1, and WNT2 protein expression levels can be useful in the differential diagnosis of nevus versus melanoma, which represents one of the most daunting tasks in pathology. Our study is the largest to date analyzing the utility of molecular markers in melanoma diagnosis, and unique in utilizing a comprehensive set of tissues necessitated by the histological heterogeneity of both nevi and melanomas. The multi-marker assay corrected three-quarters of the cases in which incorrect pathological diagnoses had been rendered, including melanomas initially misdiagnosed as a nevus, in which the clinical behavior of the lesion had initiated review of the prior pathology report. Thus, the multi-marker assay described here can be used to assist in the histological diagnosis of melanoma, thereby providing important new information to pathologists and other clinicians responsible for caring for patients with ambiguous melanocytic neoplasms.

An important advantage of this invention is that mistakes in melanoma diagnosis can be avoided. Such mistakes cause many patients to undergo inappropriate therapy. Furthermore, the misdiagnosis of melanoma is the second most common reason for cancer malpractice claims in the United States, second only to mistakes in breast cancer diagnosis (see Troxel D. B., *Am J Surg Pathol,* 2003; 27:1278-83). Patients mistakenly diagnosed with a melanoma are under permanent fear of relapse and may not be able to obtain life insurance, whereas patients mistakenly diagnosed with a nevus are deprived of appropriate therapy for their malignancy, potentially including sentinel lymph node biopsy and systemic adjuvant therapy. Our results demonstrate that the multi-marker assay could reverse (and therefore potentially prevent) a high percentage of errors caused by the routine histological analysis of melanocytic neoplasms.

The differential expression of the markers suggested by the cDNA microarray analysis was not uniform in the immunohistochemical analysis of the nevus, as the nevus junctional zone frequently expressed the markers at a higher level than the nevus base. This was in stark contrast to most melanomas, which showed uniformity in the "top-to-bottom" analysis of marker expression. As a result, the pattern of protein expression was a significant discriminator between nevus and melanoma and, in general, superior to absolute transcript expression scores. While our results confirm the differential expression of the genes first identified by the transcriptome analysis, they refine the information gained by that analysis by demonstrating that the greatest difference in gene expression lies at the base of the melanocytic neoplasm.

One of the reasons why we selected immunohistochemistry to validate the cDNA microarray results as opposed to other, potentially more quantitative assays such as quantitative PCR, was the ability of immunohistochemistry to provide in situ analysis of gene expression for the lesion in question. Our results describe the utility of a molecular assay that could be developed as an adjunct to the histopathological analysis of nevi and melanomas.

While immunohistochemical analysis is by its very nature semi-quantitative, we assessed the reliability of observer marker intensity scores using a quantitative imaging analysis. We found a high concordance rate (>90%) between the diagnostic accuracy of observer marker intensity scores and mean densitometric intensity determined from the quantitative analysis, and an even higher concordance rate (98%) in differences in "top-to-bottom" expression scores. Given that a diagnostic algorithm focusing only on the lesion junctional zone vs. base scores yielded a specificity of 84.6% and sensitivity of 98.7% in the training set, our results suggest the potential ease with which analysis of these markers could be applied to the diagnosis of melanocytic neoplasms in the clinical setting.

While a vertical decrease in immunostaining has been observed with a few other markers, including S100A6, Melan-A, and HMB-45, these markers have no value in distinguishing between nevi and primary melanomas, because they were not differentially expressed in nevi versus melanomas (see Busam K J., et al., *Am J Surg Pathol.,* 1998, 22:976-82; Fullen D. R., et al., *J Cutan Pathol,* 2001; 28:393-9; Kucher C., et al., *Am J Dermatopathol,* 2004; 26:452-7; Haqq C. et al., *Proc Natl Acad Sci USA* 2005; 102:6092-7). In addition, in some of these studies, intradermal nevi were the dominant nevus type examined. Intradermal nevi are known to undergo significant "maturation" at their base. In our study, the downregulation of marker immunostaining was observed at the base of intradermal nevi, compound nevi, as well as Spitz and dysplastic nevi. This indicates the more broad-based utility of this multi-marker assay as a molecular diagnostic marker for melanoma.

In this example, we describe a multi-marker immunohistochemical assay that can diagnose melanocytic neoplasms with a high degree of accuracy, thus aiding in this difficult pathological differential diagnosis.

TABLE 16

Discrimination of melanoma from nevus with the
use of single marker expression scores alone

| Marker | Optimal Scale Partitioning | Chi-Square | P-Value |
|---|---|---|---|
| ARPC2 | 0 vs. 1, 2 vs. 3 | 24.2 | <.00005 |
| FN1 | 0 vs. 1, 2 vs. 3 | 4.75 | .0294 |
| RGS1 | 0, 1, 2 vs. 3 | 8.98 | .0027 |
| SPP1 | 0, 1 vs. 2, 3 | 11.1 | .0009 |
| WNT2 | 0, 1, 2, 3 (entire scale) | 86.6 | <.00005 |

TABLE 17

Diagnostic accuracy for melanoma using lesion junctional
zone versus lesion base ("top-to-bottom") score
in training data for each individual marker

| Marker | Specificity (%) | Sensitivity (%) | P-Value (Fisher exact test) |
|---|---|---|---|
| ARPC2 | 59.7 | 96.1 | <.00005 |
| FN1 | 23.3 | 98.9 | .0101 |
| SPP1 | 61.5 | 99.0 | <.00005 |
| RGS1 | 33.3 | 99.0 | <.00005 |
| WNT2 | 100 | 100 | <.00005 |

TABLE 18

Comparison of sensitivity, specificity, and AUC of multi-
marker assay for melanoma diagnosis in various tissue
sets and using different diagnostic algorithms*

| Data Set | Diagnostic Algorithm | Specificity (%) | Sensitivity (%) | AUC |
|---|---|---|---|---|
| Training | Marker Intensity Alone | 93.6 | 75.8 | .9105 |
| Training | Vertical Expression Alone | 84.6 | 98.7 | .9165 |
| Training | Combined Expression Scores | 94.9 | 90.6 | .9277 |
| Training and Validation | Combined Expression Scores | 95.1 | 90.5 | .9275 |

*P value for every analysis <.00005 (Fisher exact test)

Example 10

A Six-Gene Diagnostic Marker Assay for Melanoma

Figure 22:
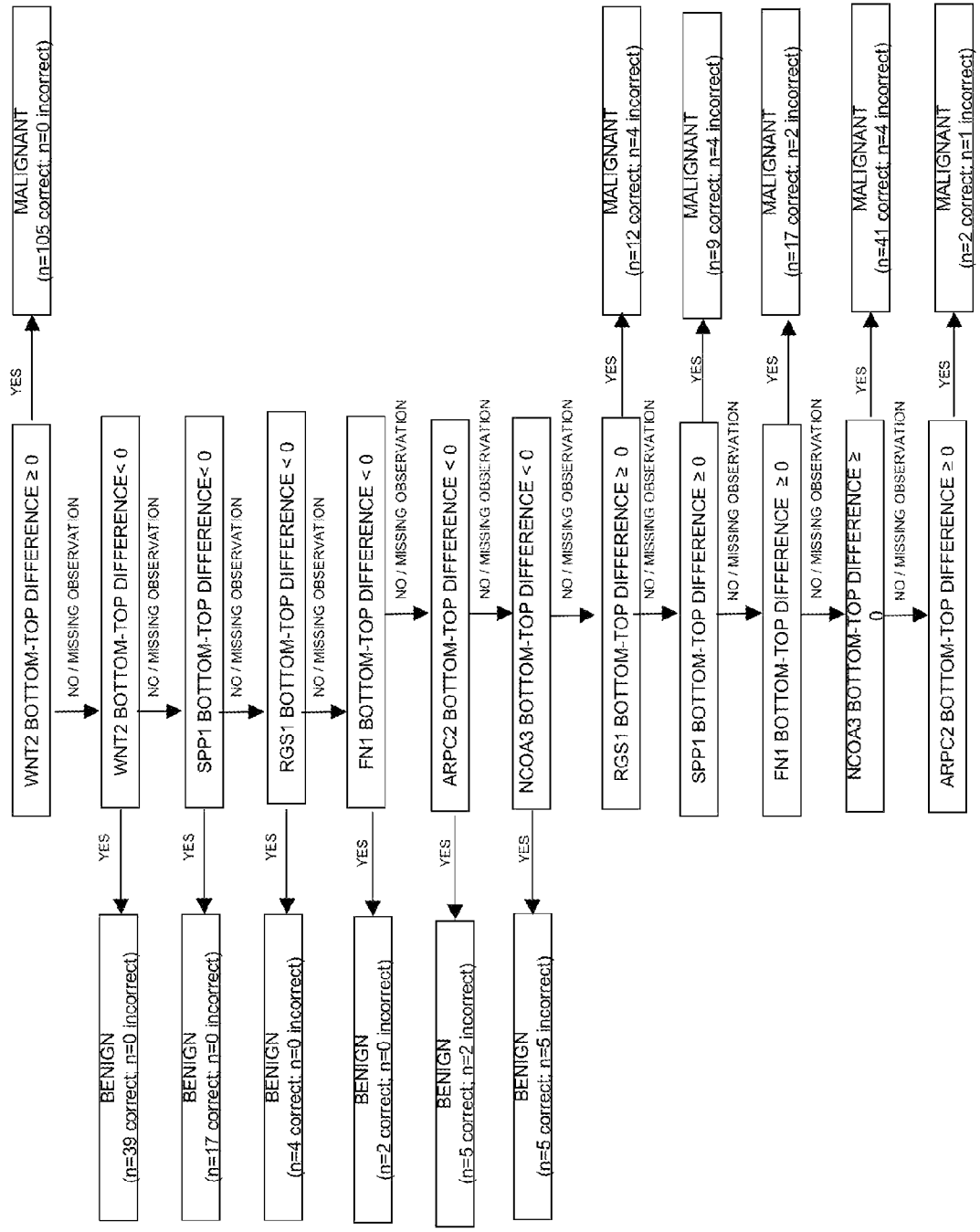
FIG. 22. Diagnostic algorithm using differences in top-to-bottom scores for six-gene diagnostic assay for melanoma.

We evaluated the utility of a six-gene assay in the differential diagnosis of melanoma versus nevus in a combined data set of 698 patients comprising a training set of 538 patients (119 nevi and 419 melanomas) and a validation set of 160 patients. The expression of six genes (ARPC2, FN1, NCOA3, RGS1, osteopontin (SPP1), and WNT2) was evaluated using immunohistochemical analysis. By logistic regression analysis, the six-gene assay (when analyzed by marker expression scores alone) showed a sensitivity of 77.9% and a specificity of 92%, with an AUC under the ROC of 0.914. A diagnostic algorithm was developed to examine the utility of top-to-bottom scores for the six markers in the diagnosis of melanoma (FIG. 22). This top-to-bottom analysis only (in which marker expression was uniformly lost in nevi whereas this vertical expression was maintained in the melanomas) revealed a sensitivity of 96.4% and a specificity of 82.8%. Finally, a diagnostic algorithm was developed that encompassed both marker intensity scores as well as top-to-bottom differences (FIG. 23). Application of this diagnostic algorithm to the training set lesions yielded a sensitivity of 92% and a specificity of 94.1%. Finally, this same diagnostic algorithm was applied to the four validation sets, and revealed a sensitivity of 97.4% and a specificity of 94.7% in melanomas arising in a nevus, and correctly identified 37/39 (95%) of dysplastic nevi, 20/21 (95%) Spitz nevi, and 18/24 (75%) of previously misdiagnosed neoplasms. In the combined data set, the multi-marker assay revealed a sensitivity of 92.2% and a specificity of 94.6%. These results demonstrate the utility of this six-marker assay in the diagnosis of melanomas as well as nevi.

Example 11

A Four-Gene Prognostic Assay for Melanoma

We examined the prognostic impact of RGS1, NCOA3, osteopontin (SPP1), and PHIP when expression levels for all four markers were combined. We developed a prognostic index that reflected the number of markers overexpressed (defined as being above the cutpoint for that markers) for each of 412 cases of primary cutaneous melanoma present on the TMA for which marker expression was available. Initially, impact of multi-marker positivity was analyzed by univariate analysis on three important outcome parameters: sentinel lymph node status (SLN status), relapse-free survival (RFS), and disease-specific survival (DSS). By univariate analysis, increasing number of markers overexpressed was significantly predictive of SLN status (P=0.002, logistic regression), RFS (P<0.0001, Cox regression), and DSS (P<0.0001, Cox regression).

Next, the multi-marker index was analyzed for its prognostic impact by multi-variate analysis, utilizing the six factors included by the AJCC melanoma committee analysis. By multivariate analysis, the multi-marker assay was an independent predictor of SLN status (Table 19), RFS (Table 20), and DSS (Table 21) with the inclusion of these factors. In the analysis of DSS, the multi-marker assay emerged as the top factor predicting DSS. The multi-marker index remained significantly predictive even with the inclusion of SLN status (Table 22). In addition, increasing marker positivity was significantly predictive of RFS (P<0.0001) and DSS (P<0.0001) by Kaplan-Meier analysis. These results demonstrate the powerful prognostic impact of the multi-marker assay.

TABLE 19

Cox regression analysis of impact of various
factors on SLN status of melanoma cohort

| PROGNOSTIC FACTOR | CHI-SQUARE | RISK RATIO | P VALUE |
|---|---|---|---|
| Age | 19.60 | 0.65 | <.0001 |
| Multi-marker expression level | 8.35 | 1.33 | .0039 |
| Tumor thickness | 6.89 | 1.68 | .0087 |
| Clark level | 1.63 | 1.36 | .20 |
| Sex | 1.49 | 1.46 | .22 |
| Ulceration | .77 | 1.32 | .38 |
| Site | .0006 | 1.01 | .98 |

TABLE 20

Cox regression analysis of impact of various
factors on RFS of melanoma cohort

| PROGNOSTIC FACTOR | CHI-SQUARE | RISK RATIO | P VALUE |
|---|---|---|---|
| Clark level | 25.15 | 1.81 | <.0001 |
| Multi-marker expression level | 15.52 | 1.19 | .0001 |

TABLE 20-continued

Cox regression analysis of impact of various factors on RFS of melanoma cohort

| PROGNOSTIC FACTOR | CHI-SQUARE | RISK RATIO | P VALUE |
|---|---|---|---|
| Ulceration | 13.20 | 1.79 | .0003 |
| Site | 3.53 | 1.34 | .06 |
| Tumor thickness | 1.18 | 1.11 | .28 |
| Age | .30 | 0.97 | .59 |
| Sex | 0 | 1.00 | .999 |

TABLE 21

Cox regression analysis of impact of various factors on DSS of melanoma cohort

| PROGNOSTIC FACTOR | CHI-SQUARE | RISK RATIO | P VALUE |
|---|---|---|---|
| Multi-marker expression level | 14.18 | 1.24 | .0002 |
| Clark level | 8.16 | 1.55 | .0043 |
| Ulceration | 4.23 | 1.52 | .04 |
| Tumor thickness | 3.89 | 1.29 | .049 |
| Site | 2.66 | 1.40 | .10 |
| Sex | .01 | 1.02 | .92 |
| Age | .01 | 0.99 | .93 |

TABLE 22

Cox regression analysis of impact of various factors on DSS of melanoma cohort

| PROGNOSTIC FACTOR | CHI-SQUARE | RISK RATIO | P VALUE |
|---|---|---|---|
| Multi-marker expression level | 8.25 | 1.31 | .004 |
| Tumor thickness | 6.58 | 1.62 | .01 |
| SLN status | 2.69 | 1.55 | .10 |
| Ulceration | 1.88 | 1.45 | .17 |
| Clark level | 1.25 | 1.24 | .26 |
| Sex | 0.20 | 1.13 | .66 |
| Age | 0.15 | 1.03 | .70 |
| Site | 0.09 | 1.08 | .77 |

It is understood that the examples and embodiments described herein are for illustrative purposes only and that various modifications or changes in light thereof will be suggested to persons skilled in the art and are to be included within the spirit and purview of this application and scope of the appended features and claims of the invention. All publications, patents, and patent applications cited herein are hereby incorporated by reference for all purposes.

The invention claimed is:

1. A method for diagnosing melanoma in a subject, the method comprising the steps of:
   (a) contacting a skin biopsy sample from the subject with antibodies that specifically bind each of polypeptides ARPC2, FN1, NCOA3, RGS1, SPP1, and WNT2; and
   (b) determining whether the polypeptides ARPC2, FN1, NCOA3, RGS1, SPP1, and WNT2 are over expressed in the skin biopsy sample as compared to a corresponding normal control; thereby providing a positive diagnosis for melanoma in the subject.

2. The method of claim 1, wherein the antibodies are labeled.

3. The method of claim 1, wherein said determining is performed using an enzyme immunoassay selected from the group consisting of immunohistochemical assay and ELISA.

4. The method of claim 1, wherein the step of determining comprises correlating elevated expression of the marker with the metastatic phenotype for cells in the sample.

5. The method of claim 1, wherein the diagnosis distinguishes between benign nevi versus malignant melanoma.

6. The method of claim 1, wherein the step of determining comprises the use of FISH or CGH.

7. A method for providing a prognosis for melanoma in a first subject, the method comprising the steps of:
   (a) contacting a melanocytic lesion sample from the first subject with (i) antibodies that specifically bind each of the polypeptides RGS1, NCOA3, SPP1, and PHIP; and
   (b) determining whether the polypeptides RGS1, NCOA3, SPP1, and PHIP, are over expressed in the melanocytic lesion sample from the first subject as compared to expression of RGS1, NCOA3, SPP1, and PHIP in a melanocytic lesion from a second subject; thereby providing a poorer relapse-free survival (RFS) or disease-specific survival (DSS) prognosis for melanoma in the first subject than for the second subject.

8. The method of claim 7, wherein said determining is performed using FISH or CGH.

9. The method of claim 7, wherein elevated expression of at least one selected marker is correlated with a prognosis selected from the group consisting of: metastasis to regional lymph nodes, relapse, and death.

* * * * *